US012331058B2

(12) United States Patent
Wu et al.

(10) Patent No.: US 12,331,058 B2
(45) Date of Patent: Jun. 17, 2025

(54) SHP2 AND CDK4/6 DUAL-TARGET INHIBITORY COMPOUND AND PHARMACEUTICAL COMPOSITION CONTAINING THE SAME

(71) Applicant: CHINA PHARMACEUTICAL UNIVERSITY, Jiangsu (CN)

(72) Inventors: Xiaoxing Wu, Jiangsu (CN); Xiaoyu Chen, Jiangsu (CN); Wenqiang Li, Jiangsu (CN); Chengxia Shu, Jiangsu (CN); Guangmei Luo, Jiangsu (CN); Kexin Yang, Jiangsu (CN)

(73) Assignee: CHINA PHARMACEUTICAL UNIVERSITY, Jiangsu (CN)

( * ) Notice: Subject to any disclaimer, the term of this patent is extended or adjusted under 35 U.S.C. 154(b) by 0 days.

(21) Appl. No.: 18/705,978

(22) PCT Filed: Jul. 21, 2022

(86) PCT No.: PCT/CN2022/106982
§ 371 (c)(1),
(2) Date: Apr. 29, 2024

(87) PCT Pub. No.: WO2023/071314
PCT Pub. Date: May 4, 2023

(65) Prior Publication Data

US 2025/0026756 A1 Jan. 23, 2025

(30) Foreign Application Priority Data

Oct. 29, 2021 (CN) ......................... 202111272628.3

(51) Int. Cl.

| | |
|---|---|
| ***C07D 487/04*** | (2006.01) |
| ***A61K 31/506*** | (2006.01) |
| ***A61K 31/519*** | (2006.01) |
| ***A61K 31/55*** | (2006.01) |
| ***A61P 35/00*** | (2006.01) |
| ***C07D 401/14*** | (2006.01) |
| ***C07D 491/107*** | (2006.01) |
| ***C07D 519/00*** | (2006.01) |

(52) U.S. Cl.
CPC .......... *C07D 487/04* (2013.01); *A61K 31/506* (2013.01); *A61K 31/519* (2013.01); *A61K 31/55* (2013.01); *A61P 35/00* (2018.01); *C07D 401/14* (2013.01); *C07D 491/107* (2013.01); *C07D 519/00* (2013.01)

(58) Field of Classification Search
None
See application file for complete search history.

(56) References Cited

FOREIGN PATENT DOCUMENTS

| | | |
|---|---|---|
| CN | 102264721 | 11/2011 |
| CN | 107998445 | 5/2018 |
| CN | 110143949 | 8/2019 |
| CN | 112203653 | 1/2021 |
| CN | 112203689 | 1/2021 |
| CN | 113461670 | 10/2021 |
| CN | 113968824 | 1/2022 |
| CN | 110382495 | 4/2022 |
| CN | 114302878 | 4/2022 |
| JP | 2018517752 | 7/2018 |
| JP | 2020515538 | 5/2020 |
| JP | 2021518441 | 8/2021 |
| WO | 2020073949 | 4/2020 |
| WO | 2020076723 | 4/2020 |
| WO | 2020216371 | 10/2020 |
| WO | 2021110122 | 6/2021 |
| WO | 2021142026 | 7/2021 |
| WO | 2021259077 | 12/2021 |

OTHER PUBLICATIONS

LaMarche et al., "Identification of TNO155, an Allosteric SHP2 Inhibitor for the Treatment of Cancer" J. Med. Chem. 2020, 63, 22, 13578-13594 (Year: 2020).*
"International Search Report (Form PCT/ISA/210) of PCT/CN2022/106982," mailed on Oct. 27, 2022, with English translation thereof, pp. 1-8.
"Written Opinion of the International Searching Authority (Form PCT/ISA/237) of PCT/CN2022/106982," mailed on Oct. 28, 2022, pp. 1-6.
"Office Action of Japan Counterpart Application", issued on Oct. 15, 2024, p. 1-p. 6.

* cited by examiner

*Primary Examiner* — Samantha L Shterengarts
*Assistant Examiner* — Jed A Kucharczk
(74) *Attorney, Agent, or Firm* — JCIPRNET

(57) ABSTRACT

The present invention belongs to the field of medicinal chemistry, and particularly relates to synthesis, a preparation method and the use of an inhibitor containing dual targets SHP2 and CDK4/6, wherein the inhibitor comprises three compounds of general formulas I-III and pharmaceutically acceptable salts, enantiomers, diastereomers, tautomers, solvates, polymorphs or prodrugs thereof. According to the present invention, a class of brand-new SHP2 and CDK4/6 dual-target inhibitors are prepared by means of a pharmacophore fusion and reasonable drug design method, so that the problems of drug resistance, poor drug effect, etc., of the existing SHP2 inhibitor and CDK4/6 inhibitor are solved; the great significance of the present invention is providing the first SHP2 and CDK4/6 dual-target inhibitor, which provides a basis for solving the problem of drug resistance of kinase and phosphatase in the later period.

6 Claims, 2 Drawing Sheets

SHP2 AND CDK4/6 DUAL-TARGET INHIBITORY COMPOUND AND PHARMACEUTICAL COMPOSITION CONTAINING THE SAME

CROSS-REFERENCE TO RELATED APPLICATION

This application is a 371 of international application of PCT application serial no. PCT/CN2022/106982, filed on Jul. 21, 2022, which claims the priority benefit of China application no. 202111272628.3, filed on Oct. 29, 2021. The entirety of each of the above mentioned patent applications is hereby incorporated by reference herein and made a part of this specification.

TECHNICAL FIELD

The present disclosure belongs to the field of pharmaceutical chemistry, and particularly relates to synthesis and preparation method and use of double-target inhibitors containing SHP2 and CDK4/6.

BACKGROUND

SHP2 is a non-receptor protein tyrosine phosphatase which is widely found in vivo, having two N-terminal Src homology 2 domains (N-SH2 and C-SH2), a catalytic domain (PTP), and a C-terminal tail. The two SH2 domains control subcellular localization and functional regulation of SHP2. As downstream signal molecules for growth factors such as platelet-derived growth factor (PDGF), epidermal growth Factor (EGF), fibroblast growth factor (FGF), interleukin-3(IL-3), leukemia Inhibitory Factor (LIF), Interferon α (INF-α) and the like, SHP2 participates in multiple signaling pathways, including the RAS/MARK pathway, PI3K/AKT pathway, JAK/STAT pathway, JNK pathway, and the like. Studies have shown that a mutation or over-activation of SHP2 will lead to the occurrence of Noonan syndrome, juvenile myelomonocytic leukemia, myelodysplastic syndrome, B-cell acute lymphoblastic leukemia, and solid tumors (lung cancer, colon cancer, neuroblastoma, melanoma, liver cancer).

CDKs are a class of serine/threonine protein kinases. Where CDK4/6 is a core regulator of the cell cycle, regulates the transformation at each stage of the cell cycle, and is one of important action targets of antitumor drugs. CDK4/6 inhibitor can generate anti-tumor activity by the mechanisms such as inhibiting tumor cell cycle transition from G1 phase to S phase, activating anti-tumor immune response, influencing tumor microenvironment, and has a better curative effect on certain types of tumors clinically. However, a long-time treatment with CDK4/6 inhibitor can easily lead to drug resistance in tumor, resulting in loss of efficacy of the inhibitors.

It was found that the administration of the SHP2 inhibitor in combination with the CDK4/6 inhibitor has a strong synergistic effect. At present, the combined administration enters a clinical phase I and is used for treating malignant tumors such as head and neck cancer, non-small cell lung cancer, colon cancer.

The present disclosure prepares a class of novel SHP2 and CDK4/6 double-target inhibitors through pharmacophore fusion and reasonable drug design, and provides a basis for solving the drug resistance problem of kinase and phosphatase in the later period.

SUMMARY

One of the technical problems to be solved by the present disclosure is a poor clinical curative effect and a drug resistance after long-term use of the SHP2 inhibitor and CDK4/6 inhibitor. Therefore, novel compounds containing SHP2 and CDK4/6 double-target inhibition are provided presumably for subsequent drug development.

The solutions for solving the technical problems are as follows.

1. Provided in the present disclosure is a compound as shown in General Formula I, and pharmaceutically acceptable salts, enantiomers, diastereomers, tautomers, solvates, polymorphs, or prodrugs thereof,

I

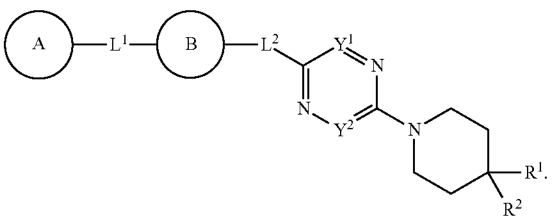

Ring A is selected from $C_3$-$C_6$ cycloalkyl, $C_6$-$C_{10}$ aromatic ring, $C_6$-$C_{10}$ heteroaromatic ring, mono-heterocyclic ring, spirocyclic ring, bridged ring, and fused ring; the cycloalkyl, the aromatic ring, the heteroaromatic ring, the mono-heterocyclic ring, the spirocyclic ring, the bridged ring, and the fused ring optionally contain heteroatoms selected from N, O and $S(O)_m$; where m is selected from 0, 1 and 2; where the cycloalkyl, the aromatic ring, the heteroaromatic ring, the carbocyclic ring, the mono-heterocyclic ring, the spirocyclic ring, the bridged ring, and the fused ring are optionally substituted with one or a plurality of substituents.

Ring B is selected from aromatic ring, heteroaromatic ring, carbocyclic ring, heterocyclic ring; the aromatic ring, the heteroaromatic ring, the carbocyclic ring, the heterocyclic ring optionally contain heteroatoms selected from N, O and $S(O)_m$; where m is selected from 0, 1 and 2; the aromatic ring, the heteroaromatic ring, the carbocyclic ring, the heterocyclic ring are optionally substituted with one or a plurality of substituents.

$L^1$ represents a chemical bond, $NR^a$, a carbon chain with $C_1$-$C_2$, O, $S(O)_m$, where m is selected from 0, 1 and 2.

$L^2$ represents a chemical bond, $NR^a$, a carbon chain with $C_1$-$C_2$, O, $S(O)_m$, where m is selected from 0, 1 and 2.

$Y^1$ represents N or $CR^3$, where $R^3$ is selected from hydrogen, deuterium atom, halogen, amino, hydroxy, cyano group, nitro, carboxyl, sulfonic acid group, $C_1$-$C_6$ alkyl, $C_1$-$C_6$ deuterated alkyl, $C_1$-$C_6$ alkoxy, $C_2$-$C_6$ alkenyl, $C_2$-$C_6$ alkynyl or $C_3$-$C_6$ cycloalkyl.

$Y^2$ represents N or $CR^4$, where $R^4$ is selected from hydrogen, deuterium atom, halogen, amino, hydroxy, cyano group, nitro, carboxyl, sulfonic acid group, $C_1$-$C_6$ alkyl, $C_1$-$C_6$ deuterated alkyl, $C_1$-$C_6$ alkoxy, $C_2$-$C_6$ alkenyl, $C_2$-$C_6$ alkynyl or $C_3$-$C_6$ cycloalkyl.

$R^1$,$R^2$ are hydrogen, deuterium atom, halogen, amino, hydroxy, cyano group, nitro, carboxyl, sulfonic acid group and $C_1$-$C_6$ alkyl, $C_3$-$C_6$ cycloalkyl, $C_6$-$C_{10}$ aryl, $C_6$-$C_{10}$ heteroaryl, respectively; the amino, the hydroxy, the aryl, the heteroaryl, the cycloalkyl are optionally substituted with one or a plurality of substituents.

Alternatively, a 3 membered to 12 membered mono-heterocyclic ring or polycyclic heterocyclic ring is formed by $R^1$ and $R^2$ together with carbon atoms attached to both $R^1$ and $R^2$, where the mono heterocyclic ring or the polycyclic heterocyclic ring optionally contains heteroatoms selected from N, O and $S(O)_m$; where m is selected from 0, 1 and 2; the mono-heterocyclic ring or the polycyclic heterocyclic ring is unsubstituted or substituted with one or a plurality of substituents.

Alternatively,

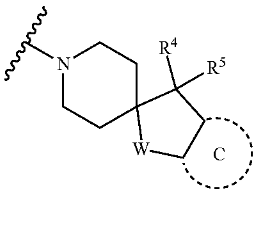

is formed by $R^1$ and $R^2$ together with the carbon atoms attached to both $R^1$ and $R^2$.

W is absent or selected from $CR^6R^7$, O, $NR^b$, $S(O)_m$, where m is selected from 0, 1 and 2.

Ring C is absent or selected from $C_3$-$C_7$ membered monocyclic ring or $C_5$-$C_{12}$ membered polycyclic rings.

$R^a$, $R^b$ are independently selected from hydrogen, deuterium atoms, $C_1$-$C_6$ alkyl, $C_3$-$C_6$ cycloalkyl, $C_6$-$C_{10}$ aryl, $C_6$-$C_{10}$ heteroaryl, respectively.

$R^4$, $R^5$, $R^6$, $R^7$ are independently selected from hydrogen, deuterium atom, halogen, amino, hydroxy, cyano, nitro, carboxyl, sulfonic acid group, $C_1$-$C_6$ alkyl, $C_3$-$C_6$ cycloalkyl, $C_6$-$C_{10}$ aryl, $C_6$-$C_{10}$ heteroaryl, respectively; the amino, the hydroxy, the aryl, the heteroaryl, the cycloalkyl are optionally substituted with one or a plurality of substituents.

Alternatively, CO, C═NH, $C_3$-$C_{12}$ membered heterocyclic rings or $C_3$-$C_5$ cycloalkyl is formed by $R^4$ and $R^5$ together with carbon atoms attached to both $R^4$ and $R^5$.

2. Further provided in the present disclosure is a compound as shown in General Formula II, and pharmaceutically acceptable salts, enantiomers, diastereomers, tautomers, solvates, polymorphs, or prodrugs thereof,

II

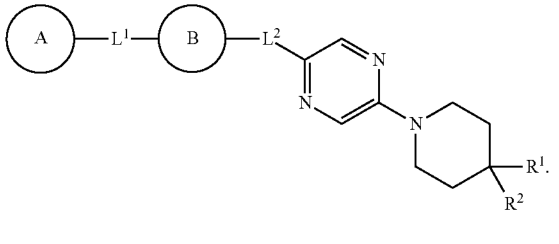

Ring A is selected from $C_3$-$C_6$ cycloalkyl, $C_6$-$C_{10}$ aromatic ring, $C_6$-$C_{10}$ heteroaromatic ring, mono-heterocyclic ring, spirocyclic ring, bridged ring, and fused ring; the cycloalkyl, the aryl, the heteroaromatic ring, the mono-heterocyclic ring, the spirocyclic ring, the bridged ring, and the fused ring optionally contain heteroatoms selected from N, O and $S(O)_m$; m is selected from 0, 1 and 2; the cycloalkyl, the aryl, the heteroaromatic ring, the carbocycle, the mono-heterocyclic ring, the spirocyclic ring, the bridged ring, and the fused ring are optionally substituted with one or a plurality of substituents.

Ring B is selected from aromatic ring, heteroaromatic ring, carbocyclic ring, heterocyclic ring; the aromatic ring, the heteroaromatic ring, the carbocyclic ring, the heterocyclic ring optionally contain heteroatoms selected from N, O and $S(O)_m$; m is selected from 0, 1 and 2; the aromatic ring, the heteroaromatic ring, the carbocyclic ring, the heterocyclic ring are optionally substituted with one or a plurality of substituents.

$L^1$ represents a chemical bond, $NR^a$, a carbon chain of $C_1$-$C_2$, O, $S(O)_m$, m is selected from 0, 1 and 2.

$L^2$ represents a chemical bond, $NR^a$, a carbon chain of $C_1$-$C_2$, O, $S(O)_m$, m is selected from 0, 1 and 2.

$R^1$, $R^2$ are hydrogen, deuterium atom, halogen, amino, hydroxy, cyano, nitro, carboxyl, sulfonic acid group and $C_1$-$C_6$ alkyl, $C_3$-$C_6$ cycloalkyl, $C_6$-$C_{10}$ aryl, $C_6$-$C_{10}$ heteroaryl, respectively; the amino, the hydroxy, the aryl, the heteroaryl, the cycloalkyl are optionally substituted with one or a plurality of substituents.

Alternatively, a 3 membered to 12 membered mono heterocyclic ring or polycyclic heterocyclic ring is formed by $R^1$ and $R^2$ together with the carbon atoms attached to both $R^1$ and $R^2$, the mono heterocyclic ring or the polycyclic heterocyclic ring optionally contains heteroatoms selected from N, O and $S(O)_m$; m is selected from 0, 1 and 2; the mono heterocyclic ring or the polycyclic heterocyclic ring is unsubstituted or substituted with one or a plurality of substituents.

Alternatively,

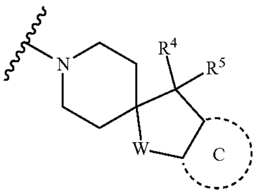

is formed by $R^1$ and $R^2$ together with the carbon atoms attached to both $R^1$ and $R^2$.

W is absent or selected from $CR^6R^7$, O, $NR^b$, $S(O)_m$, m is selected from 0, 1 and 2.

C ring is absent or selected from $C_3$-$C_7$ membered monocyclic rings or $C_5$-$C_{12}$ membered polycyclic rings.

$R^a$, $R^b$ are independently selected from hydrogen, deuterium atoms, $C_1$-$C_6$ alkyl, $C_3$-$C_6$ cycloalkyl, $C_6$-$C_{10}$ aryl, $C_6$-$C_{10}$ heteroaryl, respectively.

$R^4$, $R^5$, $R^6$, $R^7$ are independently selected from hydrogen, deuterium atom, halogen, amino, hydroxy, cyano, nitro, carboxyl, sulfonic acid group, $C_1$-$C_6$ alkyl, $C_3$-$C_6$ cycloalkyl, $C_6$-$C_{10}$ aryl, $C_6$-$C_{10}$ heteroaryl, respectively; the amino, the hydroxy, the aryl, the heteroaryl, the cycloalkyl are optionally substituted with one or a plurality of substituents.

Alternatively, CO, C═NH, $C_3$-$C_{12}$ membered heterocyclic rings or $C_3$-$C_8$ cycloalkyl is formed by $R^4$ and $R^5$ together with carbon atoms attached to both $R^4$ and $R^5$.

3. Further provided in the present disclosure is a compound as shown in General Formula III, and pharmaceutically acceptable salts, enantiomers, diastereomers, tautomers, solvates, polymorphs, or prodrugs thereof,

III

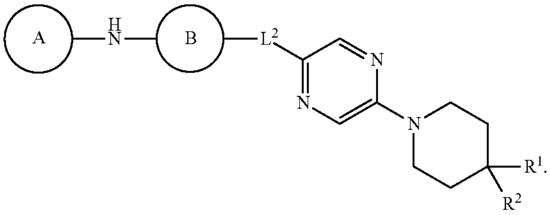

Ring A is selected from hydrogen,

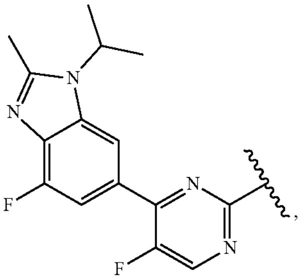

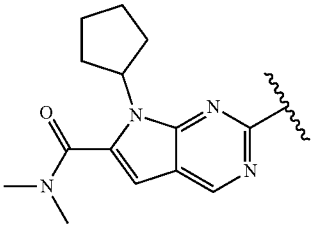

or

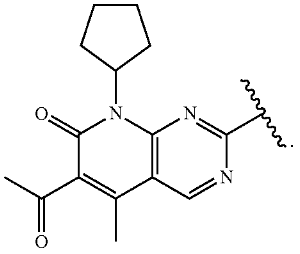

Ring B is selected from aromatic ring, heteroaromatic ring, carbocyclic ring, heterocyclic ring; the aromatic ring, the heteroaromatic ring, the carbocyclic ring, the heterocyclic ring optionally contains heteroatoms selected from N, O and $S(O)_m$; where m is selected from 0, 1 and 2; where the aromatic rings, heteroaromatic rings, carbocyclic rings, heterocyclic rings are optionally substituted with one or a plurality of substituents.

$L^2$ is a chemical bond, $NR^a$, a carbon chain with $C_1$-$C_2$, O, $S(O)_m$, where m is selected from 0, 1 and 2.

$R^1$, $R^2$ are hydrogen, deuterium atom, halogen, amino, hydroxy, cyano, nitro, carboxyl, sulfonic acid group and $C_1$-$C_6$ alkyl, $C_3$-$C_6$ cycloalkyl, $C_6$-$C_{10}$ aryl, $C_6$-$C_{10}$ heteroaromatic, respectively; the amino, the hydroxy, the aryl, the heteroaryl, the cycloalkyl are optionally substituted with one or a plurality of substituents.

Alternatively, a 3 membered to 12 membered mono heterocyclic ring or polycyclic heterocyclic ring is formed by $R^1$ and $R^2$ together with the carbon atoms attached to both $R^1$ and $R^2$, the mono-heterocyclic ring or the polycyclic heterocyclic ring optionally contains heteroatoms selected from N, O and $S(O)_m$; m is selected from 0, 1 and 2; where the mono heterocyclic ring or the polycyclic heterocyclic ring is unsubstituted or substituted with one or a plurality of substituents.

Alternatively,

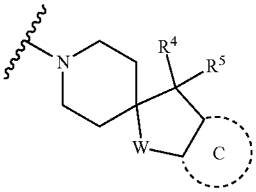

is formed by $R^1$ and $R^2$ together with the carbon atoms attached to both $R^1$ and $R^2$.

W is absent or selected from $CR^6R^7$, O, $NR^b$, $S(O)_m$, where m is selected from 0, 1 and 2.

Ring C is absent or selected from $C_3$-$C_7$ membered monocyclic ring or $C_5$-$C_{12}$ membered polycyclic ring.

$R^a$, $R^b$ are independently selected from hydrogen, deuterium atoms, $C_1$-$C_6$ alkyl, $C_3$-$C_6$ cycloalkyl, $C_6$-$C_{10}$ aryl, $C_6$-$C_{10}$ heteroaryl.

$R^4$, $R^5$, $R^6$, $R^7$ are independently selected from hydrogen, deuterium atom, halogen, amino, hydroxy, cyano, nitro, carboxyl, sulfonic acid group, $C_1$-$C_6$ alkyl, $C_3$-$C_6$ cycloalkyl, $C_6$-$C_{10}$ aryl, $C_6$-$C_{10}$ heteroaryl; where the amino, the hydroxy, the aryl, the heteroaryl, the cycloalkyl are optionally substituted with one or a plurality of substituents.

Alternatively, CO, C═NH, $C_3$-$C_{12}$ membered heterocyclic ring or $C_3$-$C_8$ cycloalkyl is formed by $R^4$ and $R^5$ together with the carbon atoms attached to both $R^4$ and $R^5$.

Further provided is a pharmaceutical composition. The pharmaceutical composition contains compounds I-III and pharmaceutically acceptable auxiliary materials.

The pharmaceutical composition is characterized in that the pharmaceutical composition is prepared into a tablet, a capsule, an injection or a lyophilized powder.

The aromatic spirocyclic compound and the pharmaceutical composition are applied to preparations of anti-tumor drugs, prodrugs as anti-tumor drugs or intermediates as antitumor drugs.

The design idea is as follows:

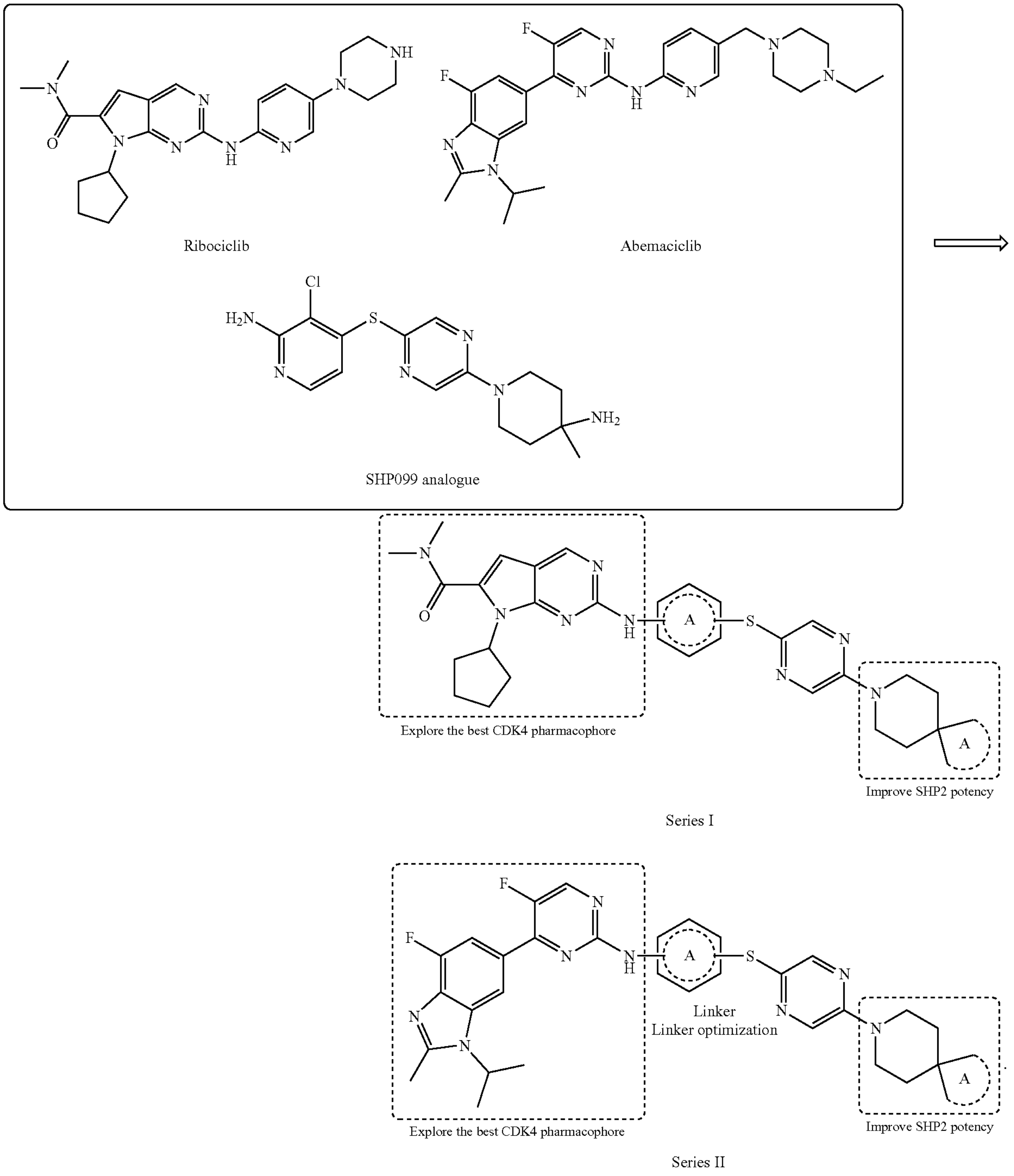

In the design of double-target drugs, the design method of pharmacophore fusion can currently avoid the problems such as high molecular weight, poor metabolism. In the design of the SHP2/CDK4 double-target inhibitor, it is observed that both have pyridine rings and that the modifications are at the edge of the solvent region, thus innovatively combining the pharmacophores and linking groups of both. Due to the difficulty in balancing the activities of the fusion type double-target inhibitor before two targets, the influence of different pharmacophores and connecting groups on the inhibition activity is simply explored, and the compounds 1-26 are obtained.

It is found through SAR analysis that compounds with two pharmacophores connected in para position through the pyridine ring can retain CDK4 activity but reduce SHP2 activity; compounds that link two pharmacophores through the pyridine ring meta-position may retain SHP2 activity but may reduce CDK activity; the pharmacophore overall effect of Abemaciclib is better than that of Ribociclib; in summary, SAR for SHP2/CDK4 double-target inhibitors is explored by synthesizing 26 compounds and a plurality of compounds with double-target inhibitory activity are obtained.

Advantageous Effects

1. The present disclosure provide a novel SHP2 and CDK4/6 double-target inhibitor based on pharmacophore fusion and reasonable drug design, so as to solve the problems such as drug resistance, poor drug effect appearing on the existing SHP2 inhibitor and CDK4/6 inhibitor.

2. In vitro enzyme activity and antiproliferative activity tests, compounds 10, 14, 19, 23, 25, 26 showed better double-target inhibition activity; in cell cycle experimental tests, compound 14 showed better cycle G0/G1 phase arrest.

3. The structures of the specific examples are as follows:

| Number | Structure of the compound |
|---|---|
| 1 | 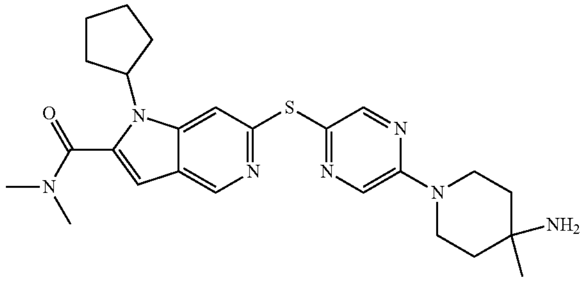 [SMILES: CN(C)C(=O)c1cc2cnc(Sc3cnc(N4CCC(C)(N)CC4)cn3)cc2n1C1CCCC1] |
| 2 | 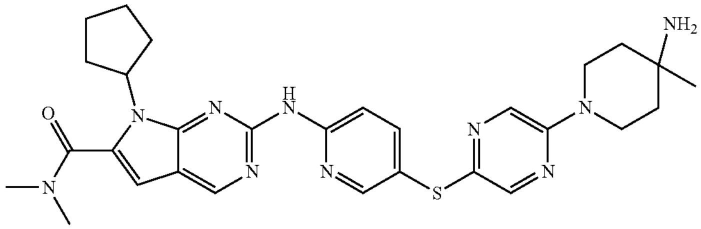 |
| 3 | 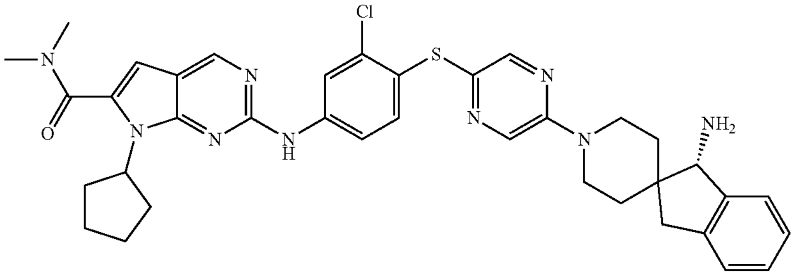 [SMILES: CN(C)C(=O)c1cc2cnc(Nc3ccc(Sc4cnc(N5CCC6(CC5)Cc5ccccc5[C@H]6N)cn4)c(Cl)c3)nc2n1C1CCCC1] |
| 4 | 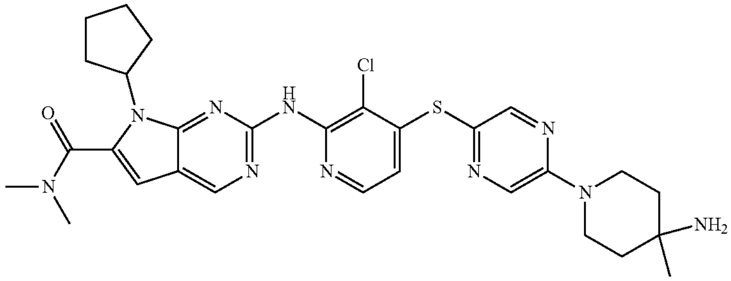 [SMILES: CN(C)C(=O)c1cc2cnc(Nc3nccc(Sc4cnc(N5CCC(C)(N)CC5)cn4)c3Cl)nc2n1C1CCCC1] |

-continued
| Number | Structure of the compound |
| --- | --- |
| 5 | 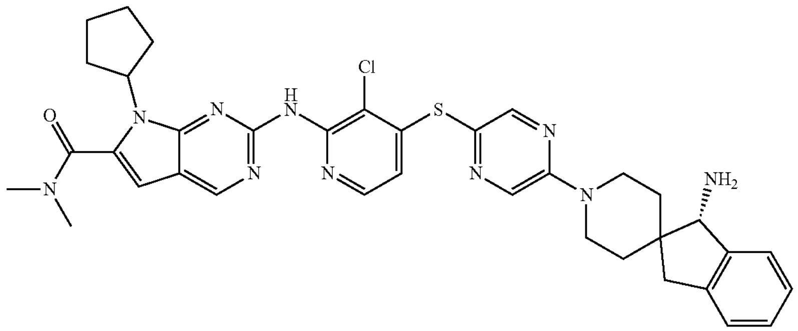 [SMILES: CN(C)C(=O)c1cc2cnc(Nc3nccc(Sc4cnc(N5CCC6(CC5)Cc5ccccc5[C@H]6N)cn4)c3Cl)nc2n1C1CCCC1] |
| 6 | 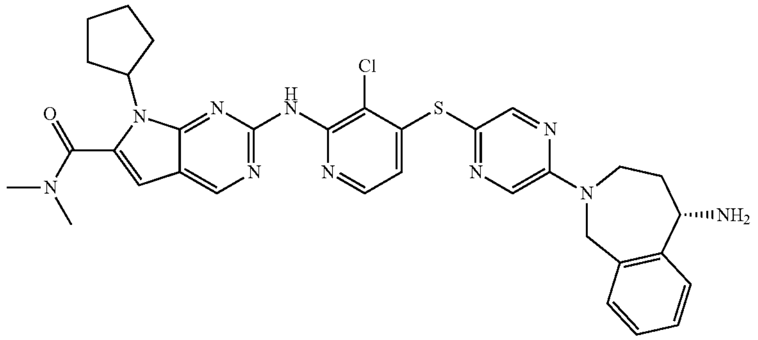 [SMILES: CN(C)C(=O)c1cc2cnc(Nc3nccc(Sc4cnc(N5CC[C@H](N)c6ccccc6C5)cn4)c3Cl)nc2n1C1CCCC1] |
| 7 | 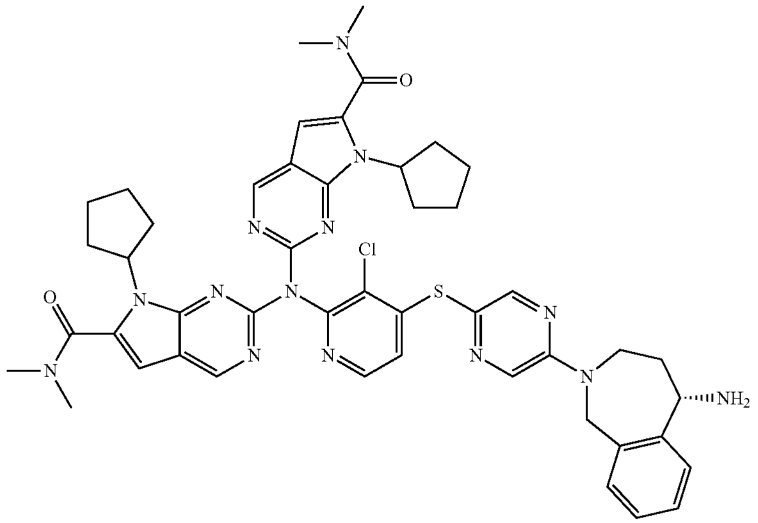 [SMILES: CN(C)C(=O)c1cc2cnc(N(c3ncc4cc(C(=O)N(C)C)n(C5CCCC5)c4n3)c3nccc(Sc4cnc(N5CC[C@H](N)c6ccccc6C5)cn4)c3Cl)nc2n1C1CCCC1] |
| 8 | 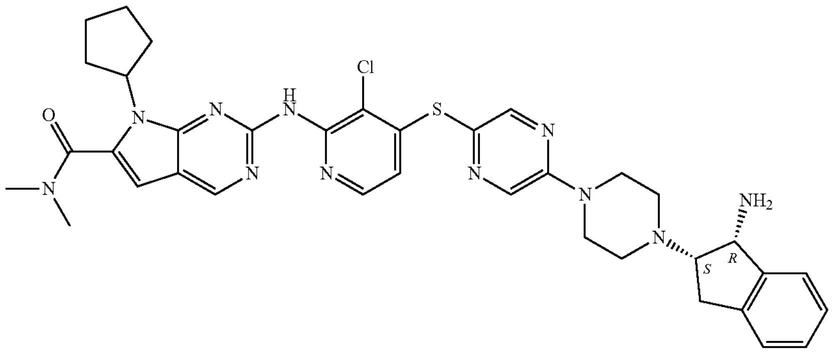 |

-continued
| Number | Structure of the compound |
|---|---|
| 9 | 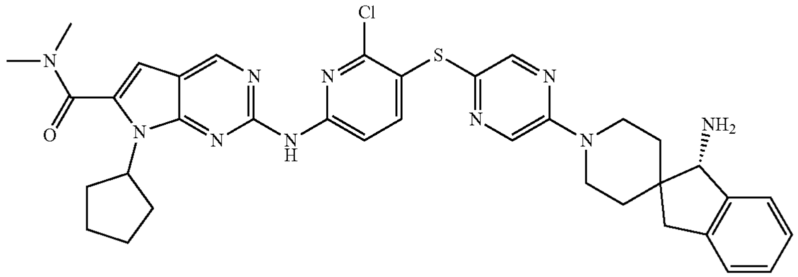 [SMILES: CN(C)C(=O)c1cc2cnc(Nc3ccc(Sc4cnc(N5CCC6(CC5)Cc5ccccc5[C@H]6N)cn4)c(Cl)n3)nc2n1C1CCCC1] |
| 10 | 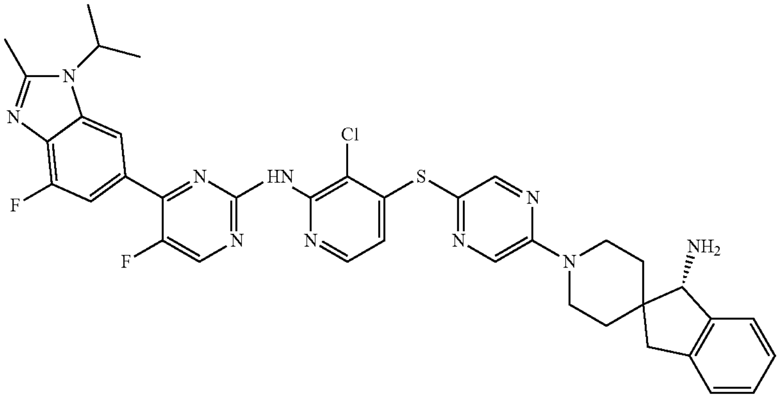 [SMILES: Cc1nc2c(F)cc(-c3nc(Nc4nccc(Sc5cnc(N6CCC7(CC6)Cc6ccccc6[C@H]7N)cn5)c4Cl)ncc3F)cc2n1C(C)C] |
| 11 | 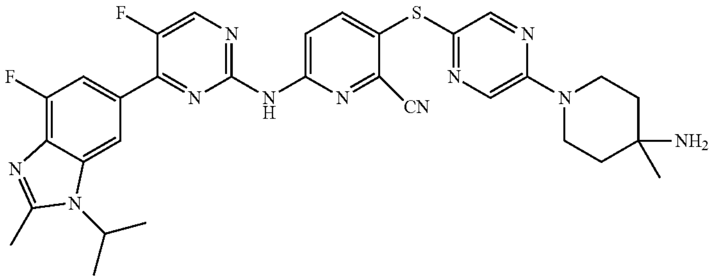 [SMILES: Cc1nc2c(F)cc(-c3nc(Nc4ccc(Sc5cnc(N6CCC(C)(N)CC6)cn5)c(C#N)n4)ncc3F)cc2n1C(C)C] |
| 12 | 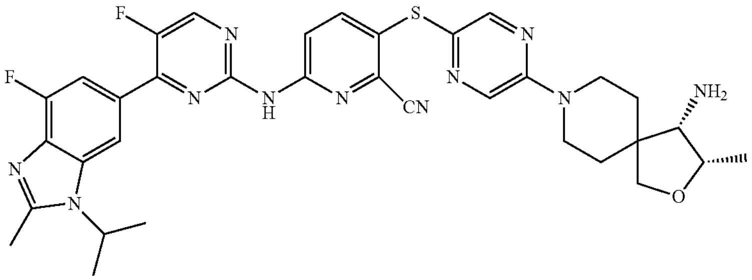 [SMILES: Cc1nc2c(F)cc(-c3nc(Nc4ccc(Sc5cnc(N6CCC7(CC6)CO[C@@H](C)[C@H]7N)cn5)c(C#N)n4)ncc3F)cc2n1C(C)C] |
| 13 | 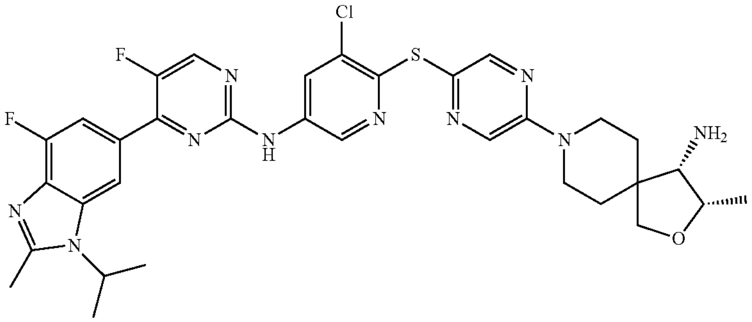 [SMILES: Cc1nc2c(F)cc(-c3nc(Nc4cnc(Sc5cnc(N6CCC7(CC6)CO[C@@H](C)[C@H]7N)cn5)c(Cl)c4)ncc3F)cc2n1C(C)C] |

-continued
| Number | Structure of the compound |
|---|---|
| 14 | 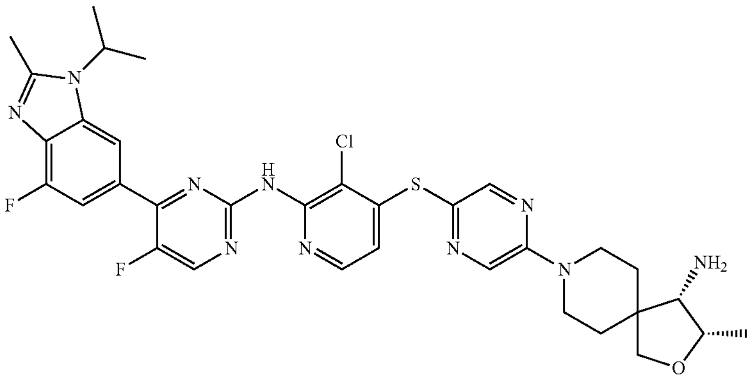 [SMILES: Cc1nc2c(F)cc(-c3nc(Nc4nccc(Sc5cnc(N6CCC7(CC6)CO[C@@H](C)[C@H]7N)cn5)c4Cl)ncc3F)cc2n1C(C)C] |
| 15 | 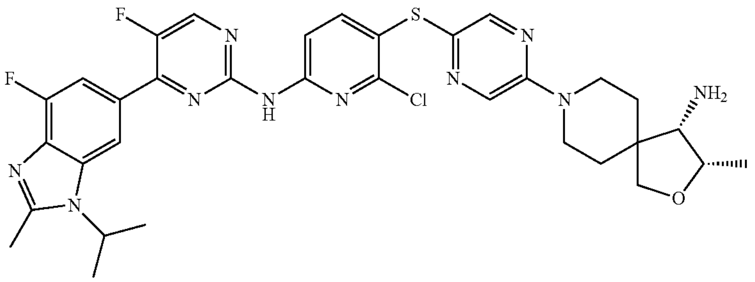 [SMILES: Cc1nc2c(F)cc(-c3nc(Nc4ccc(Sc5cnc(N6CCC7(CC6)CO[C@@H](C)[C@H]7N)cn5)c(Cl)n4)ncc3F)cc2n1C(C)C] |
| 16 | 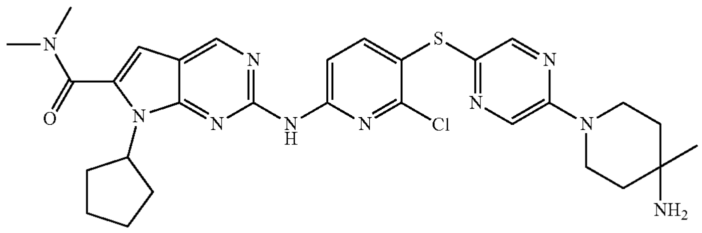 |
| 17 | 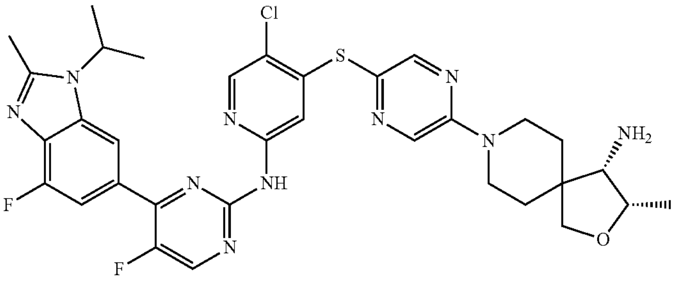 [SMILES: Cc1nc2c(F)cc(-c3nc(Nc4cc(Sc5cnc(N6CCC7(CC6)CO[C@@H](C)[C@H]7N)cn5)c(Cl)cn4)ncc3F)cc2n1C(C)C] |
| 18 | 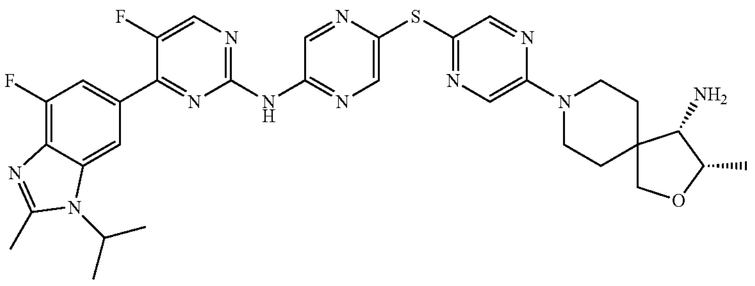 [SMILES: Cc1nc2c(F)cc(-c3nc(Nc4cnc(Sc5cnc(N6CCC7(CC6)CO[C@@H](C)[C@H]7N)cn5)cn4)ncc3F)cc2n1C(C)C] |

-continued
| Number | Structure of the compound |
| --- | --- |
| 19 | 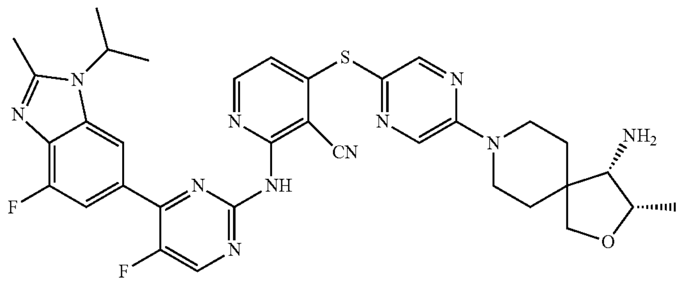 [SMILES: Cc1nc2c(F)cc(-c3nc(Nc4nccc(Sc5cnc(N6CCC7(CC6)CO[C@@H](C)[C@H]7N)cn5)c4C#N)ncc3F)cc2n1C(C)C] |
| 20 | 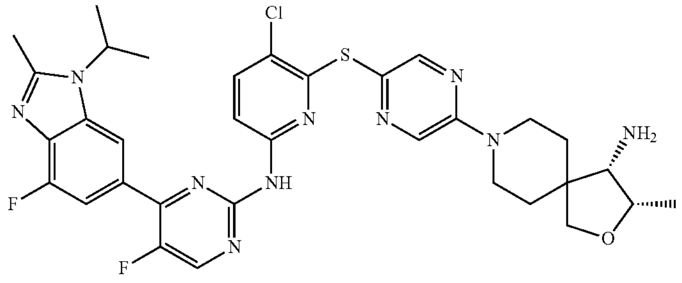 [SMILES: Cc1nc2c(F)cc(-c3nc(Nc4ccc(Cl)c(Sc5cnc(N6CCC7(CC6)CO[C@@H](C)[C@H]7N)cn5)n4)ncc3F)cc2n1C(C)C] |
| 21 | 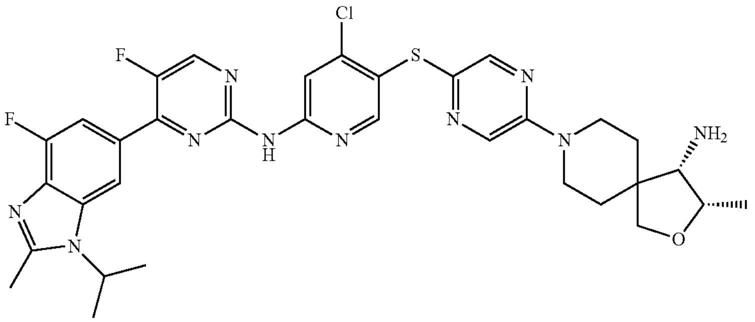 |
| 22 | 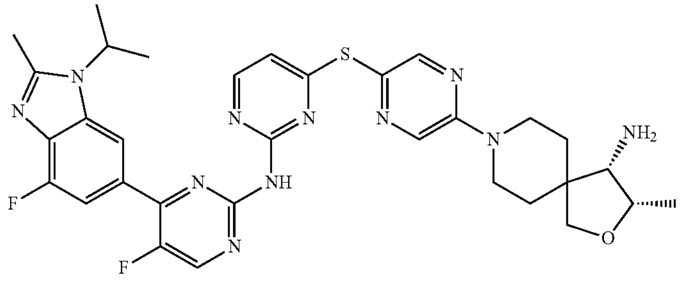 [SMILES: Cc1nc2c(F)cc(-c3nc(Nc4nccc(Sc5cnc(N6CCC7(CC6)CO[C@@H](C)[C@H]7N)cn5)n4)ncc3F)cc2n1C(C)C] |
| 23 | 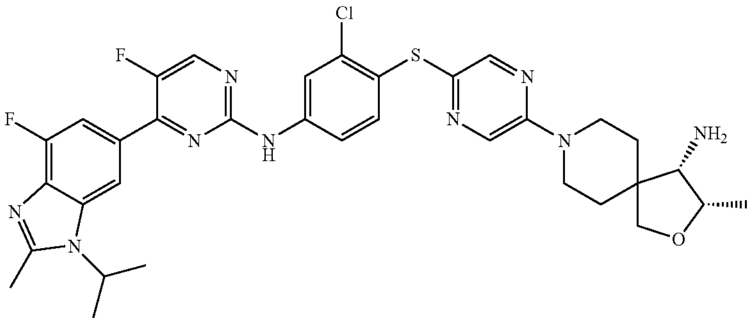 [SMILES: Cc1nc2c(F)cc(-c3nc(Nc4ccc(Sc5cnc(N6CCC7(CC6)CO[C@@H](C)[C@H]7N)cn5)c(Cl)c4)ncc3F)cc2n1C(C)C] |

-continued

| Number | Structure of the compound |
|---|---|
| 24 | 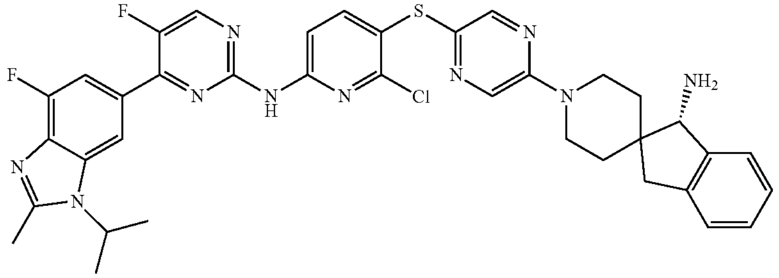 [SMILES: Cc1nc2c(F)cc(-c3nc(Nc4ccc(Sc5cnc(N6CCC7(CC6)Cc6ccccc6[C@H]7N)cn5)c(Cl)n4)ncc3F)cc2n1C(C)C] |
| 25 | 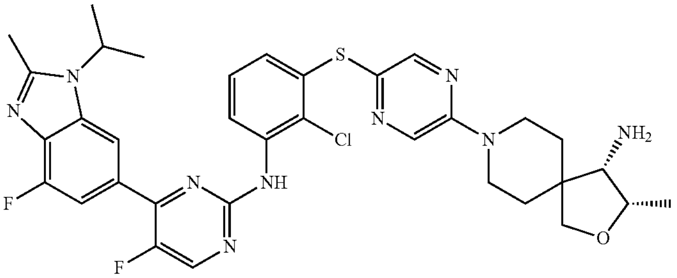 [SMILES: Cc1nc2c(F)cc(-c3nc(Nc4cccc(Sc5cnc(N6CCC7(CC6)CO[C@@H](C)[C@H]7N)cn5)c4Cl)ncc3F)cc2n1C(C)C] |
| 26 | 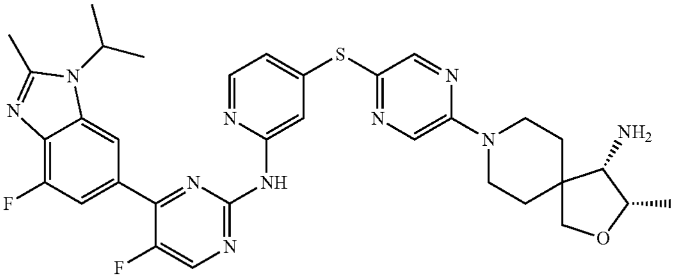 [SMILES: Cc1nc2c(F)cc(-c3nc(Nc4cc(Sc5cnc(N6CCC7(CC6)CO[C@@H](C)[C@H]7N)cn5)ccn4)ncc3F)cc2n1C(C)C] |

DETAILED DESCRIPTION

Figure 1:
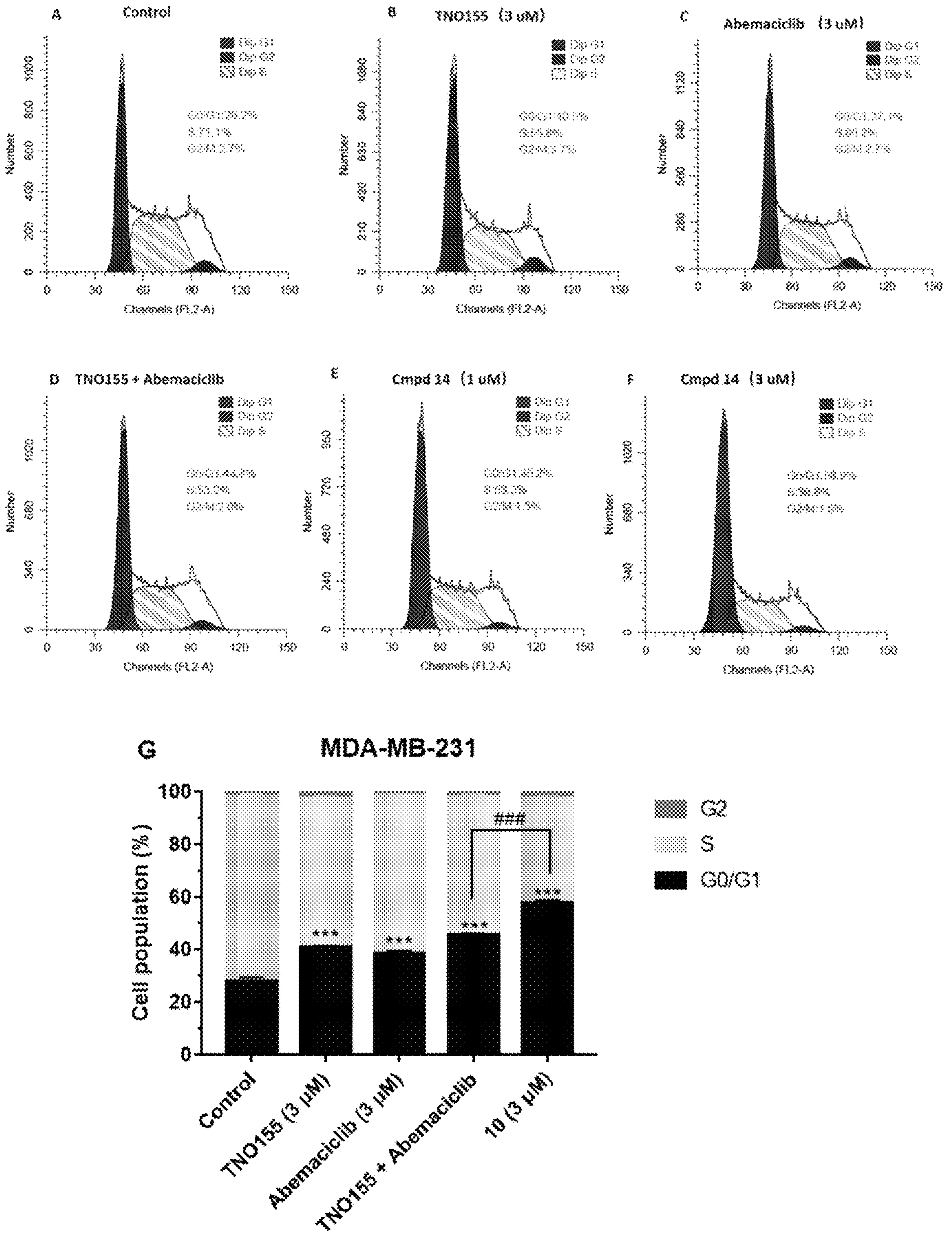
FIG. 1 illustrates an influence of Compound 14 on a cell cycle of MDA-MB-231; where A is control, B is TNO155, C is Abemaciclib, D is TNO155+Abemaciclib, E is Cmpd14 (1μ M), F is Cmpd14 (6μ M).

Synthesis of Intermediate 5-Chloro-2-Pyrazine Sodium Sulfide (II-1) is as Follows:

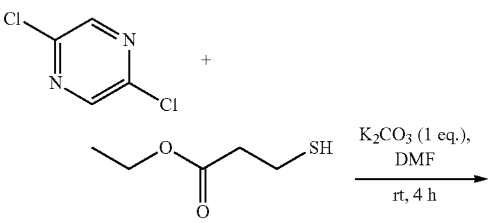

-continued

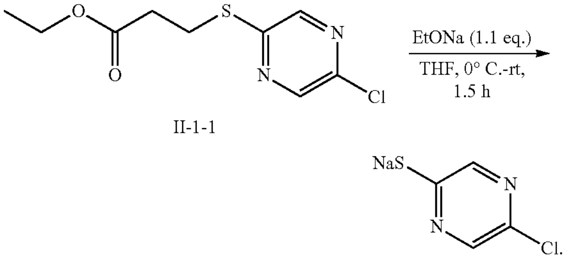

II-1-1

II-1

Step One: Synthesis of Compound II-1-1

Compound 2,5-dichloropyrazine (5.00 g, 33.6 mmol), ethyl 3-mercaptopropionate (4.73 g, 1.05 eq.) and potassium carbonate (4.64 g, 33.6 mmol) are placed in a 100 mL single-necked flask at the room temperature, and DMF is added. The reaction mixture is reacted for 4 hours. The reaction mixture is monitored through TLC plate until the conversion of raw material is completed. Ethyl acetate is added and the reaction mixture is washed with saturated sodium chloride aqueous solution for a plurality of times. The organic phase is concentrated, purified by column chromatography to obtain compound I1-1-1 (7.78 g, yield 94%).

Step Two: Synthesis of Compound II-1

Compound II-1-1 (7.38 g, 30.0 mmol) is dissolved in THF at 0° C., and sodium ethoxide (2.25 g, 33.0 mmol, 1.1 eq.) is added in batches. The reaction mixture is detected at the room temperature until the reaction of raw material is monitored to be complete, filtrated to obtain solid compound II-1 (5.13 g, crude product).

Synthesis of Intermediate (III-1) is as Follows:

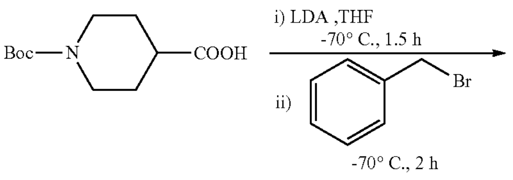

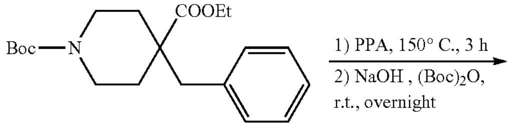

III-1-1

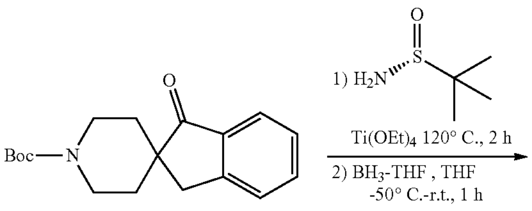

III-1-2

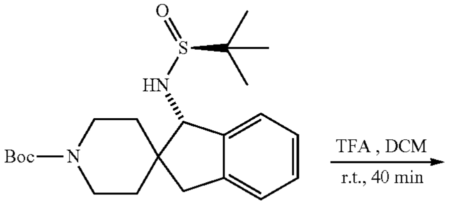

III-1-3

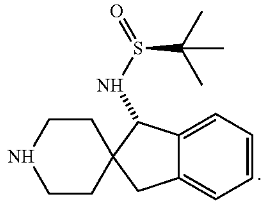

III-1

Step one: Synthesis of Compound III-1-1

N-tert-butoxycarbonyl-4-ethyl formate piperidine (19.00 g, 73.9 mmol) is dissolved in THF at −70° C., and LDA (1.28 eq.) is slowly dripped. The reaction mixture is reacted for 1.5 hours. Benzyl bromide (1.1 eq.) is added and the temperature is kept for 2 hours. The reaction mixture is monitored by TLC plate until the conversion of raw material is completed, quenched by a slow dropwise addition of saturated ammonium chloride, extracted with ethyl acetate, dried with anhydrous sodium sulfate, concentrated, separated by column chromatography to obtain compound III-1-1 (15.10 g, yield 58%).

Step Two: Synthesis of Compound III-1-2

Compound III-1-1 (12.00 g, 34.6 mmol) and PPA (1.35 eq.) are placed in a 50 mL single-port bottle and reacted at 150° C. for 3 hours. The reaction mixture is monitored by TLC plate until the conversion of raw material is completed. Sodium hydroxide (2 M) is added to adjust pH value to be basic at a low temperature and BOC anhydride (12.10 g, 55.4 mmol, 1.6 eq.) is added. The reaction mixture is reacted overnight, monitored by TLC plate until the conversion of raw material is completed, extracted with ethyl acetate, dried with anhydrous sodium sulfate, concentrated, and separated by column chromatography to obtain compound III-1-2 (3.95 g, yield 38%).

Step three: Synthesis of Compound III-1-3

Compound III-1-2 (4.80 g, 15.9 mmol), tert-butylsulfonamide (4.05 g, 33.4 mmol, 2.1 eq.) and tetraethyl titanate (24 mL) are placed in a 100 mL single-port bottle. The reaction mixture is reacted at 120° C. for 2 hours, and monitored by TLC plate until the conversion of raw material is completed. $BH_3$-THF (614.4 mg, 44.5 mmol, 2.8 eq.) is added slowly at −50° C.

Then, the reaction mixture is reacted at room temperature for 1 hour, and monitored by TLC plate until the conversion of raw material is completed. The reaction mixture is quenched by slowly dropping saturated ammonium chloride at −50° C., extracted with ethyl acetate, dried with anhydrous sodium sulfate, concentrated, and separated by column chromatography to obtain compound III-1-3 (3.10 g, yield 48%).

Step four: Synthesis of Compound III-1

III-1-3 (3.1 g, 7.64 mmol) is dissolved in DCM (30 mL) and trifluoroacetic acid (9 eq.) is slowly added. The reaction mixture is reacted overnight at the room temperature. The reaction mixture is adjusted on a pH value to be alkaline through adding sodium carbonate solution after the reaction is monitored to be complete, extracted with DCM, dried and concentrated to obtain the compound III-1 (2.30 g, yield 98%).

Synthesis of intermediate (III-2):

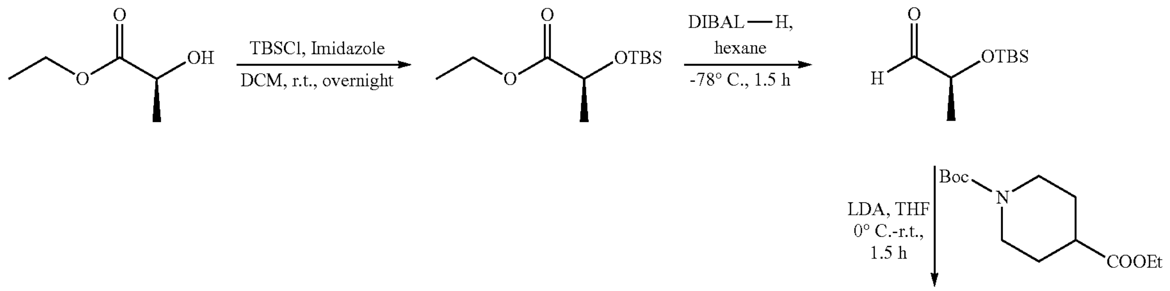

-continued

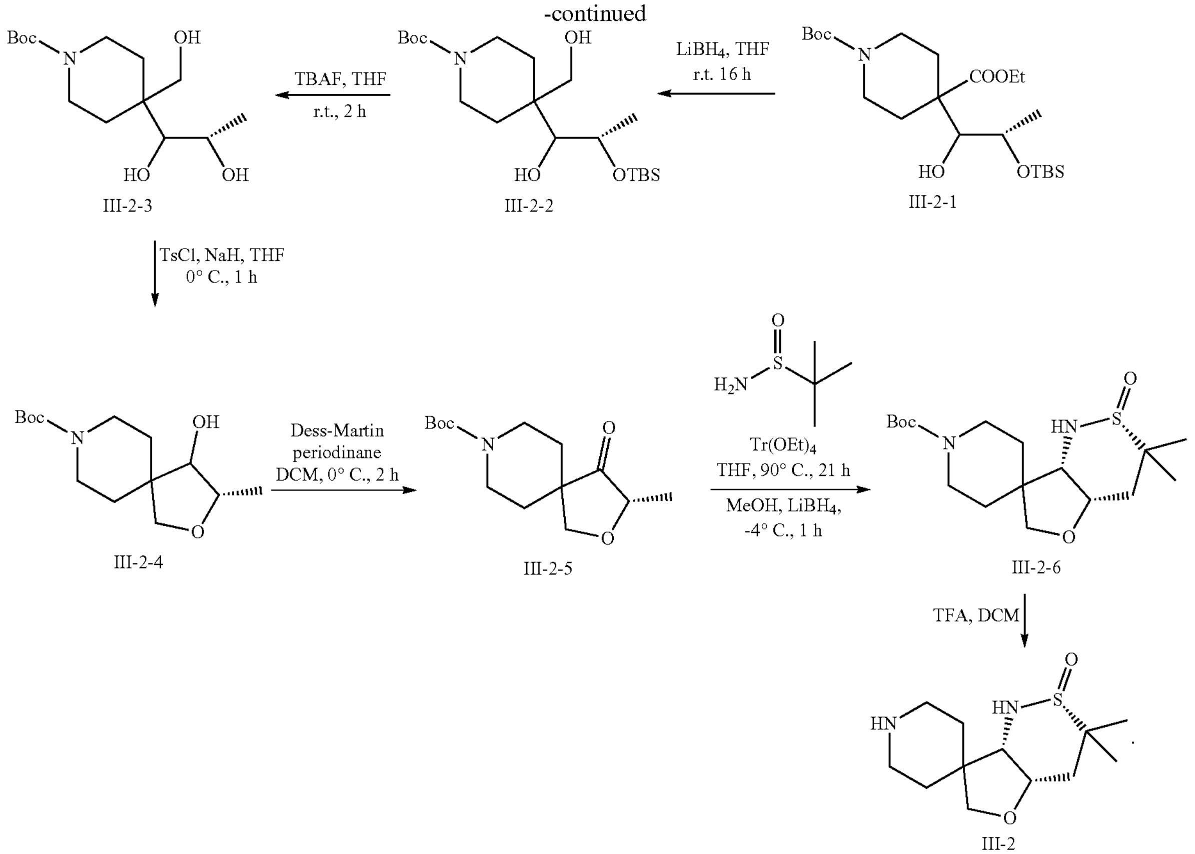

III-2-3

III-2-2

III-2-1

III-2-4

III-2-5

III-2-6

III-2

Step one: Synthesis of compound ethyl(S)-2-(tert-butyldimethylsilyloxy)propionate Compound ethyl (S)-2-hydroxypropionate (40 g, 338.6 mmol), TBSCl (76.6 g, 507.9 mmol, 1.5 eq.) and imidazole (460 g, 677.2 mmol, 2.0 eq) are dissolved in DCM and reacted overnight at the room temperature. The reaction mixture is monitored by TLC plate until the conversion of raw material is completed, extracted with ethyl acetate, dried with anhydrous sodium sulfate, concentrated, and separated by column chromatography to obtain compound ethyl(S)-2-((tert-butyldimethylsilyloxy)propionate (90.00 g, crude).

Step two: Synthesis of Compound (S)-2-(tert-butyldimethylsilyl)oxy)propanal

DIBAL-H (361.9 mL, 361.9 mmol, 1.3 eq.) is slowly added dropwise to a solution of compound ethyl(S)-2-(tert-butyldimethylsilyloxy)propionate (70.7 g, 304.4 mmol) in hexane (650 mL) at −78° C. The reaction mixture is reacted for 1 hour and then placed at 0° C. for 30 min. The reaction mixture is stirred at −78° C. after the reaction is monitored to be complete, quenched by a slow dropwise addition of sodium potassium tartrate (aq.), extracted with ethyl acetate, dried with anhydrous sodium sulfate, concentrated, and separated by column chromatography to obtain the compound (S)-2-((tert-butyldimethylsilyl)oxy)propanal (38.6 g, yield 41% in two steps).

Step three: Synthesis of Compound III-2-1

The compound N-(tert-butoxycarbonyl)-4-piperidinecarboxylic acid ethyl ester (101.5 g, 394.5 mmol, 1.0 eq.) is dissolved in THF (742 mL). LDA (295.9 mL, 591.8 mmol, 1.5 eq.) is added in a slow dropwise at 0° C. Compound (S)-2-((tert-butyldimethylsily)loxy)propanal (74.3 g, 394.5 mmol) is added in batches. The reaction mixture is reacted at the room temperature for 1.5 hours. The reaction mixture is monitored by TLC plate until the conversion of raw material is completed, quenched, extracted with ethyl acetate, dried with anhydrous sodium sulfate, concentrated, separated by column chromatography to obtain compound III-2-1 (163.4 g, yield 93%).

Step four: Synthesis of Compound III-2-2

$LiBH_4$ (12 g, 550.2 mmol, 1.5 eq.) is added at 0° C. in batches to a solution of compound III-2-1 (163.35 g, 366.8 mmol) in THF (700 mL). The reaction mixture is reacted at the room temperature overnight. The reaction mixture is stirred at 0° C. after the reaction is monitored to be complete, and quenched with a slow dropwise addition of $NH_4C_1$ (aq.), extracted with DCM, dried with anhydrous sodium sulfate, and concentrated to obtain compound III-2-2 (103.7 g, yield 70%).

Step five: Synthesis of Compound III-2-3

Compound III-2-2 (103.7 g, 257.1 mmol), TBAF (282.9 mL, 282.9 mmol, 1.1 eq.) are dissolved in THF (500 mL). The reaction mixture is reacted at room temperature for 2 hours. The reaction mixture is monitored by TLC plate until the conversion of raw material is completed, extracted with ethyl acetate, dried with anhydrous sodium sulfate, concentred, separated by column chromatography to obtain compound III-2-3 (104.7 g, crude).

Step six: Synthesis of Compound III-2-4

Compound III-2-3 (104.7 g, 363.3 mmol), TsCl (55.4 g, 290.6 mmol, 0.8 eq.) are dissolved in THF (600 mL). Sodium hydrogen (30.5 g, 127.2 mmol, 2.0 eq.) is added slowly at 0° C. The reaction mixture is reacted for 1 hour. The reaction mixture is monitored by TLC plate until the conversion of raw material is completed, quenched, extracted with ethyl acetate, dried with anhydrous sodium sulfate, concentrated, separated by column chromatography to obtain compound III-2-4 (4.3.9 g, yield 63%).

Step seven: Synthesis of Compound III-2-5

Compound III-2-4 (43.9 g, 161.9 mmol) is dissolved in DCM at 0° C. and Dessmartin oxidant (89.3 g, 1.3 mmol) is added. The reaction mixture is reacted for 2 hours. The reaction mixture is monitored by TLC plate until the conversion of raw material is completed, quenched, extracted with ethyl acetate, dried with anhydrous sodium sulfate, concentrated, and separated by column chromatography to obtain compound III-2-5 (41.3 g, crude).

Step eight: Synthesis of Compound III-2-6

Compound III-2-5 (41.3 g, 153.3 mmol), tert-butylsulfonamide (37.2 g, 306.6 mmol, 2.0 eq.) and tetraethoxytitanate (139.9 g, 613.2 mmol, 4.0 eq.) are dissolved in THF (300 mL) and placed in a 100 mL single-necked flask. The reaction mixture is reacted at 90° C. for 21 hours. The reaction mixture is monitored by TLC plate until the conversion of raw material is completed, reacted at room temperature for 1 hour. $LiBH_4$ (6.7 mg, 306.6 mmol, 2.0 eq.) is added and dissolved in methanol at −4° C. The reaction mixture is monitored by TLC plate until the conversion of raw material is completed, extracted with ethyl acetate, dried with anhydrous sodium sulfate, concentrated, separated by column chromatography to obtain compound III-2-6 (34.6 g, crude).

Step nine: Synthesis of intermediate III-2

III-2-6 (1 g, 2.67 mmol) is dissolved in DCM (10 mL) and trifluoroacetic acid (2 mL) is slowly added. The reaction mixture is reacted overnight at the room temperature. The reaction mixture is monitored by TLC plate until the conversion of raw material is completed, adjusted on a pH value to be alkaline through adding sodium carbonate solution after the reaction is monitored to be complete, extracted with ethyl acetate, and dried and concentrated to obtain Compound III-2 (150.0 mg, total yield 20% in three steps).

Synthesis of intermediate (I-1):

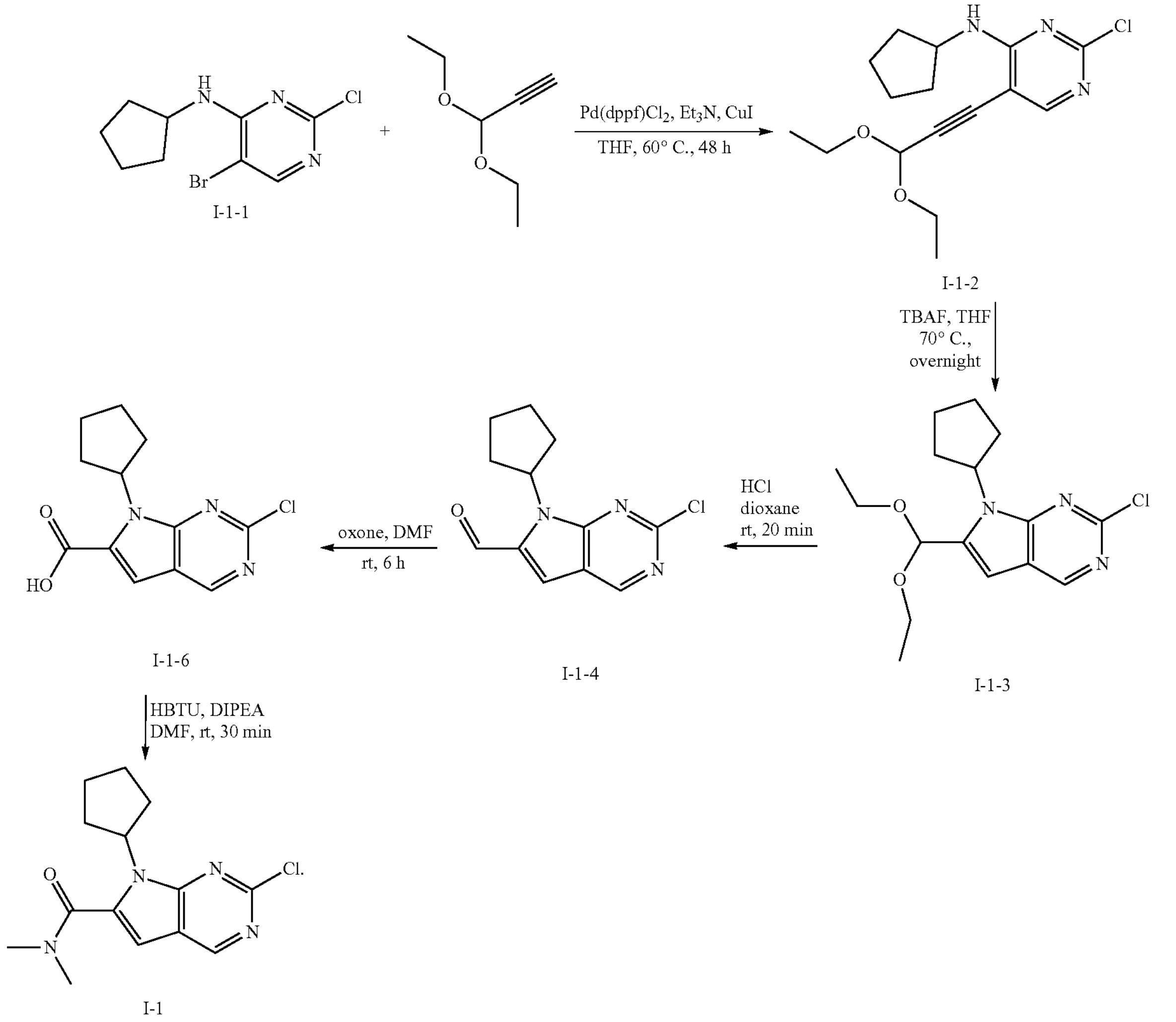

I-1-1, I-1-2, I-1-3, I-1-4, I-1-6, I-1

Step one: Synthesis of Compound I-1-2

Compound I-1-1 (17.60 g, 63.6 mmol), propionaldehyde diethyl acetal (12.20 mg, 95.4 mmol, 1.5 eq.) $Pd(dppf)Cl_2$ (930.1 mg, 0.02 eq.) and cuprous iodide (242.3 mg, 0.02 eq.) triethylamine (1.5 eq.) are placed in a sealed tube and anhydrous THF (176 mL) is added under the protection of nitrogen. The reaction mixture is reacted for 48 hours at 60° C. The reaction mixture is extracted with ethyl acetate after the reaction is monitored to be complete, dried with anhydrous sodium sulfate, concentrated, and separated by column chromatography to obtain Compound I-1-2 (6.61 g, yield 32%).

Step two: Synthesis of Compound I-1-3

Compound I-1-2 (6.30 g, 19.6 mmol), TBAF (25.63 g, 98.0 mmol, 5.0 eq.) are dissolved in 2 mL THF. The reaction mixture is reacted overnight at 70° C.. The reaction mixture is extracted with ethyl acetate after the reaction is monitored to be complete, dried with anhydrous sodium sulfate, concentrated, and separated by column chromatography to obtain compound I-1-3 (8.50 g, crude).

Step three: Synthesis of Compound I-1-4

I-1-3 (8.50 g, 26.3 mmol) is dissolved in 2.0 mL of dioxane at the room temperature. Hydrochloric acid (0.76 mL) is slowly added. The reaction mixture is reacted for 20 minutes. The reaction mixture is extracted with EA after the reaction is monitored to be complete, dried and concentrated to obtain compound I-1-4 (3.10 g, yield 63% in two steps).

Step four: Synthesis of Compound I-1-5

I-1-4 (3.10 g, 12.4 mmol) is dissolved in 1.0 mL of DMF at the room temperature and potassium bisulfate (760.0 mg, 5.58 mmol, 0.45 eq.) is added. The reaction mixture is reacted for 6 hours. The reaction mixture is monitored by TLC plate until the conversion of raw material is completed, extracted with ethyl acetate, dried with anhydrous sodium sulfate, concentrated, and separated by column chromatography to obtain compound I-1-5 (5.20 g, crude).

Step five: Synthesis of Compound I-1-6

Compound I-1-5 (5.20 g, 19.6 mmol), HBTU (7.43 g, 19.6 mmol, 1.0 eq.) and DIPEA (7.60 g, 58.8 mmol, 3.0 eq.) are added to a sealed tube. DMF (1.7 mL) is added under the protection of nitrogen and the reaction mixture is reacted for 30 minutes. The reaction mixture is monitored by TLC plate until the conversion of raw material is completed, extracted with ethyl acetate, dried with anhydrous sodium sulfate, concentrated, separated by column chromatography to obtain compound I-1-6 (1.50 g, yield 31% in two steps).

Example 1

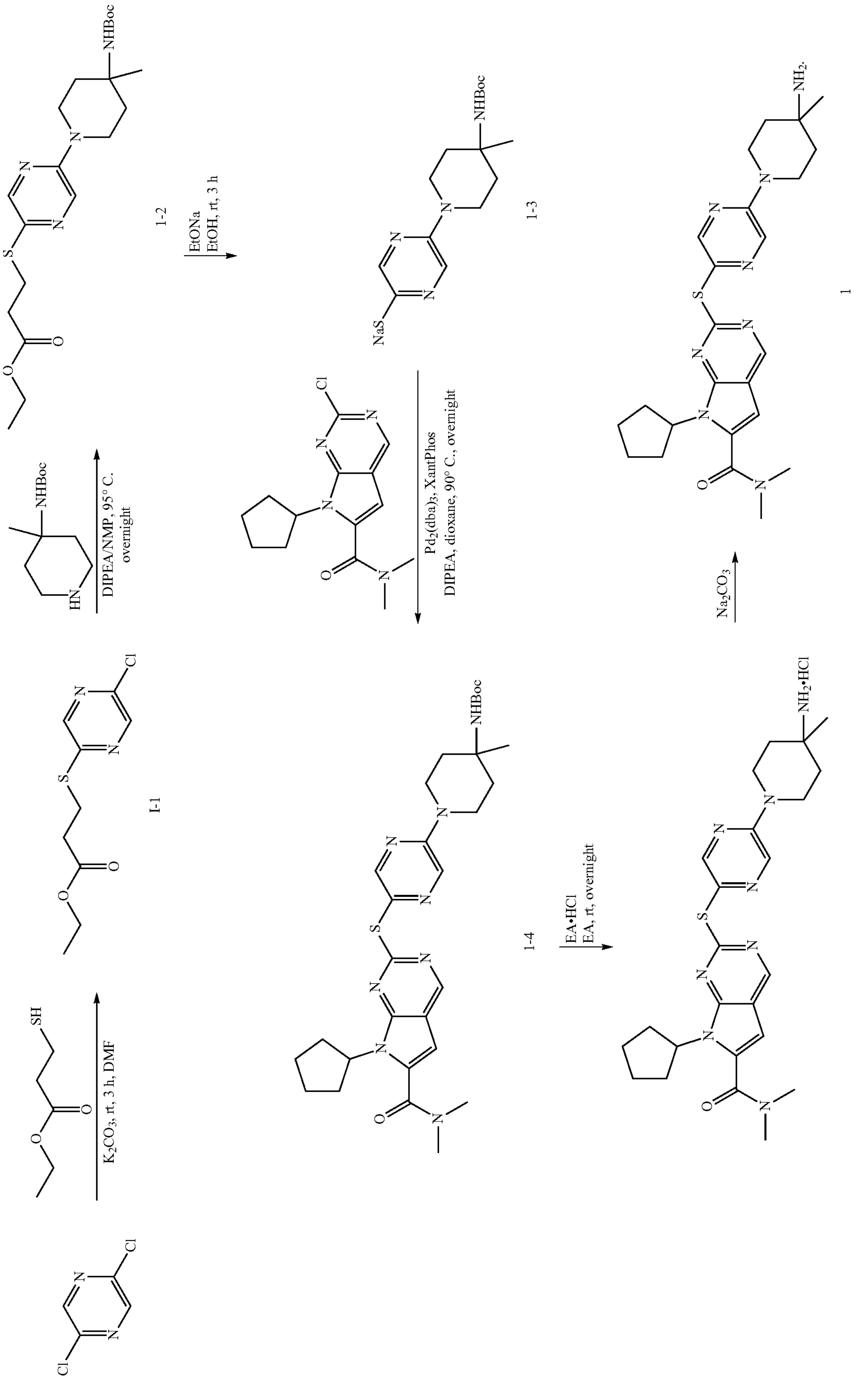
I-1
1-2
1-3
1-4
1

Step One: Synthesis of Compound 1-1

The compound 2,5-dichloropyrazine (1.50 g, 10.08 mmol), ethyl 3-mercaptopropionate (1.35 g, 10.08 mmol, 1.0 eq.) and potassium carbonate (1.53 g, 11.1 mmol, 1.1 eq.) are placed in a 50 mL single-necked flask and DMF (15 mL) is added. The reaction mixture is reacted for 3 hours. The reaction mixture is monitored by TLC plate until the conversion of raw material is completed. Ethyl acetate is added and the reaction mixture is washed a plurality of times with saturated sodium chloride aqueous solution. The organic phase is concentrated, separated by column chromatography to obtain compound 1-1 (2.51 g, yield 76%).

Step Two: Synthesis of Compound 1-2

Intermediate 1-1 (1.82 g, 7.37 mmol), 4-methyl-4-(N-tert-butoxycarbonyl) aminopiperidine (1.74 g, 8.1 mmol, 1.1 eq.) are dissolved in NMP. The reaction mixture is stirred overnight at 95° C. The reaction mixture is diluted with ethyl acetate after the reaction is monitored to be complete, washed with saturated brine water for 5 times. The organic phase is concentrated, separated by column chromatography to obtain compound 1-2 (969.2 mg, yield 31%).

Step Three: Synthesis of Compound 1-3

1-2 (969.2 mg, 2.28 mmol) is dissolved in ethanol and sodium ethoxide (170.8 mg, 2.51 mmol, 1.1 eq.) is added in batches. The reaction mixture is detected at the room temperature until the reaction of the raw materials is completed, filtrated to obtain solid compound 1-3 (674.1 mg, yield 85%).

Step Four: Synthesis of Compound 1-4

Intermediate I-1 (99.6 mg, 0.34 mmol), compound 1-3 (118.3 mg, 0.34 mmol), $Pd_2(dba)_3$ (6.2 mg, 2 mol %), XantPhos (23.1 mg, 4 mol %), DIPEA (87.9 mg, 0.68 mmol, 2.0 eq.) are placed in a sealed tube. Anhydrous dioxane (2 mL) is added under a protection of nitrogen. The reaction mixture is reacted overnight at 90° C. The reaction mixture is extracted with ethyl acetate after the reaction is monitored to be complete, dried with anhydrous sodium sulfate, concentrated, and separated by column chromatography to obtain compound 1-4 (40.4 mg, yield 21%).

Step Five: Synthesis of Compound 1

Compound 1-4 (20.2 mg, 0.035 mmol) is dissolved in EA (1 mL) and EA/HCl (1 mL) is added. The reaction mixture is reacted overnight at the room temperature. The reaction mixture is adjusted on a pH value to be alkaline through adding sodium carbonate solution after the reaction is monitored to be complete, extracted with EA, and dried and concentrated to obtain compound 1 (14.2 mg, yield 87%). $^1H$ NMR (300 MHz, Chloroform-d) δ 8.75 (s, 1H), 8.35 (d, J=1.4 Hz, 1H), 8.21 (d, J=1.4 Hz, 1H), 6.43 (s, 1H), 4.56 (p, J=8.8 Hz, 1H), 3.85-3.63 (m, 4H), 3.10 (d, J=17.1 Hz, 6H), 2.26-2.10 (m, 2H), 1.94-1.83 (m, 2H), 1.73-1.40 (m, 8H), 1.24 (s, 3H).

Example 2

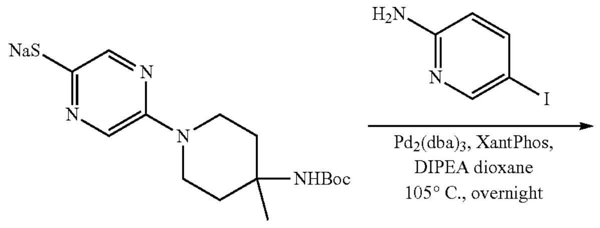

1-3

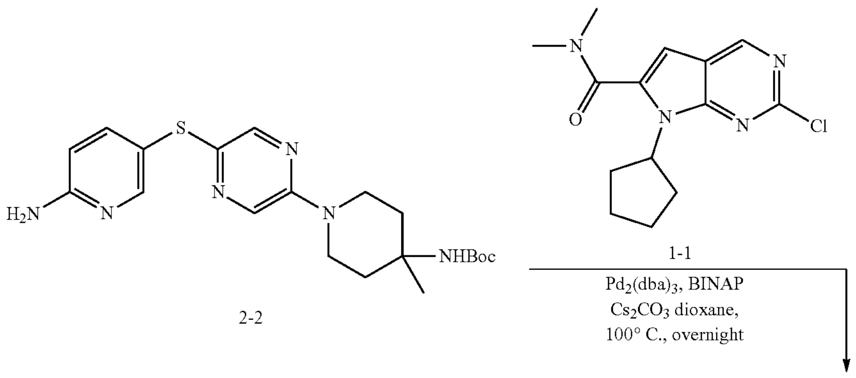

2-2

1-1

-continued

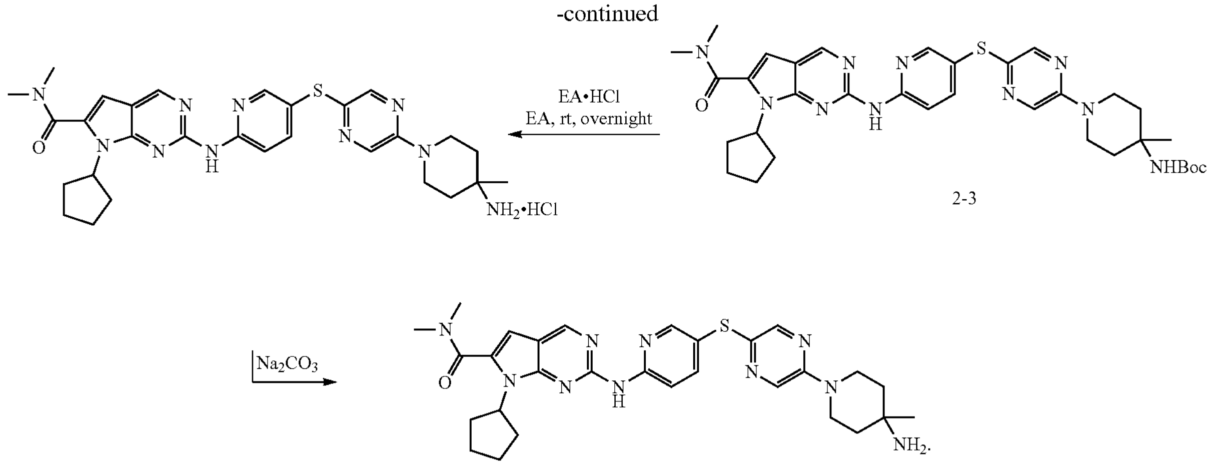

2-3

2

Step One: Synthesis of Compound 2-2

Compounds 1-3 (240.0 mg, 0.69 mmol), 2-amino-5-iodopyridine (151.8 mg, 0.69 mmol, 1.0 eq.) and $Pd_2(dba)_3$ (12.6 mg, 2 mol %), XantPhos (16.0 mg, 4 mol %) and DIPEA (178.4 mg, 1.4 mmol, 2.0 eq) are placed in a sealed tube. Anhydrous dioxane (3 mL) is added under a protection of nitrogen. The reaction mixture is reacted overnight at 105° C. The reaction mixture is extracted with ethyl acetate after the reaction is monitored to be complete, dried with anhydrous sodium sulfate, concentrated and separated by column chromatography to obtain compound 2-2 (49.8 mg, yield 17%).

Step two: Synthesis of Compound 2-3

Compound2-2 (89.9 mg, 0.22 mmol), intermediate I-1 (70.3 mg, 0.24 mmol, 1.1 eq.) $Pd_2(dba)_3$ (4.0 mg, 2 mol %), BINAP (8.2 mg, 6 mol %) and DIPEA (178.4 mg, 1.4 mmol, 2.0 eq) are placed in a sealed tube. Anhydrous dioxane (1 mL) is added under a protection of nitrogen. The reaction mixture is reacted overnight at 105° C. The reaction mixture is extracted with ethyl acetate after the reaction is monitored to be complete, dried with anhydrous sodium sulfate, concentrated and separated by column chromatography to obtain compound 2-3 (90.2 mg, yield 61%).

Step Three: Synthesis of Compound 2

Compound 2-3 (62.0 mg, 0.09 mmol) is dissolved in EA (1 mL) and EA/HCl (1 mL) is added. The reaction mixture is reacted overnight at the room temperature. The reaction mixture is adjusted on a pH value to be alkaline through adding sodium carbonate solution after the reaction is monitored to be complete, extracted with EA, dried and concentrated to obtain compound 2-4 (35.2 mg, yield 68%). $^1$H NMR (300 MHz, Chloroform-d) δ 8.72 (s, 1H), 8.49 (d, J=8.8 Hz, 1H), 8.41 (d, J=2.3 Hz, 1H), 8.07 (d, J=1.4 Hz, 2H), 8.04 (d, J=1.4 Hz, 1H), 7.83 (dd, J=8.8, 2.3 Hz, 1H), 6.46 (s, 1H), 4.79 (p, J=9.4 Hz, 1H), 3.71-3.52 (m, 4H), 3.16 (s, 6H), 2.64-2.47 (m, 2H), 2.16-1.96 (m, 4H), 1.77-1.69 (m, 2H), 1.69-1.46 (m, 4H), 1.20 (s, 3H).

Example 3

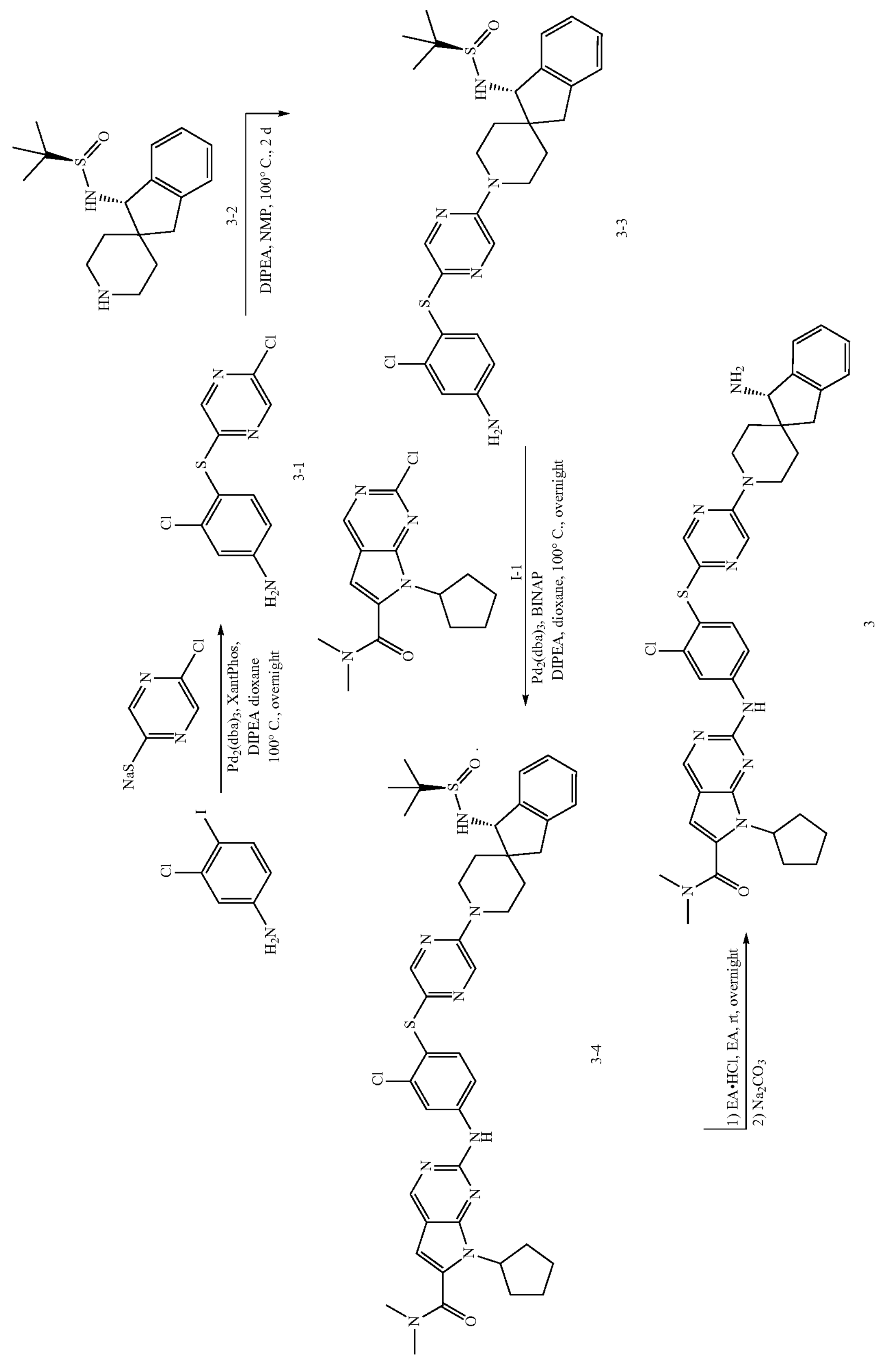
Pd$_2$(dba)$_3$, XantPhos,
DIPEA dioxane
100° C., overnight
3-1
3-2
DIPEA, NMP, 100° C., 2 d
3-3
I-1
Pd$_2$(dba)$_3$, BINAP
DIPEA, dioxane, 100° C., overnight
3-4
1) EA•HCl, EA, rt, overnight
2) Na$_2$CO$_3$
3

Step one: Synthesis of Compound 3-1

The compound 3-chloro-4-iodoaniline (700.0 mg, 2.8 mmol), 5-chloro-2-pyrazin sulfide sodium (472.1 mg, 2.8 mmol, 1.0 eq.) $Pd_2(dba)_3$ (18.3 mg, 2 mol %), XantPhos (23.1 mg, 4 mol %) and DIPEA (724.1 mg, 5.6 mmol, 2.0 eq) are placed in a sealed tube. Anhydrous dioxane (10 mL) is added under a protection nitrogen. The reaction mixture is reacted overnight at 100° C. The reaction mixture is extracted with ethyl acetate after the reaction is monitored to be complete, dried with anhydrous sodium sulfate, concentrated and separated by column chromatography to obtain compound 3-1 (226.1 mg, yield 30%).

Step Two: Synthesis of Compound 3-3

Compound 3-1 (150.0 mg, 0.55 mmol) and compound 3-2 (337.2 mg, 1.1 mmol, 2.0 eq.) are dissolved in NMP, stirred overnight at 100° C. The reaction mixture is diluted with ethyl acetate after the reaction is monitored to be complete, washed with saturated brine water for 5 times. The organic phase is concentrated, separated by column chromatography to obtain compound 3-3 (116.6 mg, yield 39%).

Step three: Synthesis of Compound 3-4

Compound 3-4 (100.0 mg, 0.18 mmol), intermediate I-1 (1.1 eq.), $Pd_2(dba)_3$ (18.3 mg, 2 mol %), BINAP (6.7 mg, 6 mol %) and DIPEA (46.5 mg, 0.36 mmol, 2.0 eq) are placed in a sealed tube. Anhydrous dioxane (1 mL) is added under a protection of nitrogen. The reaction mixture is reacted overnight at 100° C. The reaction mixture is extracted with ethyl acetate after the reaction is monitored to be complete, dried with anhydrous sodium sulfate, concentrated, and separated by column chromatography to obtain compound 3-4 (67.0 mg, yield 47%).

Step Four: Synthesis of Compound 3

Compound 3-4 (60.0 mg, 0.075 mmol) is dissolved in EA (1 mL) and EA/HCl (1 mL) is added. The reaction mixture is reacted overnight at the room temperature. The reaction mixture is adjusted on a pH value to be alkaline through adding sodium carbonate solution after the reaction is monitored to be complete, extracted with EA, and dried and concentrated to obtain compound 3 (42.2 mg, yield 81%). $^1$H NMR (300 MHz, Chloroform-d) δ 8.65 (s, 1H), 8.25 (d, J=2.3 Hz, 1H), 8.11 (d, J=1.4 Hz, 1H), 8.08 (d, J=1.4 Hz, 1H), 7.37-7.27 (m, 3H), 7.25-7.18 (m, 4H), 6.44 (s, 1H), 4.74 (p, J=9.2 Hz, 1H), 4.21-4.09 (m, 2H), 3.98 (s, 1H), 3.27-3.13 (m, 8H), 3.08 (d, J=15.7 Hz, 1H), 2.72 (d, J=15.7 Hz, 1H), 2.67-2.52 (m, 2H), 2.17-2.00 (m, 4H), 1.91-1.62 (m, 5H), 1.42-1.33 (m, 1H).

Example 4

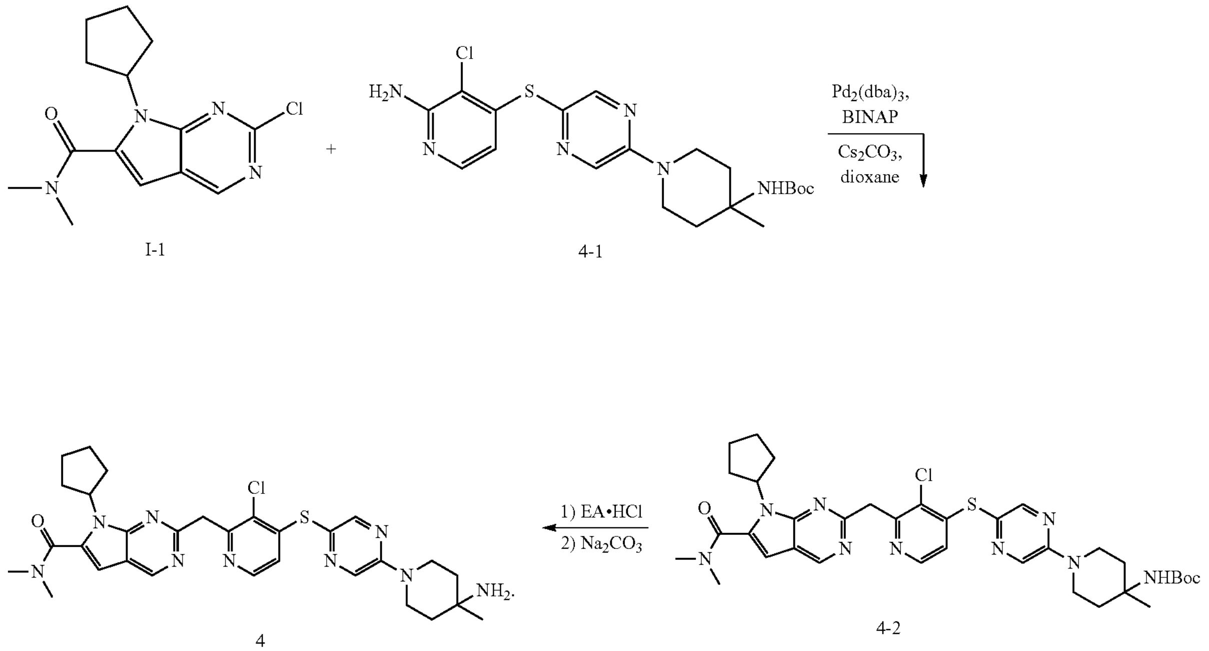

I-1 4-1 4 4-2

Step One: Synthesis of Compound 4-2

Compound 4-1 (100.0 mg, 0.22 mmol), intermediate I-1 (67.6 mg, 0.23 mmol, 1.05 eq.) $Pd_2(dba)_3$ (36.6 mg, 4 mol %), BINAP(74.7 mg, 12 mol %) and $Cs_2CO_3$ (143.4 mg, 0.44 mmol, 2.0 eq) are placed in a sealed tube. Anhydrous dioxane (1 mL) is added under a protection of nitrogen. The reaction mixture is reacted overnight at 100° C. The reaction mixture is extracted with ethyl acetate after the reaction is monitored to be complete, dried with anhydrous sodium sulfate, concentrated and separated by column chromatography to obtain compound 4-2 (41.0 mg, yield 26%).

Step Two: Synthesis of Compound 4

Compound 4-2 (41.0 mg, 0.060 mmol) is dissolved in EA (1 mL) and EA/HCl (1 mL) is added. The reaction mixture is reacted overnight at the room temperature. The reaction mixture is adjusted on a pH value to be alkaline through adding sodium carbonate solution after the reaction is monitored to be complete, extracted with EA, and dried and concentrated to obtain compound 4 (21.0 mg, yield 60%). $^1$H NMR (300 MHz, Chloroform-d) δ 8.81 (s, 1H), 8.31 (d, J=1.4 Hz, 1H), 8.27 (d, J=1.4 Hz, 1H), 8.06 (d, J=5.4 Hz, 1H), 7.74 (s, 1H), 6.47 (s, 1H), 6.35 (d, J=5.4 Hz, 1H), 4.78 (p, J=8.7 Hz, 1H), 3.92-3.80 (m, 2H), 3.78-3.65 (m, 2H), 3.17 (s, 3H), 3.14 (s, 3H), 2.53-2.36 (m, 2H), 2.14-1.92 (m, 4H), 1.76-1.59 (m, 6H), 1.27 (s, 3H).

Example 5

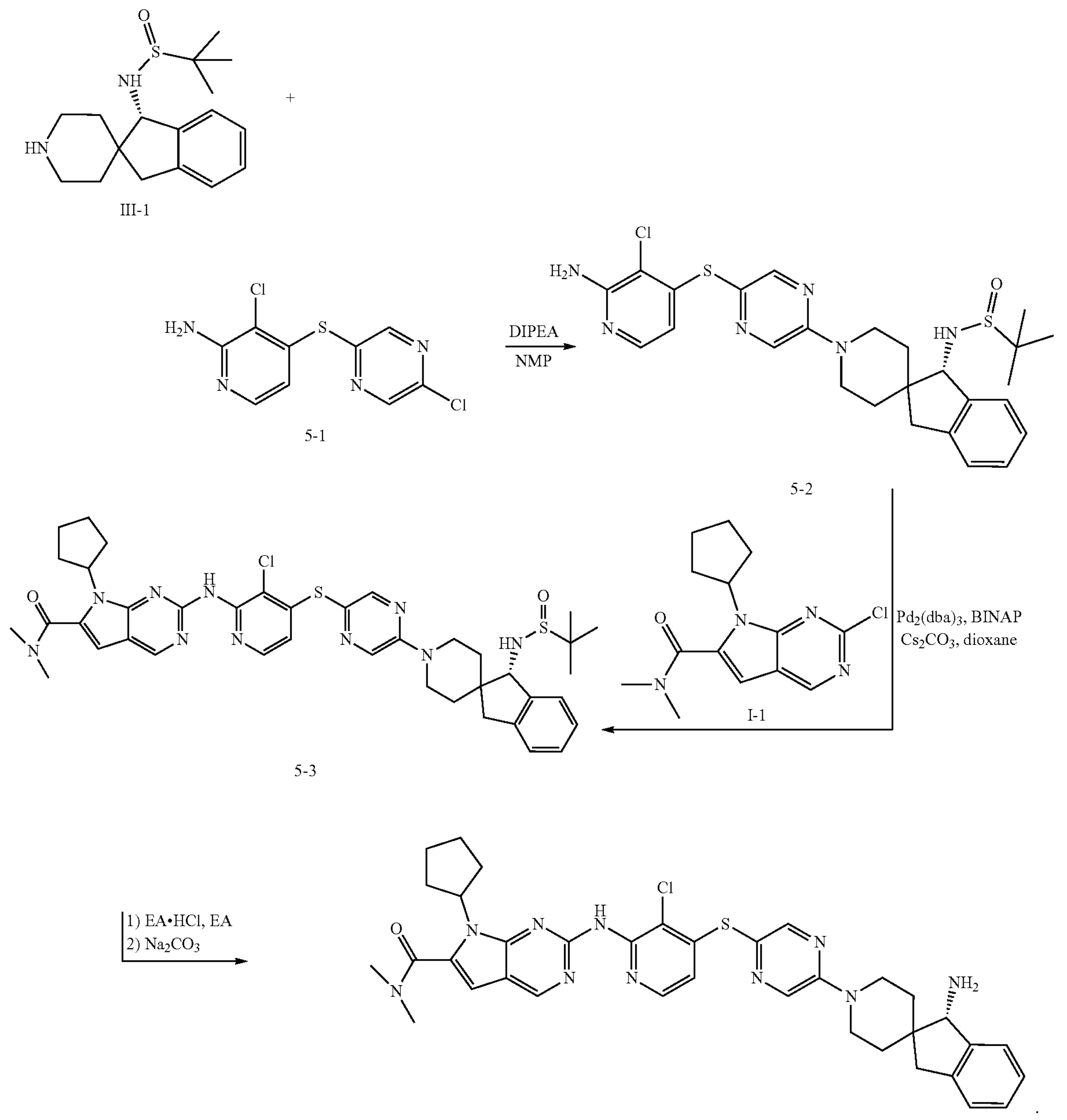

III-1

5-1

5-2

I-1

5-3

5

Step One: Synthesis of Compound 5-2

Intermediate III-1 (300.0 mg, 1.10 mmol) and compound 5-1 (450.6 mg, 1.65 mmol, 1.5 eq.) are dissolved in NMP. DIPEA (10 mL) is added. The reaction mixture is stirred overnight at 100° C. The reaction mixture is diluted with ethyl acetate after the reaction is monitored to be complete, washed with saturated brine water for 5 times. The organic phase is concentrated, separated by column chromatography to obtain compound 5-2 (444.0 mg, yield 74%).

Step Two: Synthesis of Compound 5-3

Compound 5-2 (150.0 mg, 0.28 mmol), intermediate I-1 (84.9 mg, 0.29 mmol, 1.05 eq.), $Pd_2(dba)_3$ (10.3 mg, 4 mol %), BINAP (20.9 mg, 12 mol %) and $Cs_2CO_3$ (182.4 mg, 0.56 mmol, 2.0 eq) are placed in a sealed tube. Dioxane (1 mL) is added under a protection of nitrogen. The reaction mixture is reacted overnight at 100° C. The reaction mixture is extracted with ethyl acetate after the reaction is monitored to be complete, dried with anhydrous sodium sulfate, concentrated, and separated by column chromatography to obtain compound 5-3.

Step Three: Synthesis of Compound 5

Compound 5-3 is dissolved in EA (1 mL) and EA·HCl (1 mL) is added. The reaction mixture is reacted overnight at the room temperature. The reaction mixture is adjusted on a pH value to be alkaline through adding sodium carbonate solution after the reaction is monitored to be complete, extracted with DCM/MeOH (5:1), and dried and concentrated to obtain compound 5 (29.0 mg, 20% yield). $^1H$ NMR (300 MHz, Chloroform-d) δ 8.79 (s, 1H), 8.30 (d, J=1.2 Hz, 1H), 8.27 (d, J=1.2 Hz, 1H), 8.05 (d, J=5.4 Hz, 1H), 7.74 (s, 1H), 7.38-7.31 (m, 1H), 7.26-7.20 (m, 3H), 6.45 (s, 1H), 6.35 (d, J=5.4 Hz, 1H), 4.76 (p, J=8.8 Hz, 1H), 4.38-4.19 (m, 2H), 4.02 (s, 1H), 3.38-3.22 (m, 2H), 3.20-3.06 (m, 7H), 2.77 (d, J=15.7 Hz, 1H), 2.54-2.36 (m, 2H), 2.13-1.75 (m, 9H), 1.48-1.38 (m, 1H).

Examples 6 and 7

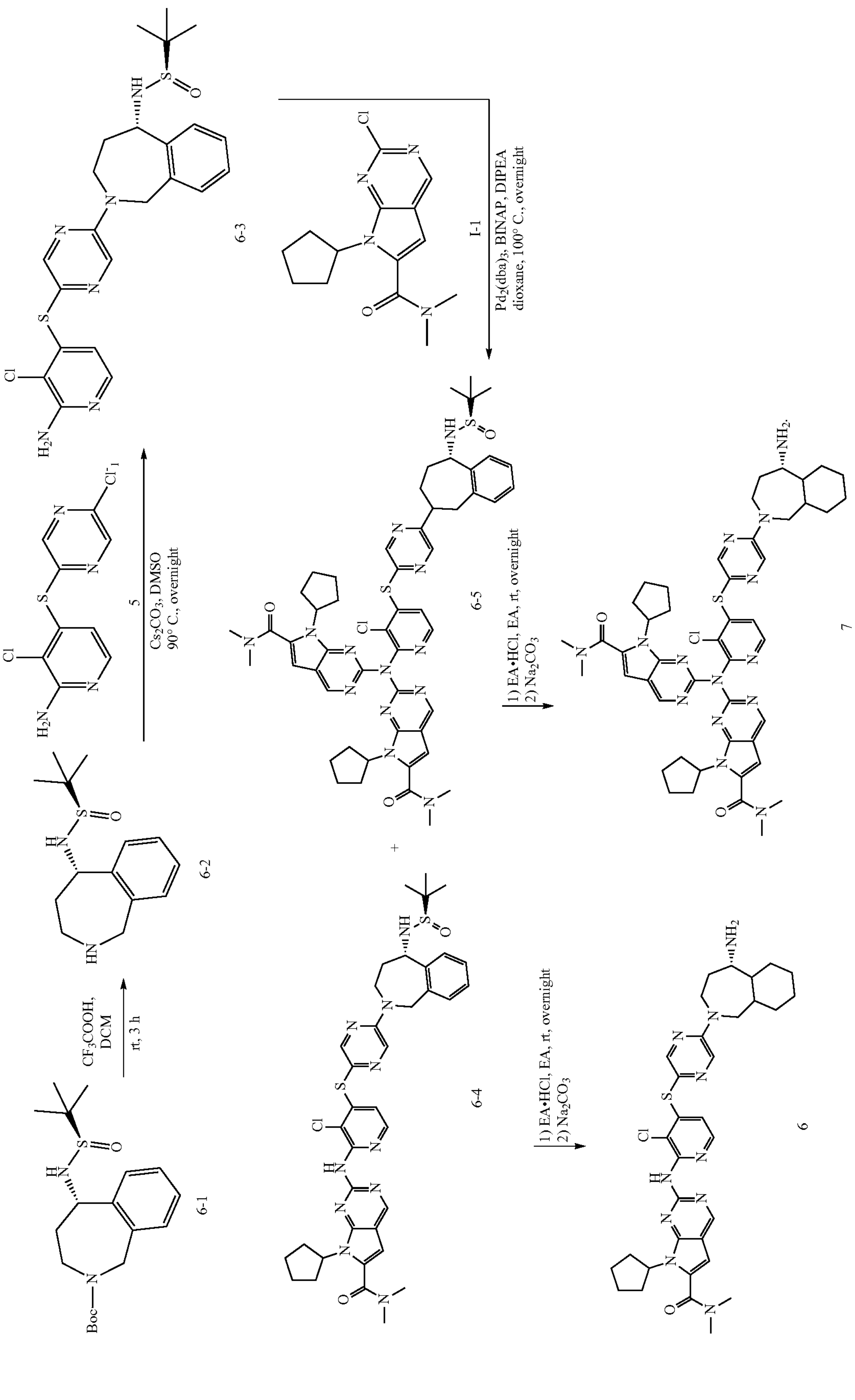
6-1 6-2 6-3 6-4 6-5 6 7

Step One: Synthesis of Compound 6-2

Compound 6-1 (191.0 mg, 0.66 mmol) is dissolved in DCM (3 mL) and trifluoroacetic acid (1 mL) is added. The reaction mixture is reacted at the room temperature for 3 hours. The reaction mixture is adjusted on a pH value to be alkaline through adding sodium carbonate solution after the reaction is monitored to be complete, extracted with DCM/MeOH (5:1), and dried and concentrated to obtain compound 6-2 (137.1 mg).

Step Two: Synthesis of Compound 6-3

Compound 6-2 (137.1 mg, 0.51 mmol), intermediate 5-1 (120.9 mg, 0.51 mmol, 1.0 eq.) and cesium carbonate (498.5 mg, 1.53 mmol, 3.0 eq.) are dissolved in DMSO (3 mL) and stirred overnight at 90° C. The reaction mixture is diluted with ethyl acetate after the reaction is monitored to be complete, washed with saturated brine water for 5 times. The organic phase is concentrated, separated by column chromatography to obtain compound 6-3 (66.7 mg, yield 20%).

Step Three: Synthesis of Compound 6-4, Compound 6-5

Compound 6-3 (66.7 mg, 0.13 mmol), intermediate I-1 (58.6 mg, 0.20 mmol, 1.5 eq.) $Pd_2(dba)_3$ (2.4 mg, 2 mol %), BINAP (4.9 mg, 6 mol %) and DIPEA (33.6 mg, 0.26 mmol, 2.0 eq) are placed in a sealed tube. Anhydrous dioxane (1 mL) is added under a protection of nitrogen. The reaction mixture is reacted overnight at 100° C. The reaction mixture is extracted with ethyl acetate after the reaction is monitored to be complete, dried with anhydrous sodium sulfate, concentrated, and separated by column chromatography to obtain compound 6-4 (24.6 mg, yield 24%), compound 6-5 (18.9 mg).

Step four: Synthesis of Compound 6, Compound 7

Compound 6-4 (24.6 mg, 0.032 mmol) is dissolved in EA (1 mL) and EA·HCl (1 mL) is added. The reaction mixture is reacted overnight at the room temperature. The reaction mixture is adjusted on a pH value to be alkaline through adding sodium carbonate solution after the reaction is monitored to be complete, extracted with DCM/MeOH (5:1), dried and concentrated to obtain compound 6 (14.5 mg, 68% yield). $^1$H NMR (300 MHz, Chloroform-d) δ 8.78 (s, 1H), 8.26 (d, J=1.4 Hz, 1H), 8.24 (d, J=1.4 Hz, 1H), 8.02 (d, J=5.5 Hz, 2H), 7.46-7.21 (m, 4H), 6.46 (s, 1H), 6.35 (d, J=5.5 Hz, 2H), 5.05 (d, J=15.2 Hz, 1H), 4.86-4.67 (m, 2H), 4.49-4.40 (m, 1H), 4.27-4.03 (m, 2H), 3.14 (s, 3H), 3.12 (s, 3H), 2.53-2.33 (m, 2H), 2.31-2.16 (m, 1H), 2.04-1.86 (m, 5H), 1.71-1.48 (m, 2H).

Compound 6-5 (18.9 mg, 0.019 mmol) is reacted according to the above procedure to obtain compound 7 (11.4 mg, yield 70%). $^1$H NMR (300 MHz, Chloroform-d) δ 8.85 (s, 2H), 8.25 (s, 2H), 8.11 (d, J=5.3 Hz, 1H), 7.45-7.36 (m, 2H), 7.33-7.18 (m, 2H), 6.60 (d, J=5.3 Hz, 1H), 6.46 (s, 2H), 5.05 (d, J=15.1 Hz, 1H), 4.74 (d, J=15.1 Hz, 1H), 4.69-4.59 (m, 2H), 4.54-4.44 (m, 1H), 4.21-4.06 (m, 2H), 3.21-2.98 (m, 12H), 2.30-2.07 (m, 6H), 2.02-1.82 (m, 6H), 1.51-1.27 (m, 6H).

Example 8

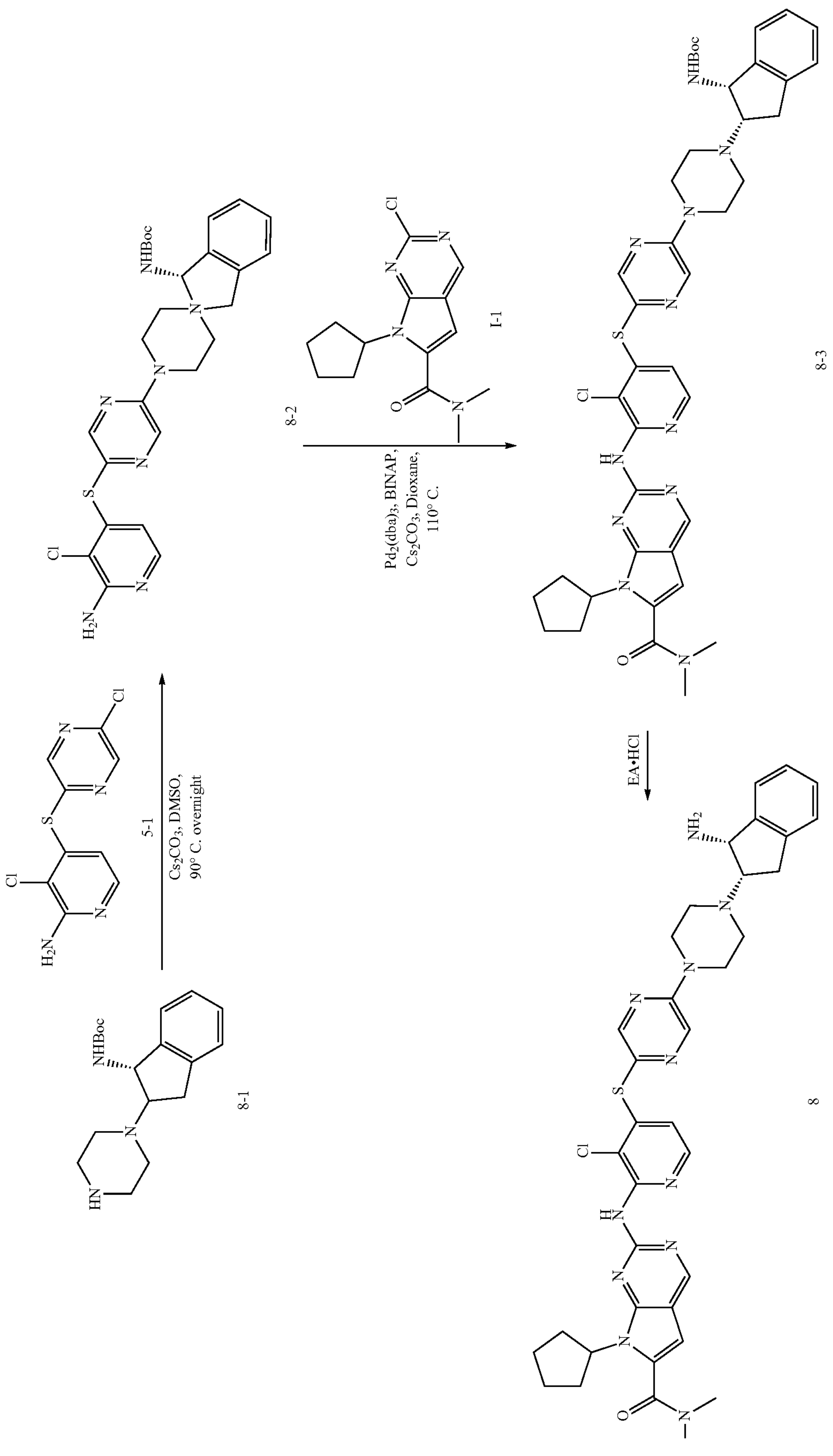
8-1
I-1
8-3
8

-continued
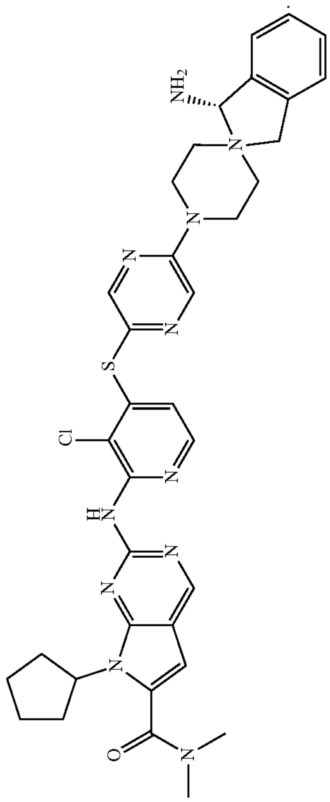
8

Step one: Synthesis of Compound 8-2

Compound 8-1 (200.0 mg, 0.63 mmol), compound 5-1 (172.0 mg, 0.63 mmol, 1.0 eq.) and cesium carbonate (310 mg, 0.95 mmol, 1.5 eq.) are dissolved in DMSO (2 mL). The reaction mixture is stirred overnight at 90° C. The reaction mixture is diluted with ethyl acetate after the reaction is monitored to be complete, washed with saturated brine water for 5 times. The organic phase is concentrated, separated by column chromatography to obtain compound 8-2 (168.1 mg, yield 50%).

Step two: Synthesis of Compound 8-3

Compound 8-2 (1500 mg, 0.27 mmol), intermediate I-1 (83.0 mg, 0.28 mmol, 1.05 eq.), $Pd_2(dba)_3$ (5 mg, 2 mol %), BINAP (11 mg, 6 mol %), $Cs_2CO_3$ (176 mg, 0.54 mmol, 2 eq) are placed in a sealed tube. Anhydrous dioxane (1 mL) is added under a protection of nitrogen. The reaction mixture is reacted overnight at 110° C.. The reaction mixture is extracted with ethyl acetate after the reaction is monitored to be complete, dried with anhydrous sodium sulfate, concentrated, and separated by column chromatography to obtain compound 8-3 (64 mg, yield 30%).

Step Three

Compound 8-3 (60 mg, 0.07 mmol) is dissolved in EA (1.0 mL) and EA·HCl (1.0 mL) is added. The reaction mixture is reacted overnight at the room temperature. The reaction mixture is adjusted on a pH value to be alkaline through adding sodium carbonate solution after the reaction is monitored to be complete, extracted with EA, dried and concentrated to obtain compound 8 (11 mg, yield 21%). $^1H$ NMR (300 MHz, Chloroform-d) δ 8.79 (s, 1H), 8.32 (d, J=1.4 Hz, 1H), 8.26 (d, J=1.4 Hz, 1H), 8.04 (d, J=5.3 Hz, 1H), 7.72 (s, 1H), 7.43-7.35 (m, 1H), 7.26-7.20 (m, 3H), 6.44 (s, 1H), 6.34 (d, J=5.3 Hz, 1H), 4.76 (p, J=8.8 Hz, 1H), 4.32 (d, J=4.8 Hz, 1H), 3.87-3.71 (m, 4H), 3.13 (s, 6H), 3.07-2.88 (m, 3H), 2.87-2.76 (m, 2H), 2.76-2.62 (m, 2H), 2.55-2.36 (m, 2H), 2.13-1.88 (m, 4H), 1.61-1.52 (m, 2H).

Example 9

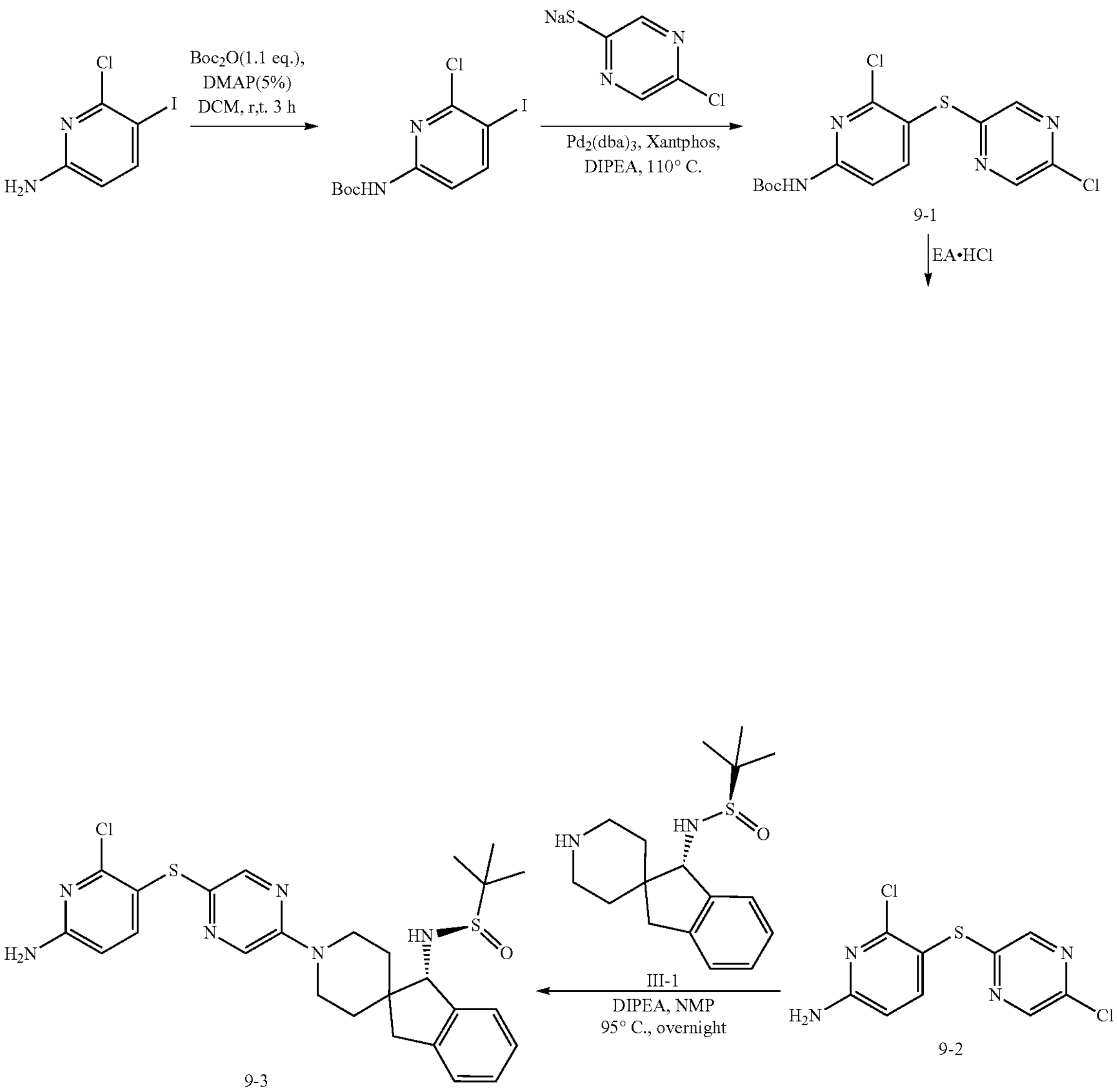

-continued

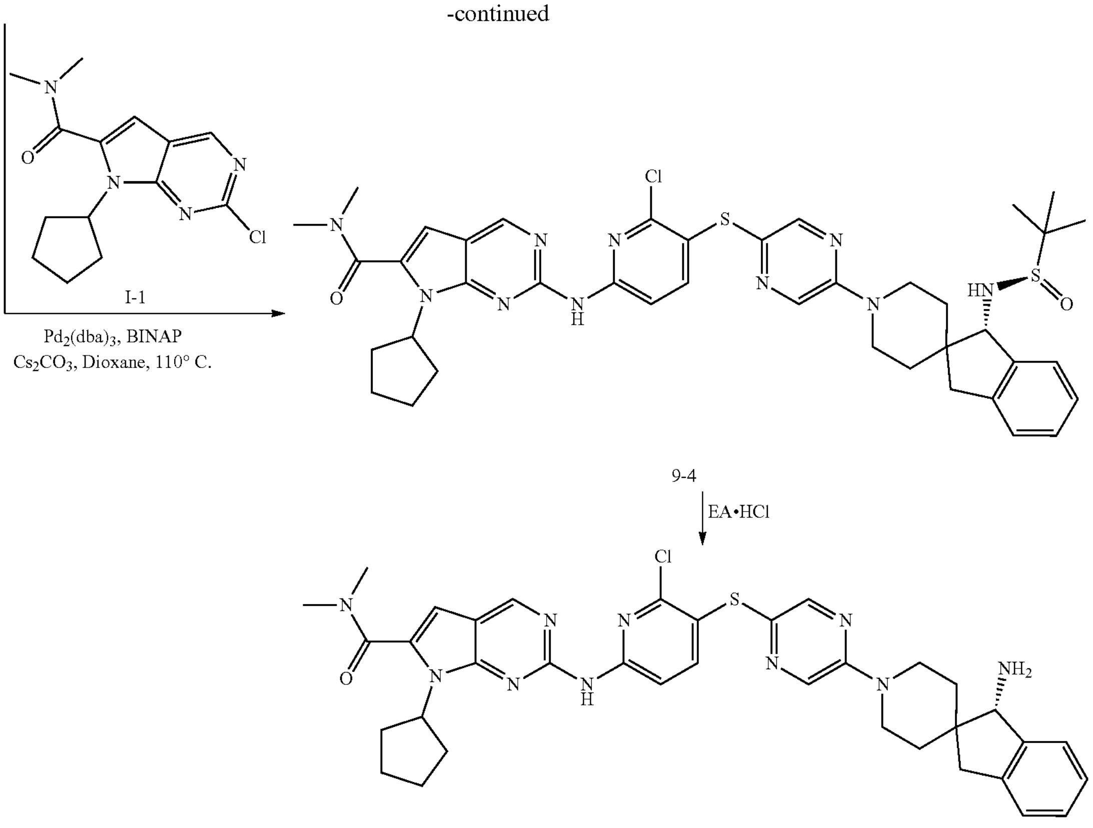

I-1

9-4

9

Step One: Synthesis of Compound 6-(N-Tert-Butoxycarbonyl)Amino-2-Chloro-3-Iodopyridine The compound 5-amino-2-chloro-3-iodopyridine (733.0 mg, 2.88 mmol) is dissolved in DCM. Triethylamine (349.1 mg, 3.46 mmol, 1.2 eq.) and DMAP (17.6 mg, 0.14 mmol, 0.05 eq.) are added. BOC anhydride (690.6 mg, 3.17 mmol, 1.1 eq.) is added at 0° C. The reaction mixture is reacted for 3 hours at the room temperature. The reaction mixture is washed with saturated aqueous sodium chloride solution for a plurality of times after the reaction is monitored to be complete. The organic phase is dried with anhydrous sodium sulfate, concentrated, and separated by column chromatography to obtain the compound 6-(N-tert-butoxycarbonyl) amino-2-chloro-3-iodopyridine (513.2 mg, yield 50%).

Step Two: Synthesis of Compound 9-1

The compound 6-(N-tert-butoxycarbonyl) amino-2-chloro-3-iodopyridine (1.28 g, 3.62 mmol), the compound 5-chloro-2-pyrazin sulfide sodium (669.0 mg, 3.98 mmol, 1.1 eq.) Pd$_2$(dba)$_3$ (66.2 mg, 2 mol %), Xantphos (125.5 mg, 6 mol %), DIPEA (934.0 mg, 7.24 mmol, 2 eq) are placed in a sealed tube. Anhydrous dioxane (1.0 mL) is added under the protection of nitrogen. The reaction mixture is reacted overnight at 110° C.. The reaction mixture is extracted with ethyl acetate after the reaction is monitored to be complete, dried with anhydrous sodium sulfate, concentrated and separated by column chromatography to obtain compound 9-1 (0.85 g, yield 65%).

Step Three: Synthesis of Compound 9-2

Compound 9-1 (0.80 g, 2.15 mmol) is dissolved in EA (1.0 mL) and EA·HCl (1.0 mL) is added. The reaction mixture is reacted overnight at the room temperature. The reaction mixture is adjusted on a pH value to be alkaline through adding sodium carbonate solution after the reaction is monitored to be complete, extracted with DCM/MeOH (5:1), dried and concentrated to obtain compound 9-2 (0.55 g, yield 94%).

Step Four: Synthesis of Compound 9-3

Intermediate III-1 (80.0 mg, 0.29 mmol), compound 9-2 (99.0 mg, 0.32 mmol, 1.0 eq.) are dissolved in 1.0 mL NMP, and DIPEA (10 mL) is added. The reaction mixture is stirred overnight at 95° C. The reaction mixture is diluted with ethyl acetate after the reaction is monitored to be complete, washed with saturated brine for 5 times. The organic phase is concentrated, separated by column chromatography to obtain compound 9-3 (128.0 mg, yield 80%).

Step five: Synthesis of Compound 9-4

Compound 9-4 (100 mg, 0.18 mmol), intermediate I-1 (56.6 mg, 0.19 mmol, 1.05 eq.) Pd$_2$(dba)$_3$ (7 mg, 2 mol %), BINAP (14 mg, 5 mol %) and cesium carbonate (120 mg, 0.37 mmol, 2.0 eq) are placed in a sealed tube. Anhydrous dioxane (2.0 mL) is added under a protection of nitrogen. The reaction mixture is reacted overnight at 110° C.. The reaction mixture is extracted with ethyl acetate after the reaction is monitored to be complete, dried with anhydrous sodium sulfate, concentrated, and separated by column chromatography to obtain compound 9-4 (53.3 mg, yield 37%).

Step Six: Synthesis of Compound 9

Compound 9-4 (33.0 mg, mmol) is dissolved in EA (1.0 mL) and EA·HCl (1.0 mL) is added. The reaction mixture is reacted overnight at the room temperature. The reaction mixture is adjusted on a pH value to be alkaline through adding sodium carbonate solution after the reaction is monitored to be complete, extracted with DCM/MeOH (5:1), dried and concentrated to obtain compound 9 (24.1 mg, 83% yield). 1H NMR (300 MHz, Chloroform-d) δ 8.83 (s, 1H), 8.45 (s, 1H), 8.42 (d, J=8.6 Hz, 1H), 8.15 (d, J=1.3 Hz, 1H), 8.09 (d, J=1.3 Hz, 1H), 7.78 (d, J=8.6 Hz, 1H), 7.39-7.29 (m, 1H), 7.26-7.17 (m, 3H), 6.48 (s, 1H), 4.79 (p, J=9.0 Hz, 1H), 4.25-4.09 (m, 2H), 3.98 (s, 1H), 3.29-3.12 (m, 8H), 3.08 (d, J=15.6 Hz, 1H), 2.73 (d, J=15.6 Hz, 1H), 2.63-2.44 (m, 2H), 2.17-1.94 (m, 4H), 1.92-1.61 (m, 5H), 1.42-1.33 (m, 1H).

Example 10

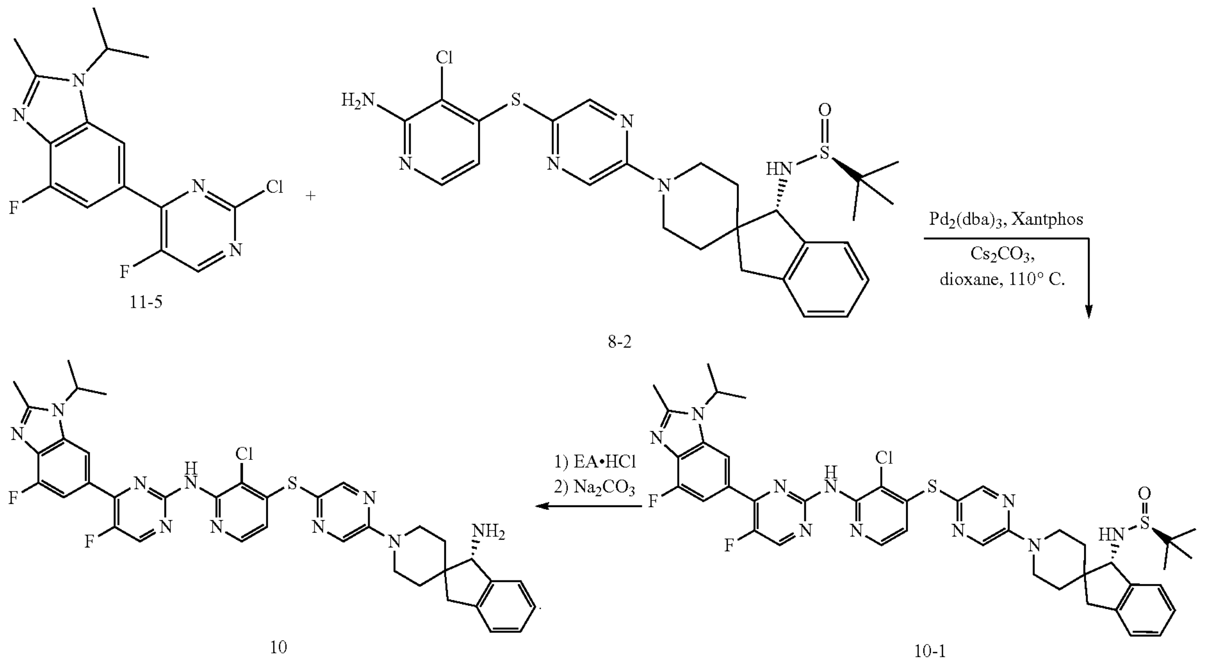

11-5

8-2

10

10-1

Step One: Synthesis of Compound 10-1

Compound 8-2 (150 mg, 0.28 mmol), compound 11-5 (98 mg, 0.3 mmol, 1.1 eq.) $Pd_2(dba)_3$ (11 mg, 4 mol %), Xantphos (22 mg, 12 mol %) and cesium carbonate (180 mg, 0.55 mmol, 2.0 eq) are placed in a sealed tube. Anhydrous dioxane (2.0 mL) is added after a protection of nitrogen. The reaction mixture is reacted overnight at 110° C. The reaction mixture is extracted with ethyl acetate after the reaction is monitored to be complete, dried with anhydrous sodium sulfate, concentrated and separated by column chromatography to obtain compound 10-1 (132 mg, yield 57%).

Step two: Synthesis of Compound 10

Compound 10-1 (102.0 mg, 0.12 mmol) is dissolved in EA (1.0 mL) and EA·HCl (1.0 mL) is added. The reaction mixture is reacted overnight at the room temperature. The reaction mixture is adjusted on a pH value to be alkaline through adding sodium carbonate solution after the reaction is monitored to be complete, extracted with DCM/MeOH (5:1), dried and concentrated to obtain compound 10 (74.7 mg, yield 57%). $^1$H NMR (300 MHz, Chloroform-d) δ 8.50 (d, J=3.7 Hz, 1H), 8.32 (d, J=1.0 Hz, 1H), 8.27 (s, 1H), 8.19 (d, J=1.0 Hz, 1H), 8.12 (d, J=5.4 Hz, 1H), 7.97 (s, 1H), 7.82 (d, J=11.9 Hz, 1H), 7.53 (d, J=6.6 Hz, 1H), 7.32 (m, 3H), 6.40 (d, J=5.4 Hz, 1H), 4.73 (p, J=7.0 Hz, 1H), 4.30-4.06 (m, 3H), 3.43-3.14 (m, 3H), 2.89 (d, J=16.2 Hz, 1H), 2.68 (s, 3H), 1.97-1.50 (m, 10H).

Example 11

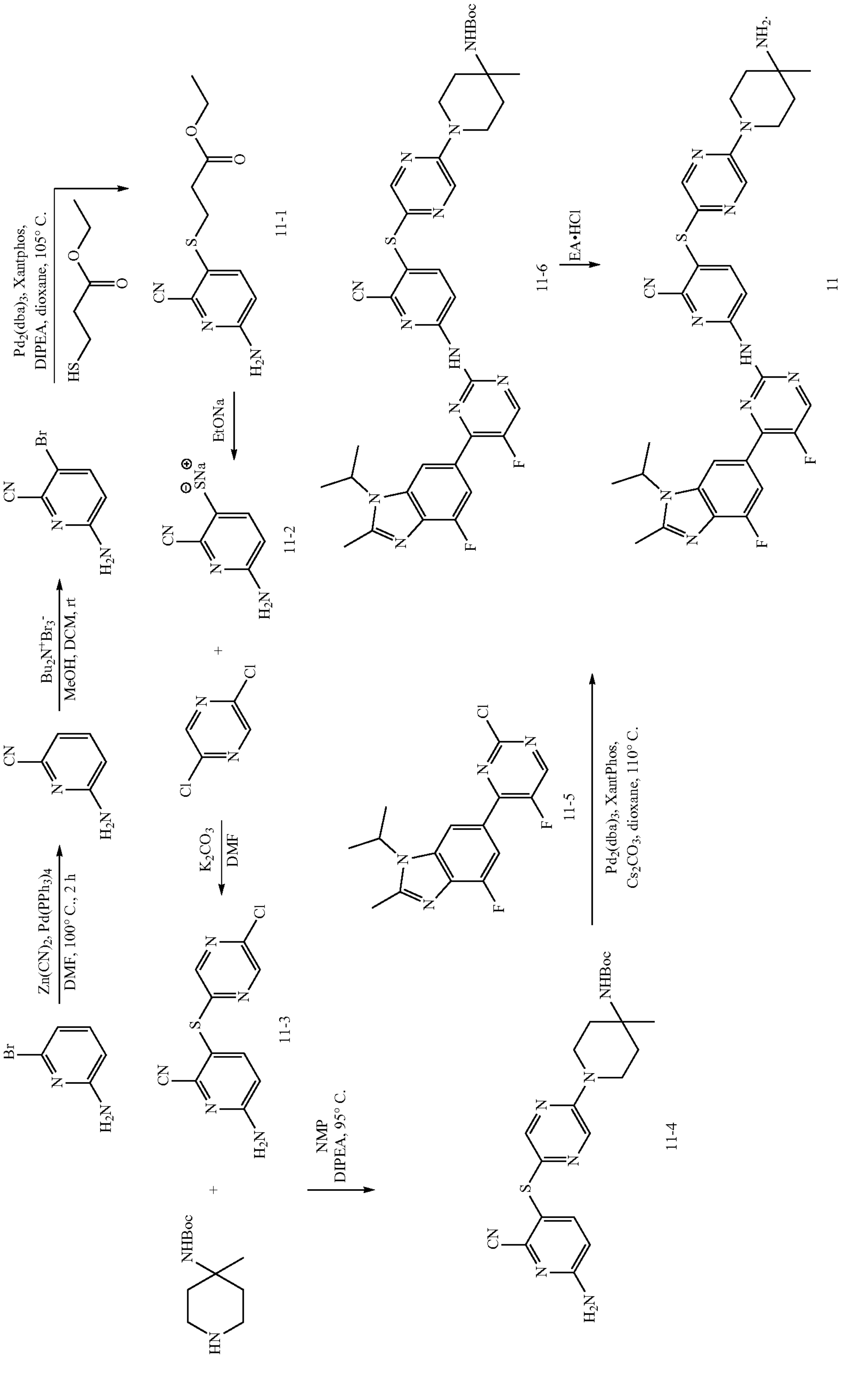
Zn(CN)$_2$, Pd(PPh$_3$)$_4$
DMF, 100° C., 2 h
$Bu_2N^+Br_3^-$
MeOH, DCM, rt
$Pd_2(dba)_3$, Xantphos,
DIPEA, dioxane, 105° C.
11-1
EtONa
11-2
$K_2CO_3$
DMF
11-3
NMP
DIPEA, 95° C.
11-4
11-5
$Pd_2(dba)_3$, XantPhos,
$Cs_2CO_3$, dioxane, 110° C.
11-6
EA•HCl
11

Step One: Synthesis of Compound 6-Amino-2-Cyanopyridine

Compound 2-bromo-6-aminopyridine (5.00 g, 28.9 mmol), zinc cyanide (3.97 g, 33.8 mmol, 1.17 eq.) and Tetrakis(triphenylphosphine) palladium (668.0 mg, 2 mol %) are placed in a 50 mL single-necked flask. DMF (mL) is added after a protection of nitrogen. The reaction mixture is reacted at 100° C. for 2 hours. The reaction mixture is extracted with ethyl acetate after the reaction is monitored to be complete, dried with anhydrous sodium sulfate, concentrated, and separated by column chromatography to obtain compound 6-amino-2-cyanopyridine (2.22 g, yield 64%).

Step Two: Synthesis of Compound 3-Bromo-6-Amino-2-Cyanopyridine

The compound 6-amino-2-cyanopyridine (2.22 g, 18.63 mmol), tetrabutylammonium tribromide (10.33 g, 21.43 mmol), methanol (15.0 mL) and DCM (15.0 mL) are placed in a 100 mL single-necked bottle. The reaction mixture is reacted overnight at the room temperature. The reaction mixture is extracted with ethyl acetate after the reaction is monitored to be complete, dried with anhydrous sodium sulfate, concentrated, and separated by column chromatography to obtain compound 3-bromo-6-amino-2-cyanopyridine (1.92 g, yield 52%).

Step Three: Synthesis of Compound 11-1

Compound 3-bromo-6-amino-2-cyanopyridine (1.92 g, 9.7 mmol), the compound 3-mercaptopropionic acid ethyl ester (3.9 g, 29.1 mmol, 3 eq.) $Pd_2(dba)_3$ (178 mg, 2 mol %), Xantphos (337 mg, 6 mol %) and DIPEA (3.4 mL, 19.4 mmol, 2.0 eq.) are placed in a sealed tube. Anhydrous dioxane (1.0 mL) is added after the protection of nitrogen. The reaction mixture is reacted overnight at 105° C. The reaction mixture is extracted with ethyl acetate after the reaction is monitored to be complete, dried with anhydrous sodium sulfate, concentrated and separated by column chromatography to obtain compound 11-1 (1.82 g, yield 75%).

Step Four: Synthesis of Compound 11-2

Compound 11-1 (1.82 g, mmol), sodium ethoxide (640 mg, 9.4 mmol, 1.3 eq.) and ethanol (mL) are placed in a 100 mL single-necked flask, reacted overnight at the room temperature. The reaction mixture is extracted with ethyl acetate after the reaction is monitored to be complete, dried with anhydrous sodium sulfate, concentrated, and separated by column chromatography to obtain Compound 11-2 (1.67 g, crude).

Step Five: Synthesis of Compound 11-3

Compound 11-2 (1.54 g, 8.9 mmol), compound 2,5-dichloropyrazine (1.3 g, 8.9 mmol, 1.0 eq.) and potassium carbonate (9.4 g, 9.8 mmol, 1.1 eq.) are dissolved in 10 mL of DMF. The reaction mixture is reacted for 12 hours at the room temperature. The reaction mixture is extracted with ethyl acetate after the reaction is monitored to be complete, dried with anhydrous sodium sulfate, concentrated, and separated by column chromatography to obtain compound 11-3 (510.0 mg, yield 22%).

Step Six: Synthesis of Compound 11-4

Compound III-3 (200.0 mg, 0.76 mmol) and tert-butyl(4-methylpiperidine)carboxamide (162.9 mg, 0.84 mmol, 1.1 eq.) are dissolved in 3.0 mL of NMP. DIPEA (8.0 mL) is added. The reaction mixture is stirred overnight at 95° C. The reaction mixture is diluted with ethyl acetate after the reaction is monitored to be complete. The organic phase is washed with saturated brine water for 5 times, separated by column chromatography to obtain compound 11-4 (254.0 mg, yield 76%).

Step Seven: Synthesis of Compound 11-5

Compound 11-4 (200.0 mg, 0.45 mmol, 0.45 eq), compound 11-5 (322.7 mg, 1.0 mmol, 1.0 eq.), $Pd_2(dba)_3$ (16.5 mg, 4 mol %), Xantphos (69.4 mg, 12 mol %) and cesium carbonate (651.6 mg, 2.0 mmol, 2.0 eq.) are placed in a sealed tube. Anhydrous dioxane (4.0 mL) is added after the protection of nitrogen. The reaction mixture is reacted overnight at 110° C. The reaction mixture is extracted with ethyl acetate after the reaction is monitored to be complete, dried with anhydrous sodium sulfate, concentrated, and separated by column chromatography to obtain compound 11-5 (70.6 mg, yield 22%).

Step Seven: Synthesis of Compound 11

Compound 11-5 (65.0 mg, 0.09 mmol) is dissolved in EA (1.0 mL) and EA·HCl (1.0 mL) is added. The reaction mixture is reacted overnight at the room temperature.

The reaction mixture is adjusted on a pH value to be alkaline through adding sodium carbonate solution after the reaction is monitored to be complete, extracted with EA, dried and concentrated to obtain compound 11 (38.0 mg, yield 67%). $^1H$ NMR (300 MHz, Chloroform-d) δ 8.65 (d, J=9.0 Hz, 1H), 8.50 (d, J=3.6 Hz, 2H), 8.24 (d, J=1.3 Hz, 1H), 8.15 (d, J=1.0 Hz, 1H), 8.07 (d, J=1.3 Hz, 1H), 7.85 (d, J=9.0 Hz, 1H), 7.75 (d, J=11.6 Hz, 1H), 4.74 (p, J=7.0 Hz, 1H), 3.78-3.55 (m, 4H), 2.70 (s, 3H), 1.72 (s, 3H), 1.69 (s, 3H), 1.68-1.47 (m, 4H), 1.21 (s, 3H).

Example 12

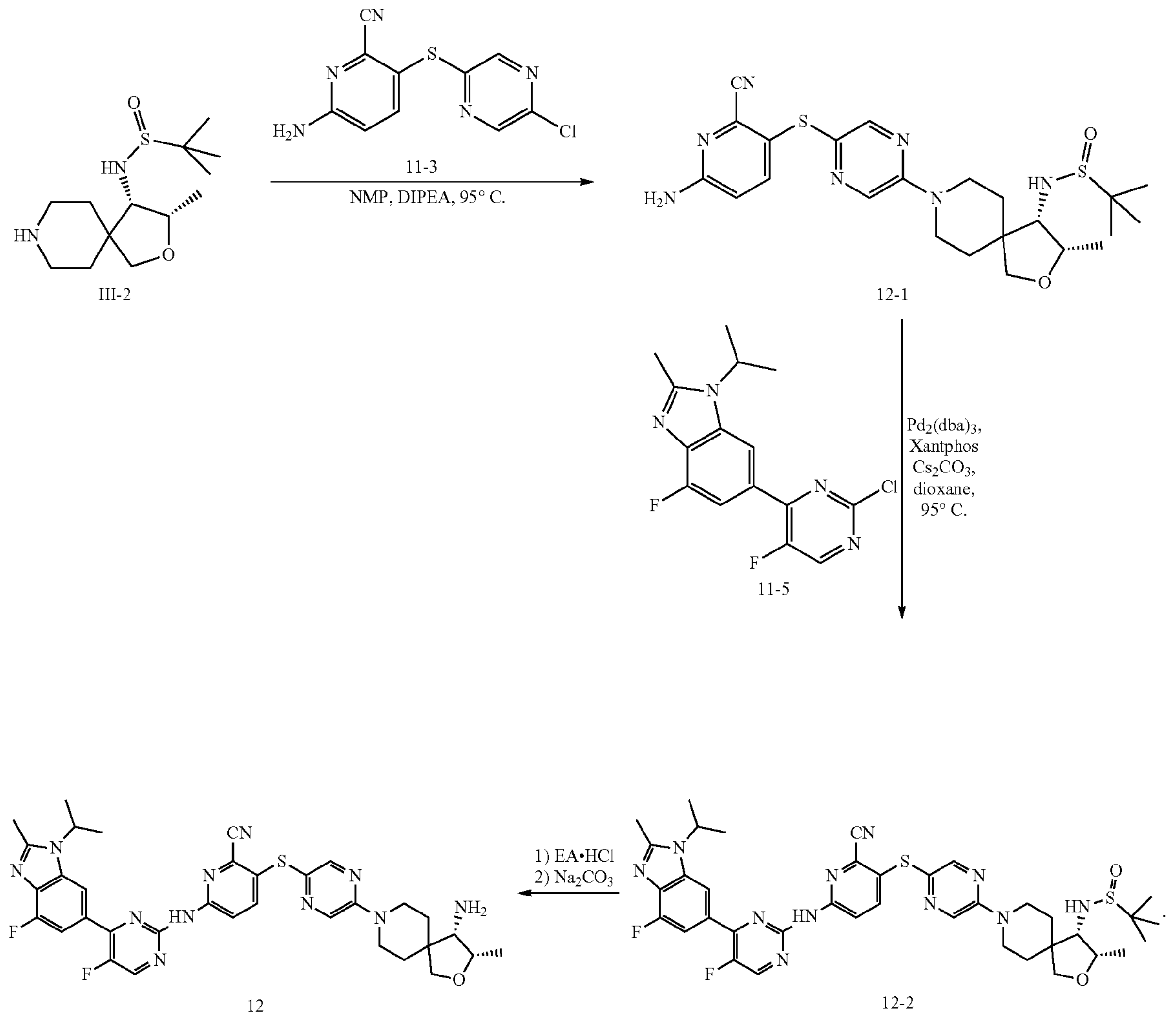

Step One: Synthesis of Compound 12-1

Intermediate III-2 (865.9 mg, 0.91 mmol, 1.2 eq.) and compound 11-3 (200.0 mg, 0.76 mmol) are dissolved in NMP (3.0 mL). DIPEA (8.0 mL) is added. The reaction mixture is stirred overnight at 95° C. The reaction mixture is diluted with ethyl acetate after the reaction is monitored to be complete, washed with saturated brine water for 5 times. The organic phase is concentrated, separated by column chromatography to obtain compound 12-1 (162.2 mg, yield 43%).

Step Two: Synthesis of Compound 12-2

Compound 12-1 (150.0 mg, 0.30 mmol), compound 11-5 (96.8 mg, 0.3 mmol, 1.0 eq.) $Pd_2(dba)_3$ (10.1 mg, 4 mol %), Xantphos (20.8 mg, 12 mol %) and cesium carbonate (195.5 mg, 0.6 mmol, 2.0 eq.) are placed in a sealed tube. Anhydrous dioxane (2.0 mL) is added after the protection of nitrogen. The reaction mixture is reacted overnight at 110° C. The reaction mixture is extracted with ethyl acetate after the reaction is monitored to be complete, dried with anhydrous sodium sulfate, concentrated, and separated by column chromatography to obtain compound 12-2 (123.0 mg, yield 52%).

Step Three: Synthesis of Compound 12

Compound 12-2 (123.0 mg, 0.16 mmol) is dissolved in EA (1 mL) and EA/HCl (2 mL) is added. The reaction mixture is reacted overnight at the room temperature. The reaction mixture is adjusted on a pH value to be alkaline through adding sodium carbonate aqueous solution after the reaction is monitored to be complete, extracted with EA, dried and concentrated to obtain compound 12 (37.1 mg, yield 64%). $^1H$ NMR (300 MHz, Chloroform-d) δ 8.65 (d, J=9.0 Hz, 1H), 8.49 (d, J=3.7 Hz, 1H), 8.43 (s, 1H), 8.24 (d, J=1.2 Hz, 1H), 8.15 (d, J=1.0 Hz, 1H), 8.06 (d, J=1.2 Hz, 1H), 7.87 (d, J=9.0 Hz, 1H), 7.75 (d, J=11.8 Hz, 1H), 4.74 (p, J=7.0 Hz, 1H), 4.24-4.13 (m, 1H), 3.96-3.75 (m, 3H), 3.68 (d, J=8.8 Hz, 1H), 3.50-3.26 (m, 2H), 2.99 (d, J=4.5 Hz, 1H), 2.70 (s, 3H), 1.93-1.80 (m, 1H), 1.77-1.64 (m, 9H), 1.23 (d, J=6.4 Hz, 3H).

Example 13

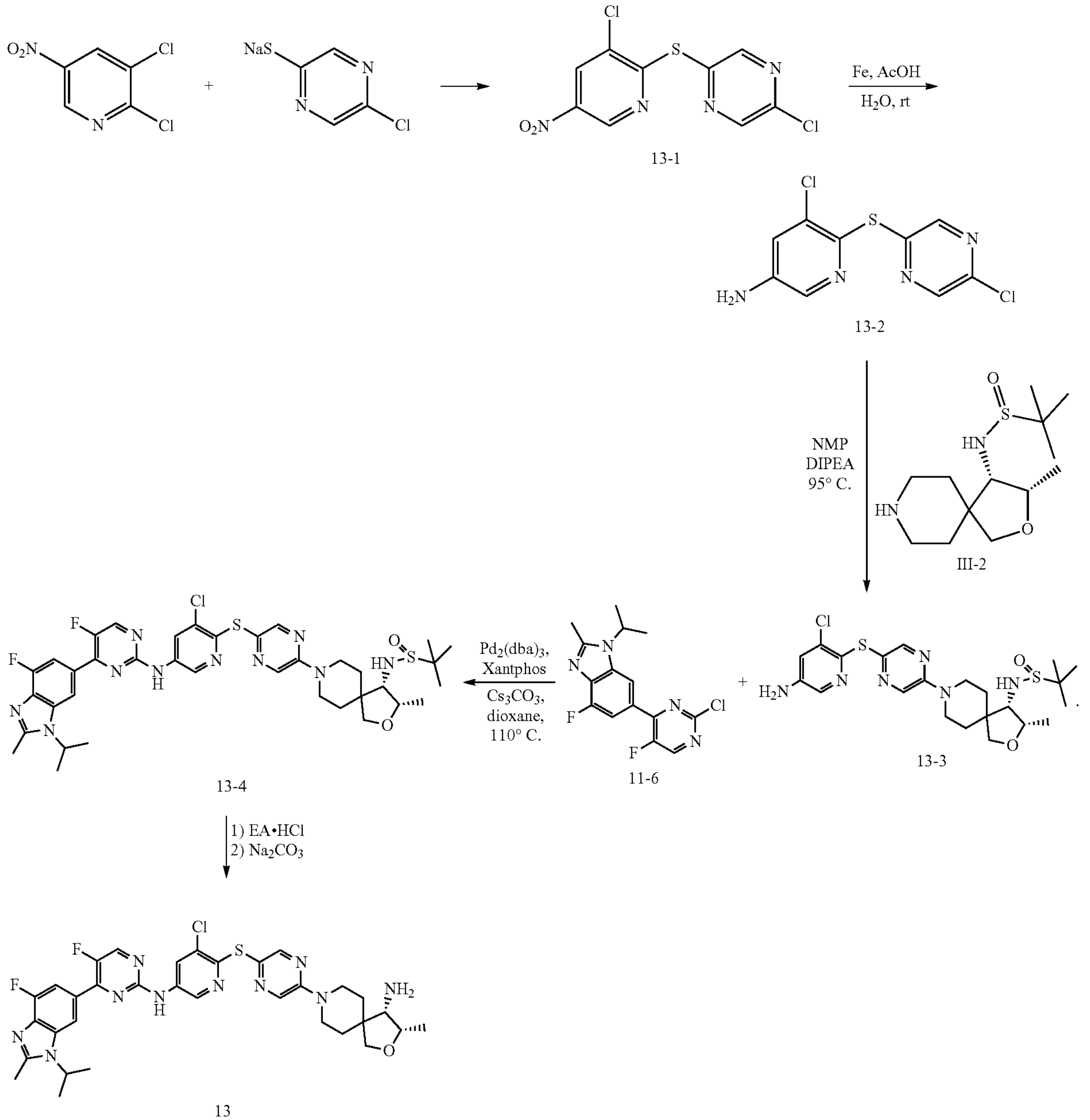

Step one: Synthesis of Compound 13-1

5-nitro-2, 3-dichloropyridine (500.0 mg, 2.59 mmol, 1.2 eq.) and 5-chloro-2-pyrazin sulfide sodium (524.0 mg, 3.11 mmol) are dissolved in NMP (6 mL). $K_2CO_3$(716.0 mg, 5.18 mmol, 2 eq.) is added. The reaction mixture is stirred overnight at the room temperature. The reaction mixture is diluted with ethyl acetate after the reaction is monitored to be complete, washed with saturated brine for 5 times. The organic phase is concentrated, separated by column chromatography to obtain the compound 13-3 (526.0 mg, yield 67%).

Step Two: Synthesis of Compound 13-2

Compound 13-1 (400.0 mg, 1.32 mmol), iron powder (295.7 mg, 5.28 mmol, 4.0 eq.), acetic acid (4.0 mL) and water (4.0 mL) are placed in a 25 mL single-necked flask. The reaction mixture is reacted at the room temperature for 12 hours. The reaction mixture is quenched by a dropwise addition of dilute hydrochloric acid after the reaction is monitored to be complete, extracted with ethyl acetate, dried with anhydrous sodium sulfate, concentrated, and separated by column chromatography to obtain compound 13-2 (318.0 mg, yield 88%).

Step Three: Synthesis of Compound 13-3

Intermediate III-2 (865.9 mg, 0.91 mmol, 1.2 eq.) and compound 13-2 (300.0 mg, 1.10 mmol) are dissolved in 4.0 mL of NMP. DIPEA (10.0 mL) is added. The reaction mixture is stirred overnight at 95° C. The reaction mixture is diluted with ethyl acetate after the reaction is monitored to be complete, washed with saturated brine water for 5 times. The organic phase is separated by column chromatography to obtain compound 13-3 (340.7 mg, yield 61%).

Step Four: Synthesis of Compound 13-4

Compound 13-3 (108.0 mg, 0.33 mmol), compound 11-5 (106.5 mg, 0.33 mmol, 1.0 eq.) $Pd_2(dba)_3$ (12.1 mg, 4 mol %), Xantphos (22.9 mg, 12 mol %) and cesium carbonate (215.0 mg, 0.66 mmol, 2.0 eq.) are placed in a sealed tube. Anhydrous dioxane (2.0 mL) is added after a protection of nitrogen. The reaction mixture is reacted overnight at 110° C. The reaction mixture is extracted with ethyl acetate after the reaction is monitored to be complete, dried with anhydrous sodium sulfate, concentrated, and separated by column chromatography to obtain compound 13-4 (144.0 mg, yield 54%).

Step Five: Synthesis of Compound 13

Compound 13-4 (43.0 mg, 0.05 mmol) is dissolved to EA (1 mL) and EA/HCl (1 mL) is added. The reaction mixture is reacted overnight at the room temperature. The reaction mixture is adjusted on a pH value to be alkaline through adding sodium carbonate solution after the reaction is monitored to be complete, extracted with EA, dried and concentrated to obtain compound 13 (13.3 mg, yield 35%). $^1$H NMR (300 MHz, Chloroform-d) δ 8.46 (d, J=2.4 Hz, 1H), 8.37 (d, J=3.7 Hz, 1H), 8.30 (d, J=2.4 Hz, 1H), 8.28 (d, J=1.2 Hz, 1H), 8.19 (d, J=1.2 Hz, 1H), 8.11 (d, J=1.1 Hz, 1H), 7.73 (d, J=11.7 Hz, 1H), 7.33 (s, 1H), 4.74 (p, J=6.9 Hz, 1H), 4.26-4.14 (m, 1H), 4.01-3.87 (m, 2H), 3.82 (d, J=8.8 Hz, 1H), 3.70 (d, J=8.8 Hz, 1H), 3.54-3.31 (m, 2H), 3.00 (d, J=4.5 Hz, 1H), 2.70 (s, 3H), 1.95-1.83 (m, 1H), 1.80-1.64 (m, 9H), 1.25 (d, J=6.4 Hz, 3H).

Example 14

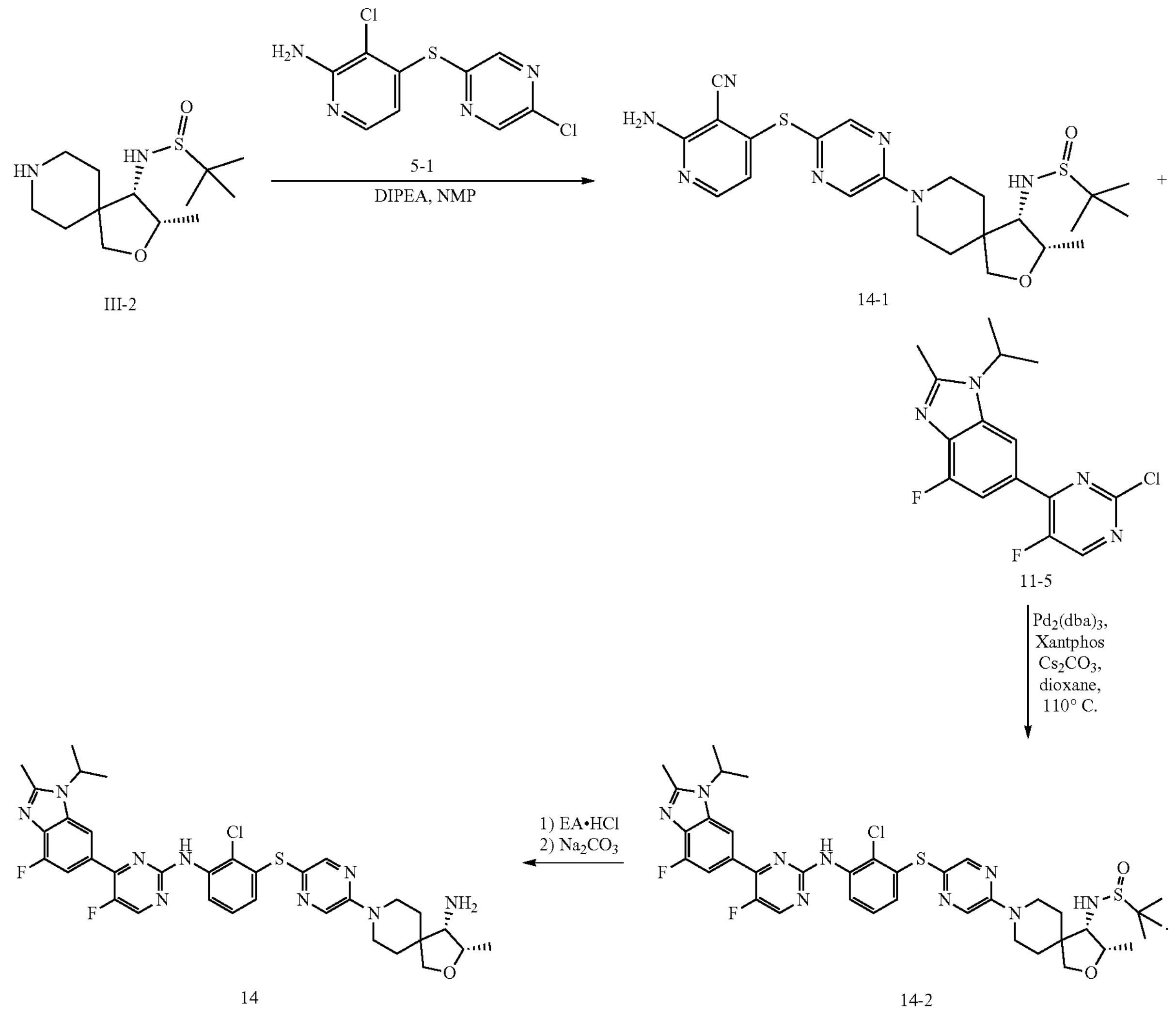

III-2

5-1

14-1

11-5

14-2

14

Step One: Synthesis of Compound 14-1

Intermediate III-2 (282.0 mg, 1.27 mmol) and compound 5-1 (278.6 mg, 1.02 mmol, 0.8 eq.) are dissolved in 4.0 mL of NMP. DIPEA (10.0 mL) is added. The reaction mixture is stirred overnight at 95° C. The reaction mixture is diluted with ethyl acetate after the reaction is monitored to be complete, washed with saturated brine water for 5 times. The organic phase is concentrated, separated by column chromatography to obtain compound 14-1 (151 mg, yield 23%).

Step Two: Synthesis of Compound 14-2

Compound 14-1 (131.0 mg, 0.26 mmol), compound 11-5 (83.9 mg, 0.26 mmol, 1.0 eq.) $Pd_2(dba)_3$ (9.5 mg, 4 mol %), Xantphos (18.1 mg, 12 mol %), and cesium carbonate (169.4 mg, 0.52 mmol, 2.0 eq.) are placed in a sealed tube. Anhydrous dioxane (4.0 mL) is added after the protection of nitrogen. The reaction mixture is reacted overnight at 110° C. The reaction mixture is extracted with ethyl acetate after the reaction is monitored to be complete, dried with anhydrous sodium sulfate, concentrated, and separated by column chromatography to obtain compound 14-2 (59.6 mg, yield 70%).

Step three: Synthesis of Compound 14

Compound 14-2 (59.6 mg, 0.07 mmol) is dissolved in EA (1 mL) and EA·HCl (1 mL) is added. The reaction mixture is reacted overnight at the room temperature. The reaction mixture is adjusted on a pH value to be alkaline through adding sodium carbonate solution after the reaction is monitored to be complete, extracted with DCM/MeOH (5:1), dried and concentrated to obtain compound 14 (39.2 mg, yield 64%). $^{1}H$ NMR (300 MHz, Chloroform-d)δ8.50 (d, J=3.7 Hz, 1H), 8.31 (d, J=1.3 Hz, 1H), 8.25 (d, J=1.4 Hz, 1H), 8.20 (d, J=1.3 Hz, 1H), 8.10 (d, J=5.3 Hz, 1H), 7.93 (s, 1H), 7.82 (d, J=11.8 Hz, 1H), 6.38 (d, J=5.3 Hz, 1H), 4.73 (p, J=6.9 Hz, 1H), 4.25-4.16 (m, 1H), 4.05-3.90 (m, 2H), 3.84 (d, J=8.8 Hz, 1H), 3.71 (d, J=8.8 Hz, 1H), 3.61-3.37 (m, 2H), 3.02 (d, J=4.6 Hz, 1H), 2.69 (s, 3H), 1.97-1.87 (m, 1H), 1.82-1.67 (m, 9H), 1.25 (d, J=6.4 Hz, 3H).

Example 15

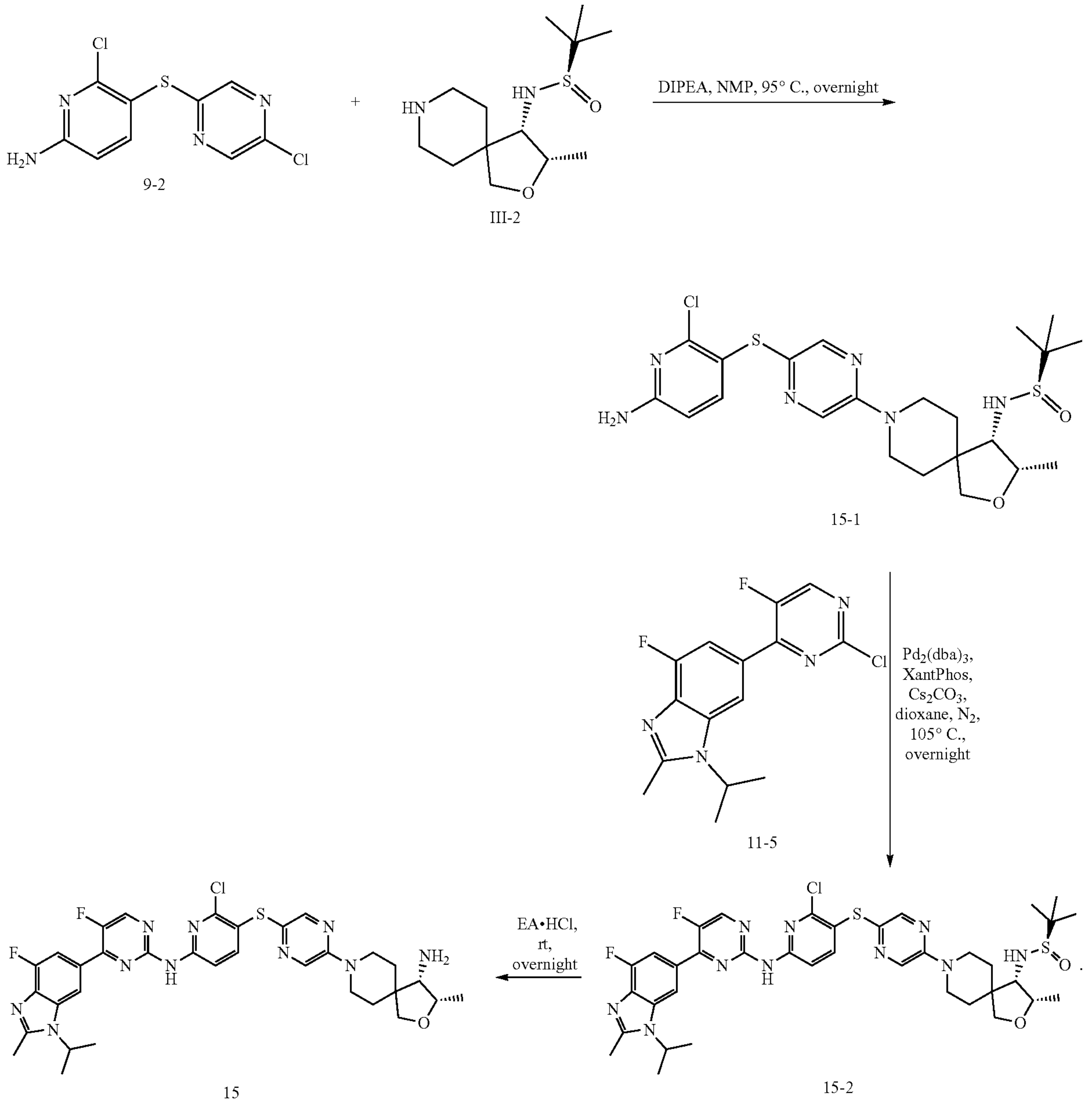

9-2
III-2
15-1
11-5
15-2
15

Step one: Synthesis of Compound 15-1

Intermediate III-2 (301.8 mg, 1.1 mmol, 2.5 eq.) and compound 9-2 (120.0 mg, 0.44 mmol) are dissolved in 3.0 mL of NMP. DIPEA (1.0 mL) is added. The reaction mixture is stirred overnight at 95° C. The reaction mixture is diluted with ethyl acetate after the reaction is monitored to be complete, washed with saturated brine water for 5 times. The organic phase is concentrated, separated by column chromatography to obtain the compound 15-1 (92.5 mg, yield 41%).

Step Two: Synthesis of Compound 15-2

Compound 15-1 (80.0 mg, 0.16 mmol), compound 11-5 (51.6 mg, 0.16 mmol, 1 eq.) $Pd_2(dba)_3$ (2.9 mg, 2 mol %), Xantphos (5.6 mg, 6 mol %) and cesium carbonate (104.3 mg, 0.32 mmol, 2 eq.) are placed in a sealed tube. Anhydrous dioxane (1.0 mL) is added after the protection of nitrogen. The reaction mixture is reacted overnight at 105° C. The reaction mixture is extracted with ethyl acetate after the reaction is monitored to be complete, dried with anhydrous sodium sulfate, concentrated, and separated by column chromatography to obtain compound 15-2 (71.0 mg, yield 56%).

Step Three: Synthesis of Compound 15

Compound 15-2 (71.0 mg, 0.09 mmol) is dissolved in EA (1.0 mL) and EA·HCl (1.0 mL) is added. The reaction mixture is reacted overnight at the room temperature.

The reaction mixture is adjusted on a pH value to be alkaline through adding sodium carbonate solution after the reaction is monitored to be complete, extracted with DCM/MeOH (5:1), dried and concentrated to obtain compound 14 (29.4 mg, 47% yield). $^1$H NMR (300 MHz, Chloroform-d) δ 8.47 (d, J=3.8 Hz, 1H), 8.34 (d, J=8.6 Hz, 1H), 8.29 (s, 1H), 8.17 (d, J=1.4 Hz, 1H), 8.16 (d, J=1.2 Hz, 1H), 8.10 (d, J=1.4 Hz, 1H), 7.75 (d, J=11.5 Hz, 1H), 7.68 (d, J=8.6 Hz, 1H), 4.73 (p, J=6.9 Hz, 1H), 4.26-4.11 (m, 1H), 3.96-3.76 (m, 3H), 3.69 (d, J=8.7 Hz, 1H), 3.49-3.27 (m, 2H), 2.99 (d, J=4.5 Hz, 1H), 2.70 (s, 3H), 1.96-1.79 (m, 2H), 1.71 (s, 3H), 1.69 (s, 3H), 1.38-1.27 (m, 2H), 1.24 (d, J=6.4 Hz, 3H).

Example 16

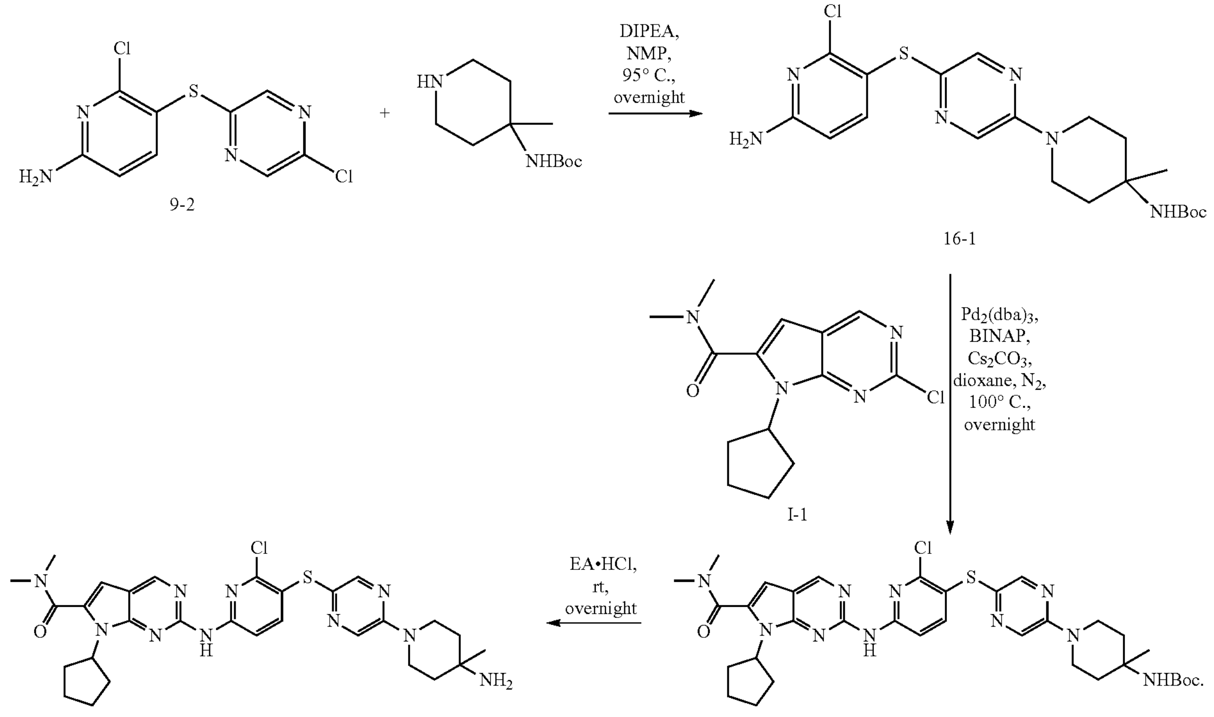

9-2 16-1 I-1 16 16-2

Step One: Synthesis of Compound 16-1

Compound 9-2 (150.0 mg, 0.55 mmol) and compound 4-methyl-4-(N-tert-butoxycarbonyl)aminopiperidine (201.4 mg, 0.94 mmol, 1.7 eq.) are dissolved in 1 mL of NMP. DIPEA (1.5 mL) is added. The reaction mixture is stirred overnight at 95° C. The reaction mixture is diluted with ethyl acetate after the reaction is monitored to be complete, washed with saturated brine water for 5 times. The organic phase is concentrated, separated by column chromatography to obtain the compound 16-1 (165.5 mg, yield 67%).

Step Two: Synthesis of Compound 16-2

Compound 16-1 (120.0 mg, 0.27 mmol), intermediate I-1 (79.1 mg, 0.27 mmol, 1.0 eq.) $Pd_2(dba)_3$ (14.8 mg, 2 mol %), BINAP (8.4 mg, 5 mol %) and cesium carbonate (175.9 mg, 0.54 mmol, 2.0 eq.) are placed in a sealed tube. Anhydrous dioxane (1.0 mL) is added after the protection of nitrogen. The reaction mixture is reacted overnight at 100° C. The reaction mixture is extracted with ethyl acetate after the reaction is monitored to be complete, dried with anhydrous sodium sulfate, concentrated, and separated by column chromatography to obtain compound 16-2 (20.0 mg, yield 10%).

Step Three: Synthesis of Compound 16

Compound 16-2 (20.0 mg, 0.03 mmol) is dissolved in EA (1.0 mL) and EA·HCl (1.0 mL) is added. The reaction mixture is reacted overnight at the room temperature. The reaction mixture is adjusted on a pH value to be alkaline through adding sodium carbonate solution after the reaction is monitored to be complete, extracted with EA, dried and concentrated to obtain compound 16 (14.1 mg, yield 77%). $^1$H NMR (300 MHz, Chloroform-d) δ 8.77 (s, 1H), 8.40 (d, J=8.6 Hz, 1H), 8.21 (s, 1H), 8.15 (d, J=1.3 Hz, 1H), 8.08 (d, J=1.3 Hz, 1H), 7.76 (d, J=8.6 Hz, 1H), 6.47 (s, 1H), 4.78 (p, J=9.0 Hz, 1H), 3.75-3.54 (m, 4H), 3.16 (s, 6H), 2.61-2.43 (m, 2H), 2.16-1.95 (m, 4H), 1.80-1.45 (m, 6H), 1.21 (s, 3H).

Example 17

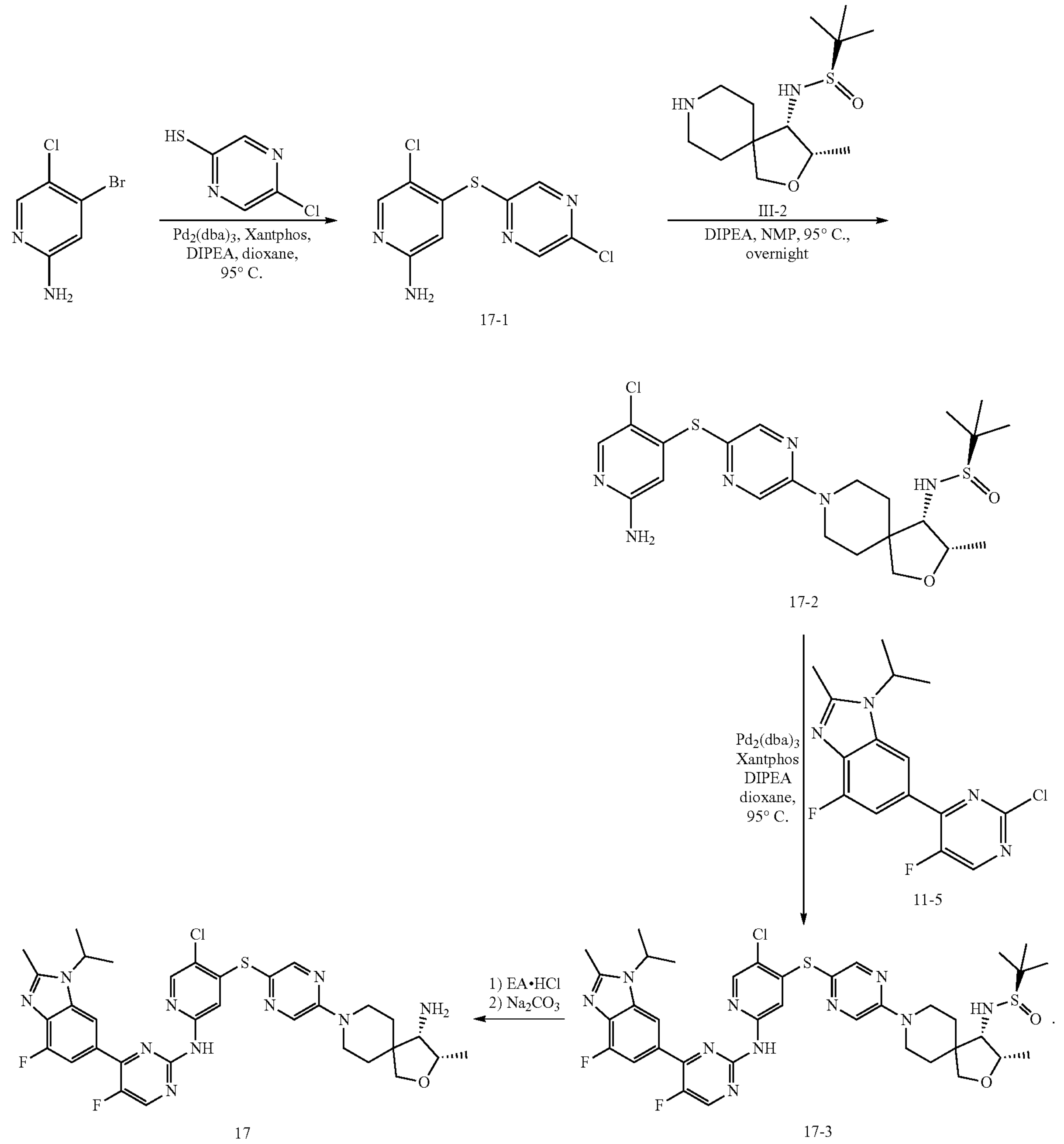

Step One: Synthesis of Compound 17-1

Compound 6-amino-3-chloro-4-bromopyridine (200.0 mg, 0.96 mmol), 5-chloro-2-mercaptopyrazine (155.4 mg, 1.06 mmol, 1.1 eq.) and $Pd_2(dba)_3$ (17.6 mg, 2 mol %), Xantphos (33.3 mg, 6 mol %), DIPEA (248.3 mg, 1.92 mmol, 2 eq.) are placed in a sealed tube.

Anhydrous dioxane (1.0 mL) is added after the protection of nitrogen. The reaction mixture is reacted overnight at 95° C., extracted with ethyl acetate after the reaction is monitored to be complete. The reaction mixture is dried with anhydrous sodium sulfate, concentrated, and separated by column chromatography to obtain compound 17-1 (95.6 mg, yield 36%).

Step Two: Synthesis of Compound 17-2

Compound 17-1 (95.6 mg, 0.35 mmol) and intermediate III-2 (107.0 mg, 0.39 mmol, 1.1 eq.) are dissolved in 1.0 mL of NMP. DIPEA (1.5 mL) is added. The reaction mixture is stirred overnight at 95° C., diluted with ethyl acetate after the reaction is monitored to be complete. The reaction mixture is washed with saturated brine water for 5 times. The organic phase is concentrated, separated by column chromatography to obtain the compound 17-2 (98.8 mg, yield 55%).

Step Three: Synthesis of Compound 17-3

Compound 17-2 (95.0 mg, 0.19 mmol), compound 11-5 (67.8 mg, 0.21 mmol, 1.1 eq.) and $Pd_2(dba)_3$ (3.5 mg, 2 mol %), Xantphos (6.6 mg, 6 mol %) and DIPEA (49.1 mg, 0.38 mmol, 2 eq.) are placed in a sealed tube. Anhydrous dioxane (1.0 mL) is added after the protection of nitrogen. The reaction mixture is reacted overnight at 95° C. The reaction mixture is extracted with ethyl acetate after the reaction is monitored to be complete, dried with anhydrous sodium sulfate, concentrated, and separated by column chromatography to obtain compound 17-3 (66.3 mg, yield 44%).

Step Three: Synthesis of Compound 17

Compound 17-3 (61.0 mg, 0.076 mmol) is dissolved in EA (1.0 mL). EA·HCl (1.0 mL) is added. The reaction mixture is reacted overnight at the room temperature. The reaction mixture is adjusted on a pH value to be alkaline through adding sodium carbonate solution after the reaction is monitored to be complete. The reaction mixture is extracted with EA, dried and concentrated to obtain compound 17 (38.2 mg, yield 73%). 1H NMR (300 MHz, Chloroform-d) δ 8.26 (d, J=1.3 Hz, 1H), 8.17 (d, J=3.6 Hz, 1H), 8.15 (s, 1H), 8.09 (d, J=1.3 Hz, 1H), 8.04 (s, 1H), 7.98 (s, 1H), 7.73 (s, 1H), 7.64 (d, J=11.5 Hz, 1H), 4.75 (p, J=7.0 Hz, 1H), 4.24-4.15 (m, 1H), 3.90-3.75 (m, 3H), 3.68 (d, J=8.8 Hz, 1H), 3.45-3.24 (m, 2H), 3.00 (d, J=4.5 Hz, 1H), 2.70 (s, 3H), 1.92-1.80 (m, 1H), 1.75-1.61 (m, 9H), 1.25 (d, J=6.4 Hz, 3H).

Example 18

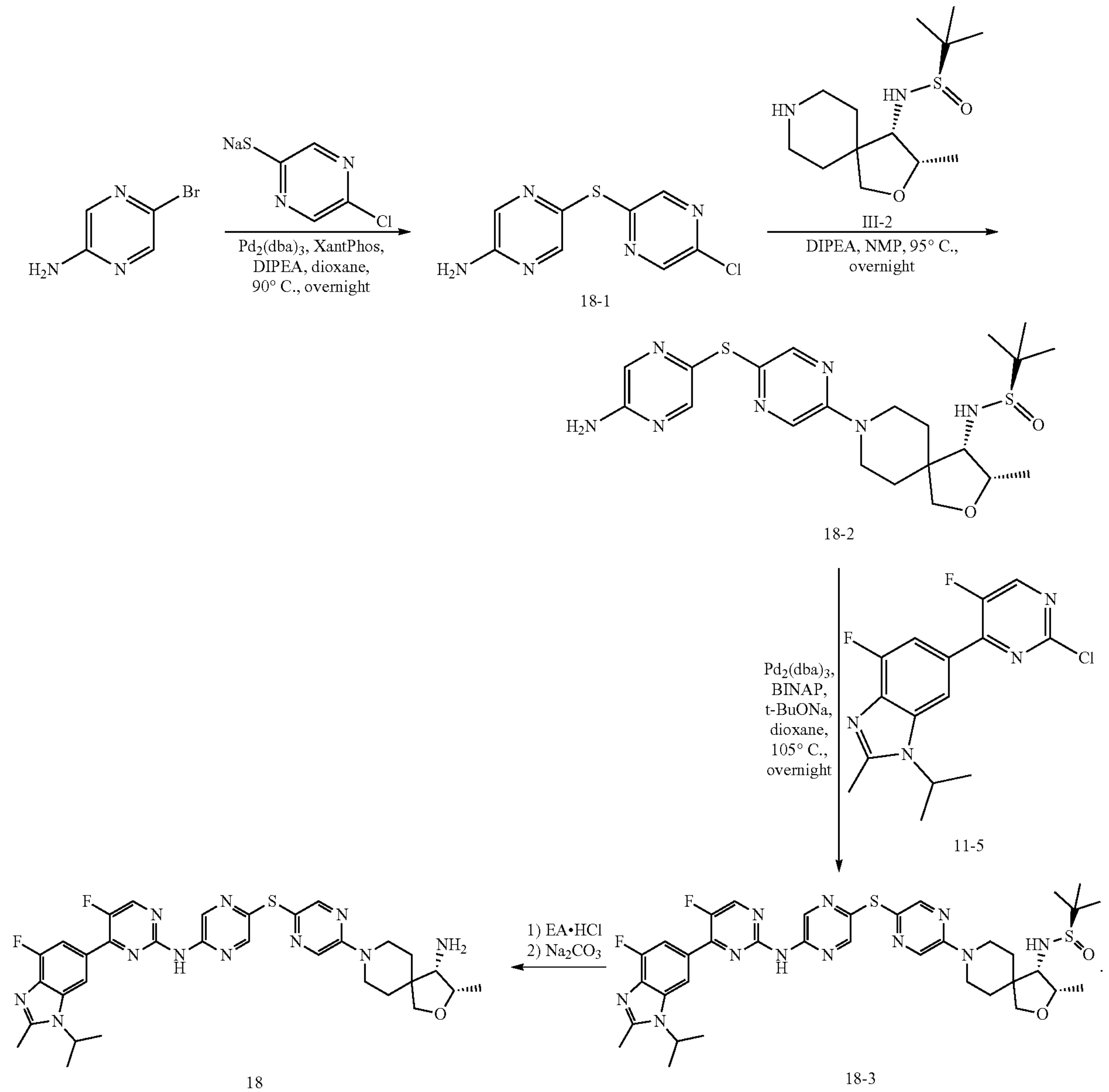

18-1

18-2

11-5

18

18-3

Step One: Synthesis of Compound 18-1

Compound 2-amino-5-bromopyrazine (400.0 mg, 2.30 mmol), 5-chloro-2-pyrazine sulfonate sodium (426.6 mg, 2.53 mmol, 1.1 eq.) $Pd_2(dba)_3$ (42.1 mg, 2 mol %), Xantphos (79.8 mg, 6 mol %) and DIPEA (594.8 mg, 4.60 mmol, 2 eq.) are placed in a sealed tube. Anhydrous dioxane (1.0 mL) is added after the protection of nitrogen. The reaction mixture is reacted overnight at 90° C. The reaction mixture is extracted with ethyl acetate after the reaction is monitored to be complete, dried with anhydrous sodium sulfate, concentrated and separated by column chromatography to obtain compound 18-1 (161.7 mg, yield 29%).

Step Two: Synthesis of Compound 18-2

Compound 18-1 (120.0 mg, 0.50 mmol), intermediate III-2 (150.9 mg, 0.55 mmol, 1.1 eq.) are dissolved in 1.0 mL of NMP. DIPEA (1.5 mL) is added. The reaction mixture is stirred overnight at 95° C. The reaction mixture is diluted with ethyl acetate after the reaction is monitored to be complete, washed with saturated brine water for 5 times. The organic is concentrated, separated by column chromatography to obtain compound 18-2 (76.3 mg, yield 32%).

Step Three: Synthesis of Compound 18-3

Compound 18-2 (76.3 mg, 0.16 mmol), compound 11-5 (58.1 mg, 0.18 mmol, 1.1 eq.), $Pd_2(dba)_3$ (2.9 mg, 2 mol %), BINAP (6.0 mg, 6 mol %), sodium t-butoxide (30.8 mg, 0.32 mmol, 2 eq.) are placed in a sealed tube. Anhydrous dioxane (1.0 mL) is added after the protection of nitrogen. The reaction mixture is reacted overnight at 90° C.. The reaction mixture is extracted with ethyl acetate after the reaction is monitored to be complete, dried with anhydrous sodium sulfate, concentrated, and separated by column chromatography to obtain compound 18-3 (10.2 mg, yield 9%).

Step Four: Synthesis of Compound 18

Compound 18-3 (10.2 mg, 0.014 mmol) is dissolved in EA (1.0 mL) and EA·HCl (1.0 mL) is added. The reaction mixture is reacted overnight at the room temperature. The reaction mixture is adjusted on a pH value to be alkaline by adding sodium carbonate solution after the reaction is monitored to be complete, extracted with EA, dried and concentrated to obtain compound 18 (7 mg, yield 75%). $^1H$ NMR (300 MHz, Chloroform-d) δ 9.62 (d, J=1.6 Hz, 1H), 8.43 (d, J=3.7 Hz, 1H), 8.30 (d, J=1.4 Hz, 1H), 8.20 (d, J=1.5 Hz, 1H), 8.16 (d, J=1.4 Hz, 1H), 8.14 (d, J=1.5 Hz, 1H), 8.01 (s, 1H), 7.76 (d, J=11.4 Hz, 1H), 4.73 (p, J=5.9, 4.8 Hz, 1H), 4.23-4.13 (m, 1H), 4.01-3.77 (m, 3H), 3.70 (d, J=8.8 Hz, 1H), 3.52-3.30 (m, 2H), 3.01 (d, J=4.5 Hz, 1H), 2.69 (s, 3H), 1.93-1.82 (m, 1H), 1.70 (m, J=6.9 Hz, 9H), 1.24 (d, J=6.4 Hz, 3H).

Example 19

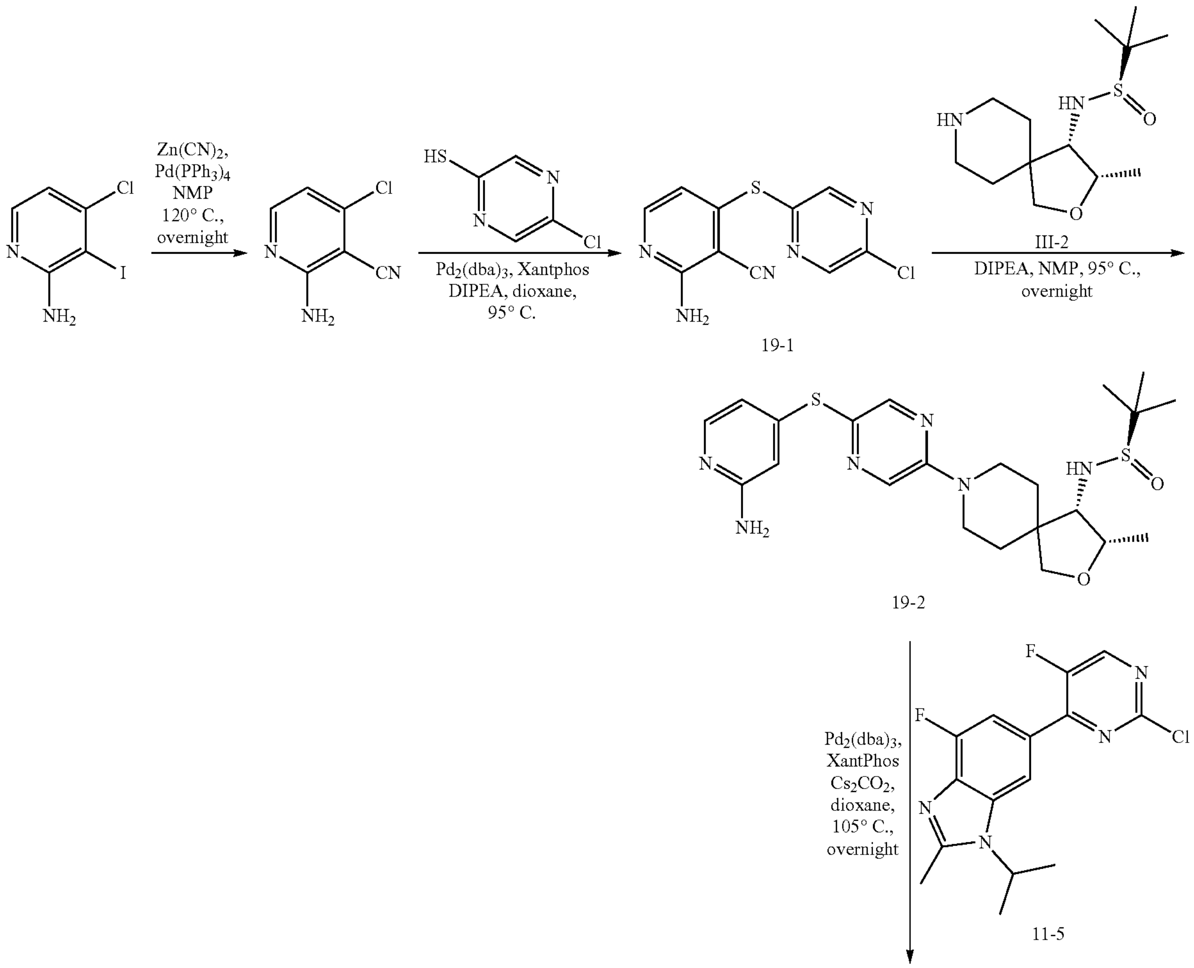

19-1

19-2

11-5

-continued

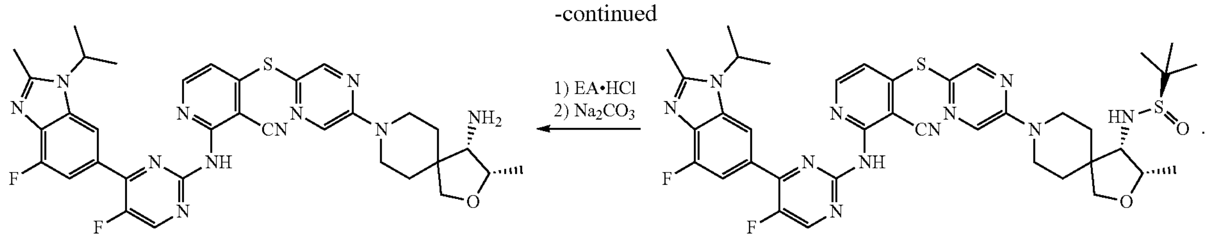

19

19-3

Step One: Synthesis of Compound 2-Amino-4-Chloro-3-Cyanopyridine

The compound 2-amino-4-chloro-3-iodopyridine (850.0 mg, 3.32 mmol), zinc cyanide (234.8 mg, 2.0 mmol, 0.6 eq.) and $Pd(PPh_3)_4$(191.8 mg, 5 mol %) are placed in a sealed tube. Anhydrous NMP (3.0 mL) is added after a protection of nitrogen. The reaction mixture is reacted overnight at 120° C. The reaction mixture is extracted with ethyl acetate after the reaction is monitored to be complete, dried with anhydrous sodium sulfate, concentrated, and separated by column chromatography to obtain the compound 2-amino-4-chloro-3-cyanopyridine (432.2 mg, yield 85%).

Step Two: Synthesis of Compound 19-1

Compound 2-amino-4-chloro-3-cyanopyridine (220.0 mg, 1.43 mmol), 5-chloro-2-mercaptopyrazine (252.2 mg, 1.72 mmol, 1.2 eq.), $Pd_2(dba)_3$ (26.2 mg, 2 mol %), Xantphos (49.6 mg, 6 mol %) and DIPEA (369.8 mg, 2.86 mmol, 2 eq.) are placed in a sealed tube. Anhydrous dioxane (1.0 mL) is added after the protection of nitrogen. The reaction mixture is reacted overnight at 95° C. The reaction mixture is extracted with ethyl acetate after the reaction is monitored to be complete, dried with anhydrous sodium sulfate, concentrated and separated by column chromatography to obtain compound 19-1 (171.3 mg, yield 45%).

Step Three: Synthesis of Compound 19-2

Compound 19-1 (107.0 mg, 0.41 mmol) and intermediate III-2 (123.5 mg, 0.45 mmol, 1.1 eq.) are dissolved in 1.0 mL of NMP. DIPEA (1.5 mL) is added. The reaction mixture is stirred overnight at 95° C. The reaction mixture is diluted with ethyl acetate after the reaction is monitored to be complete, washed with saturated brine water for 5 times. The organic phase is concentrated, separated by column chromatography to obtain Compound 19-2 (134.4 mg, yield 60%).

Step Four: Synthesis of Compound 19-3

Compound 19-2 (100.0 mg, 0.20 mmol), Compound 11-5 (71.0 mg, 0.22 mmol, 1.1 eq.), $Pd_2(dba)_3$ (3.7 mg, 2 mol %), Xantphos (6.9 mg, 6 mol %) and cesium carbonate (130.3 mg, 0.40 mmol, 2 eq.) are placed in a sealed tube. Anhydrous dioxane (1.0 mL) is added after the protection of nitrogen reacted overnight at 95° C. The reaction mixture is extracted with ethyl acetate after the reaction is monitored to be complete, dried with anhydrous sodium sulfate, concentrated and separated by column chromatography to obtain compound 19-3 (91.7 mg, yield 60%).

Step Five: Synthesis of Compound 19

Compound 19-3 (80.0 mg, 0.10 mmol) is dissolved in EA (1.0 mL) and EA·HCl (1.0 mL) is added. The reaction mixture is reacted overnight at the room temperature, adjusted a pH value to be alkaline by adding sodium carbonate solution after the reaction is monitored to be complete. The reaction mixture is extracted with EA, dried and concentrated to obtain compound 19 (8.9 mg, yield 13%). $^1$H NMR (300 MHz, Chloroform-d) δ 8.50 (d, J=3.6 Hz, 1H), 8.30 (d, J=1.1 Hz, 1H), 8.27 (d, J=5.5 Hz, 1H), 8.24 (d, J=1.0 Hz, 1H), 8.21 (d, J=1.2 Hz, 1H), 8.19 (s, 1H), 7.76 (d, J=11.7 Hz, 1H), 6.55 (d, J=5.5 Hz, 1H), 4.75 (p, J=6.9 Hz, 1H), 4.26-4.15 (m, 1H), 4.09-3.93 (m, 2H), 3.85 (d, J=8.8 Hz, 1H), 3.71 (d, J=8.8 Hz, 1H), 3.59-3.36 (m, 2H), 3.04 (d, J=4.5 Hz, 1H), 2.69 (s, 3H), 1.99-1.88 (m, 1H), 1.82-1.61 (m, 9H), 1.26 (d, J=6.2 Hz, 3H).

Example 20

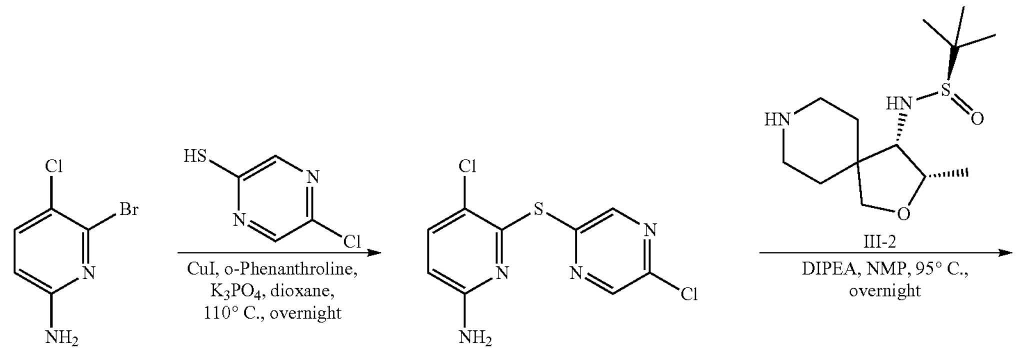

20-1

-continued

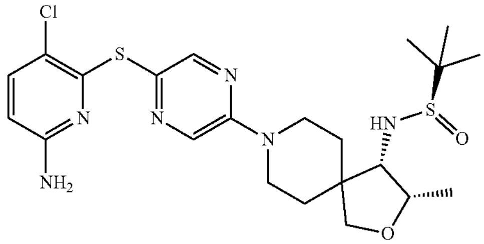

20-2

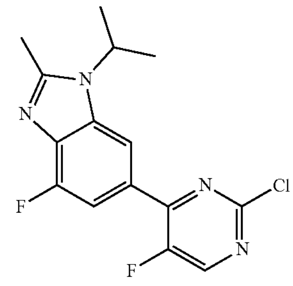

11-5

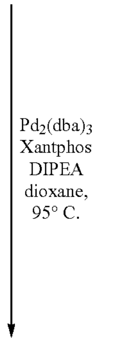

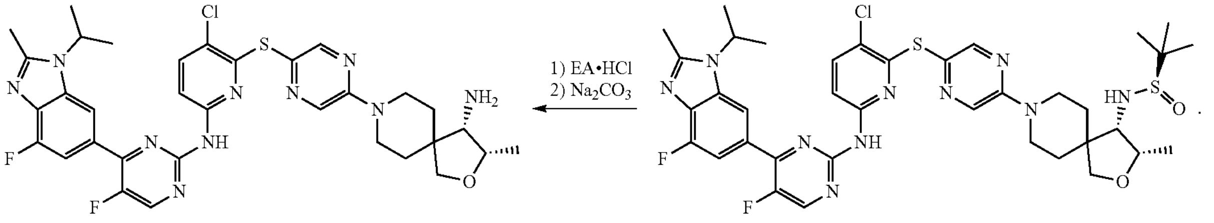

20 20-3

Step One: Synthesis of Compound 20-1

Compound 2-amino-5-chloro-6-bromopyridine (250.0 mg, 1.20 mmol), 5-chloro-2-mercaptopyrazine (211.1 mg, 1.44 mmol, 1.2 eq.) and CuI (45.7 mg, 0.2 eq), 1,10-phenanthroline (86.5 mg, 0.4 eq.) and $K_3PO_4$ (509.5 mg, 2.40 mmol, 2 eq.) are placed in a sealed tube. Anhydrous dioxane (2.0 mL) is added after a protection of nitrogen. The reaction mixture is reacted overnight at 110° C. The reaction mixture is extracted with ethyl acetate after the reaction is monitored to be complete, dried with anhydrous sodium sulfate, concentrated, and separated by column chromatography to obtain compound 20-1 (127.7 mg, yield 39%).

Step Two: Synthesis of Compound 20-2

Compound 20-1 (102.0 mg, 0.37 mmol) and intermediate III-2 (112.5 mg, 0.41 mmol, 1.1 eq.) are dissolved in 1.0 mL of NMP. DIPEA (1.5 mL) is added. The reaction mixture is stirred overnight at 95° C. The reaction mixture is diluted with ethyl acetate after the reaction is monitored to be complete, washed with saturated brine water for 5 times. The organic phase is concentrated, separated by column chromatography the organic phase to obtain compound 20-2 (43.2 mg, yield 23%).

Step Three: Synthesis of Compound 20-3

Compound 20-2 (43.2 mg, 0.085 mmol), Compound 11-5 (30.3 mg, 0.094 mmol, 1.1 eq.) $Pd_2(dba)_3$ (1.6 mg, 2 mol %), Xantphos (3.0 mg, 6 mol %) and DIPEA (22.0 mg, 0.17 mmol, 2 eq.) are placed in a sealed tube. Anhydrous dioxane (1.0 mL) is added after the protection of nitrogen. The reaction mixture is reacted overnight at 95° C. The reaction mixture is extracted with ethyl acetate after the reaction is monitored to be complete, dried with anhydrous sodium sulfate, concentrated and separated by column chromatography to obtain a crude product (22.3 mg) of compound 20-3.

Step Four: Synthesis of Compound 20

Compound 20-3 (22.3 mg, 0.028 mmol) is dissolved in EA (1.0 mL) and EA·HCl (1.0 mL) is added. The reaction mixture is reacted overnight at the room temperature, adjusted a pH value to be alkaline by adding sodium carbonate solution after the reaction is monitored to be complete. The reaction mixture is extracted with EA, dried and concentrated to obtain compound 20 (9.7 mg, yield 16%). $^1H$ NMR (300 MHz, Chloroform-d) δ 8.37 (d, J=3.7 Hz, 1H), 8.29 (d, J=1.3 Hz, 1H), 8.22 (d, J=1.3 Hz, 1H), 8.14 (d, J=8.7 Hz, 1H), 8.10 (d, J=1.0 Hz, 1H), 7.76-7.67 (m, 2H), 7.54 (d, J=8.7 Hz, 1H), 4.73 (p, J=7.0 Hz, 1H), 4.27-4.16 (m, 1H), 4.07-3.90 (m, 2H), 3.84 (d, J=8.8 Hz, 1H), 3.73 (d, J=8.8 Hz, 1H), 3.58-3.36 (m, 2H), 3.03 (d, J=4.6 Hz, 1H), 2.69 (s, 3H), 2.00-1.89 (m, 1H), 1.84-1.67 (m, 9H), 1.25 (d, J=6.4 Hz, 3H).

Example 21

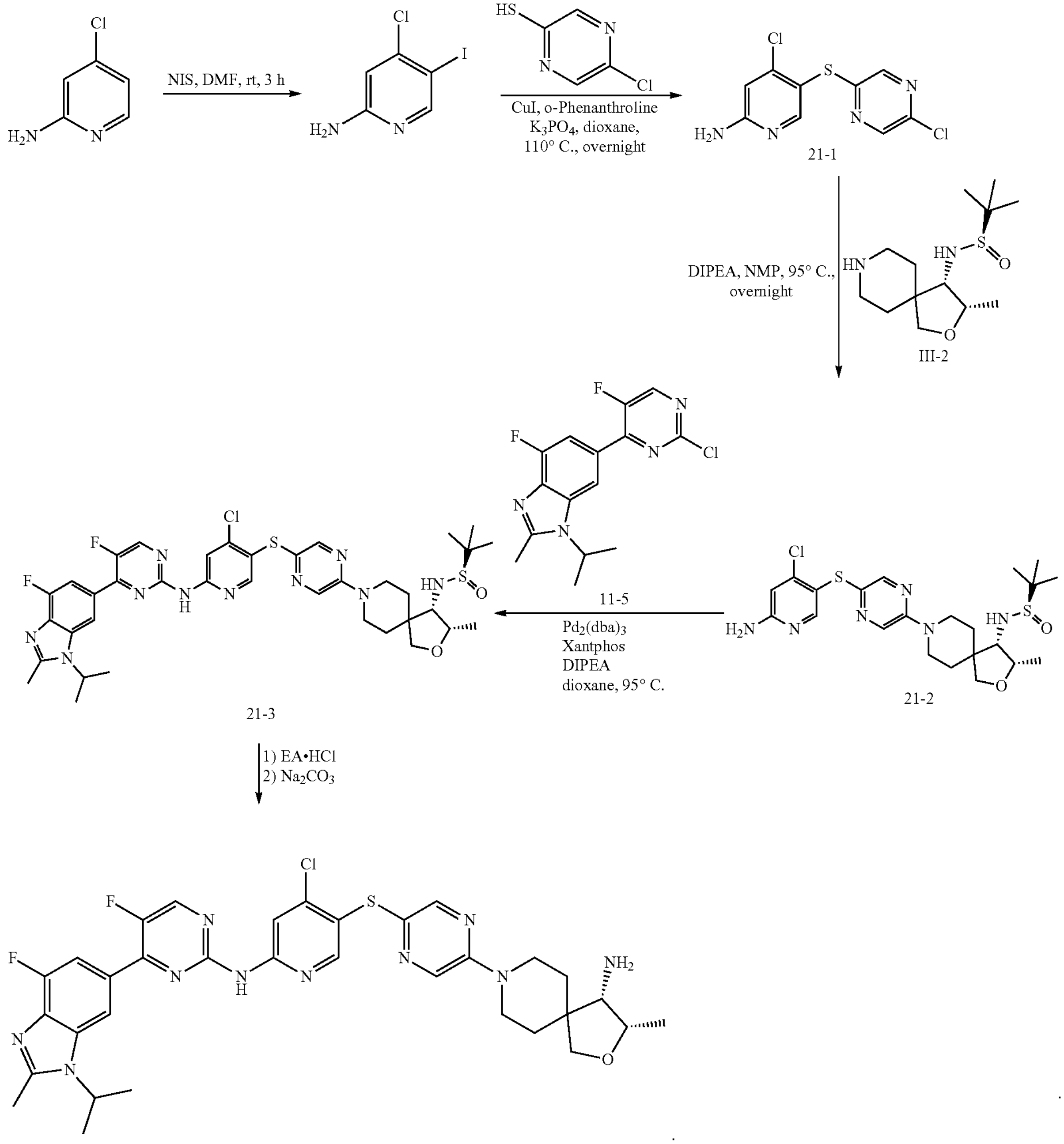

21

Step One: Synthesis of Compound 2-Amino-4-Chloro-5-Iodopyridine

Compound 2-amino-4-chloropyridine (1.00 g, 7.78 mmol), NIS (1.92 g, 8.56 mmol, 1.1 eq.) and DMF (15.0 ml) are placed in a 50 ml single-necked flask, reacted at the room temperature for 3 hours. The reaction mixture is extracted with ethyl acetate after the reaction is monitored to be complete, dried with anhydrous sodium sulfate, concentrated, and separated by column chromatography to obtain compound 2-amino-4-chloro-5-iodopyridine (1.10 g, yield 56%).

Step Two: Synthesis of Compound 21-1

Compound 2-amino-4-chloro-5-iodopyridine (250.0 mg, 1.0 mmol), 5-chloro-2-mercaptopyrazine (161.3 mg, 1.1 mmol, 1.1 eq.), CuI (38.1 mg, 0.2 eq.), 1,10-phenanthroline (72.1 mg, 0.4 eq.) and $K_3PO_4$ (424.6 mg, 2.00 mmol, 2 eq.) are placed in a sealed tube. Anhydrous dioxane (2.0 mL) is added after a protection of nitrogen. The reaction mixture is reacted overnight at 110° C. The reaction mixture is extracted with ethyl acetate after the reaction is monitored to be complete, dried with anhydrous sodium sulfate, concentrated, and separated by column chromatography to obtain compound 21-1 (145.2 mg, yield 53%).

Step Three: Synthesis of Compound 21-2

Compound 21-1 (145.2 mg, 0.53 mmol) and intermediate III-2 (158.6 mg, 0.58 mmol, 1.1 eq.) are dissolved in 1.0 mL of NMP. DIPEA (1.5 mL) is added. The reaction mixture is stirred overnight at 95° C. The reaction mixture is diluted with ethyl acetate after the reaction is monitored to be complete, washed with saturated brine water for 5 times. The organic phase is concentrated, separated by column chromatography to obtain compound 21-2 (115.0 mg, yield 23%).

Step Four: Synthesis of Compound 21-3

Compound 21-2 (115.0 mg, 0.22 mmol), Compound 11-5 (77.5 mg, 0.24 mmol, 1.1 eq.), $Pd_2(dba)_3$ (4.0 mg, 2 mol %), Xantphos (7.6 mg, 6 mol %) and DIPEA (56.9 mg, 0.44 mmol, 2 eq.) are placed in a sealed tube. Anhydrous dioxane (1.0 mL) is added after the protection of nitrogen reacted overnight at 95° C. The reaction mixture is extracted with ethyl acetate after the reaction is monitored to be complete, dried with anhydrous sodium sulfate, concentrated and separated by column chromatography to obtain compound 21-3 (91.5 mg, yield 52%).

Step Four: Synthesis of Compound 21

Compound 21-3 (75.0 mg, 0.094 mmol) is dissolved in EA (1.0 mL) and EA·HCl (1.0 mL) is added. The reaction mixture is reacted overnight at the room temperature, adjusted a pH value to be alkaline by adding sodium carbonate solution after the reaction is monitored to be complete. The reaction mixture is extracted with EA, and dried and concentrated to obtain compound 21 (18.0 mg, yield 28%). $^1H$ NMR (300 MHz, Chloroform-d) δ 8.66 (s, 1H), 8.47 (d, J=3.7 Hz, 1H), 8.39 (s, 1H), 8.38 (s, 1H), 8.15 (d, J=1.3 Hz, 1H), 8.11 (d, J=1.4 Hz, 1H), 8.05 (d, J=1.4 Hz, 1H), 7.77 (d, J=11.6 Hz, 1H), 4.76 (p, J=6.9 Hz, 1H), 4.23-4.13 (m, 1H), 3.92-3.76 (m, 3H), 3.68 (d, J=8.8 Hz, 1H), 3.46-3.24 (m, 2H), 2.98 (d, J=4.5 Hz, 1H), 2.70 (s, 3H), 1.91-1.80 (m, 1H), 1.75-1.61 (m, 9H), 1.23 (d, J=6.4 Hz, 3H).

Example 22

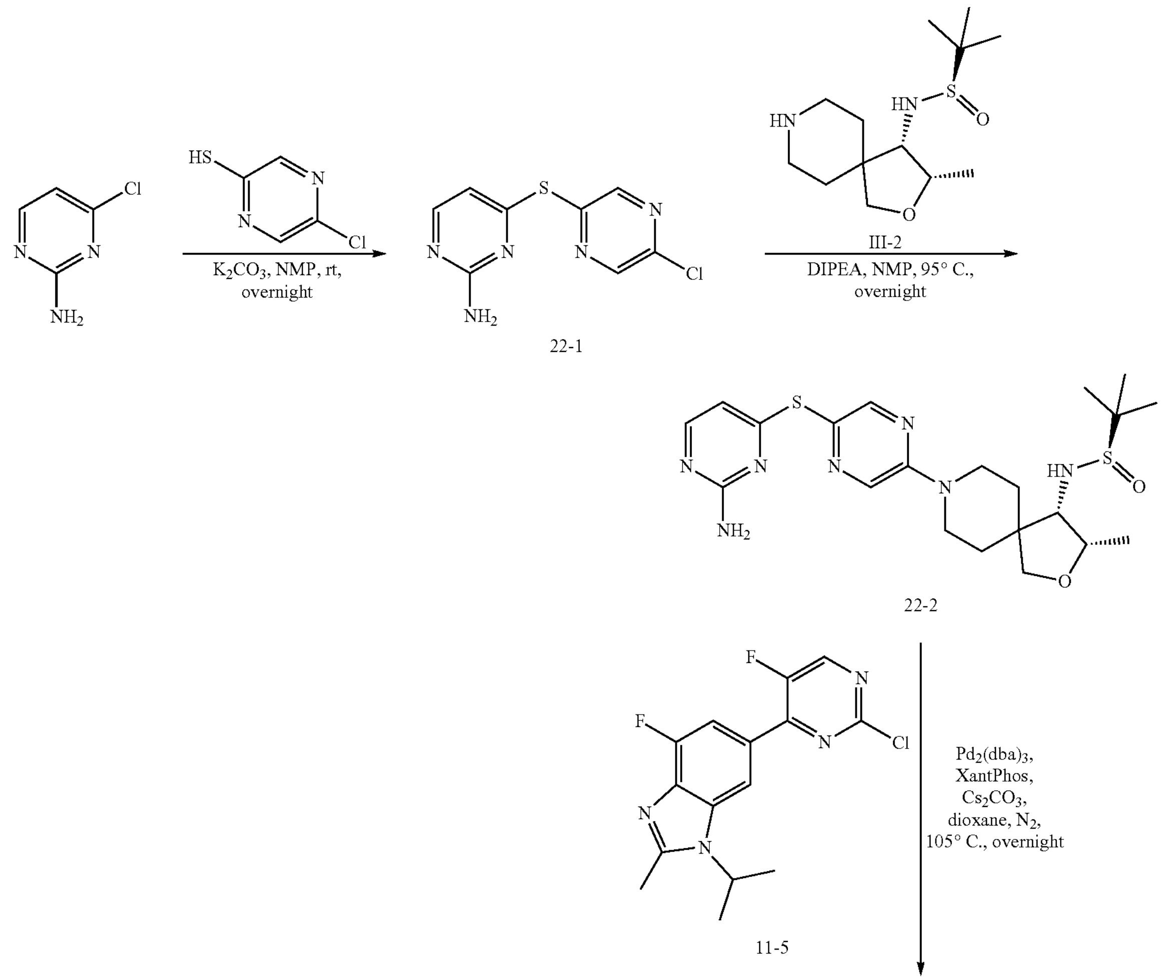

22-1

22-2

11-5

-continued

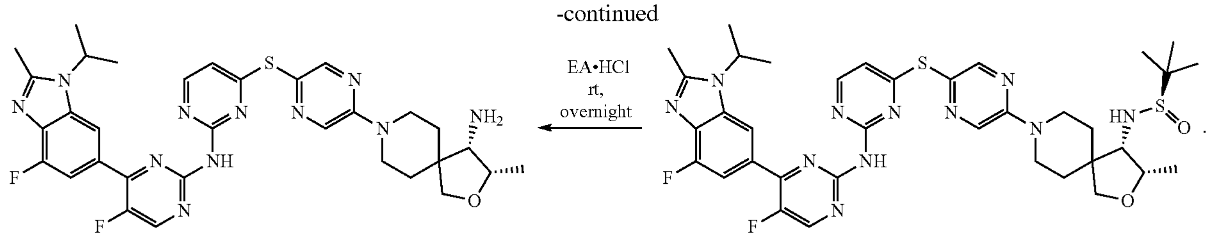

22 22-3

Step One: Synthesis of Compound 22-1

Compound 2-amino-4-chloropyrimidine (500.0 mg, 3.9 mmol) and Compound 5-chloro-2-mercaptopyrazine (628.9 mg, 4.29 mmol, 1.1 eq.) are dissolved in 10.0 ml of NMP. Potassium carbonate (1.08 g, 7.80 mmol, 2 eq.) is added. The reaction mixture is stirred overnight at the room temperature. The reaction mixture is diluted with ethyl acetate after the reaction is monitored to be complete, washed with saturated brine water for 5 times. The organic phase is concentrated, separated by column chromatography to obtain compound 22-1 (304.1 mg, yield 33%).

Step Two: Synthesis of Compound 22-2

Compound 22-1 (120.0 mg, 0.50 mmol) and intermediate III-2 (175.6 mg, 0.64 mmol, 1.1 eq.) are dissolved in 1.0 mL of NMP. DIPEA (1.5 mL) is added. The reaction mixture is stirred overnight at 95° C. The reaction mixture is diluted with ethyl acetate after the reaction is monitored to be complete, washed with saturated brine water for 5 times. The organic phase is concentrated, separated by column chromatography to obtain the compound 22-2 (105.4 mg, yield 46%).

Step Three: Synthesis of Compound 22-3

Compound 22-2 (105.4 mg, 0.22 mmol), Compound 11-5 (77.5 mg, 0.24 mmol, 1.1 eq.), $Pd_2(dba)_3$ (4.0 mg, 2 mol %), Xantphos (7.6 mg, 6 mol %) and DIPEA (56.9 mg, 0.44 mmol, 2 eq.) are placed in a sealed tube. Anhydrous dioxane (1.0 mL) is added after a protection of nitrogen. The reaction mixture is reacted overnight at 95° C. The reaction mixture is extracted with ethyl acetate after the reaction is monitored to be complete, dried with anhydrous sodium sulfate, concentrated, and separated by column chromatography to obtain compound 22-3 (47.1 mg, yield 37%).

Step Four: Synthesis of Compound 22

Compound 22-3 (42.0 mg, 0.055 mmol) is dissolved in EA (1.0 mL) and EA·HCl (1.0 mL) is added. The reaction mixture is reacted overnight at the room temperature. The reaction mixture is adjusted on a pH value to be alkaline by adding sodium carbonate solution after the reaction is monitored to be complete, extracted with EA, dried and concentrated to obtain compound 22 (23.0 mg, yield 63%). $^1H$ NMR (300 MHz, Chloroform-d) δ 8.52 (d, J=3.5 Hz, 1H), 8.34 (d, J=1.4 Hz, 1H), 8.31 (d, J=5.5 Hz, 1H), 8.23 (d, J=1.3 Hz, 1H), 8.21 (d, J=1.4 Hz, 1H), 7.84 (d, J=11.7 Hz, 1H), 6.60 (d, J=5.5 Hz, 1H), 4.76 (p, J=7.0 Hz, 1H), 4.26-4.16 (m, 1H), 4.07-3.92 (m, 2H), 3.85 (d, J=9.0 Hz, 1H), 3.72 (d, J=9.0 Hz, 1H), 3.56-3.34 (m, 2H), 3.05 (d, J=4.6 Hz, 1H), 2.70 (s, 3H), 1.98-1.86 (m, 1H), 1.82-1.68 (m, 9H), 1.26 (d, J=6.4 Hz, 3H).

Example 23

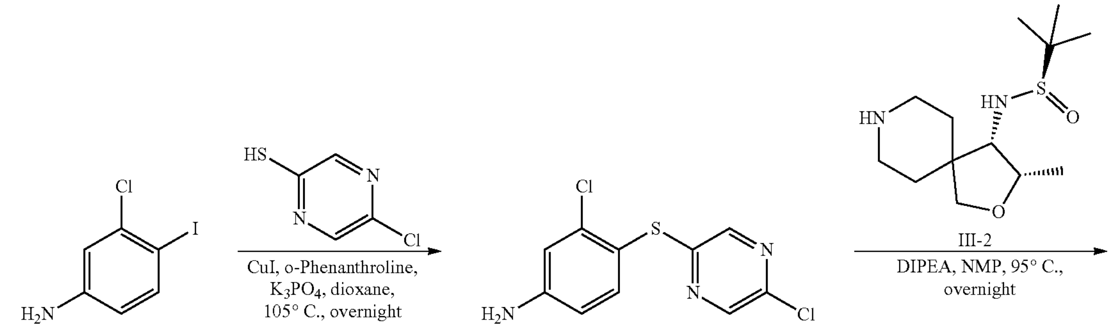

23-1

-continued

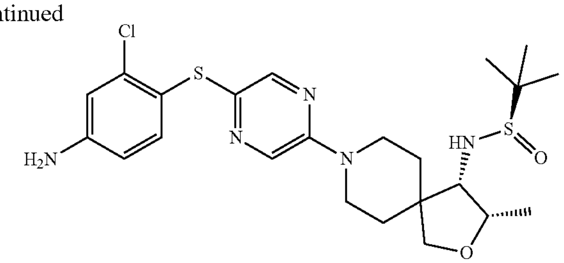

23-2

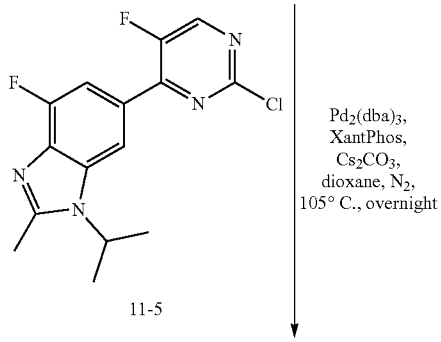

11-5

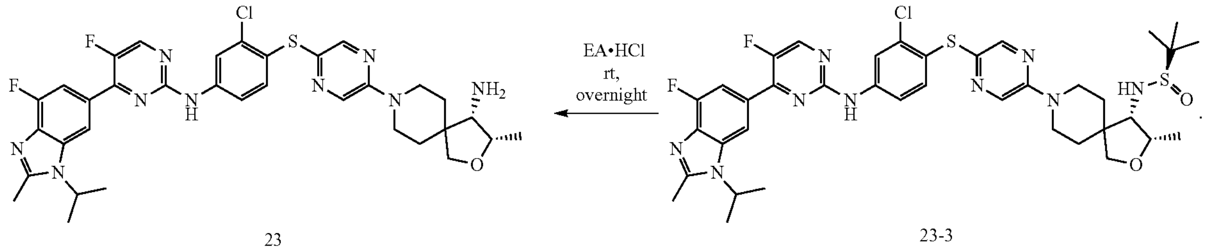

23 23-3

Step One: Synthesis of Compound 23-1

Compounds 3-chloro-4-iodoaniline (300.0 mg, 1.20 mmol), 5-chloro-2-mercaptopyrazine (193.5 mg, 1.32 mmol, 1.1 eq.) CuI (45.7 mg, 0.2 eq.), 1,10-phenanthroline (86.5 mg, 0.4 eq.) and $K_3PO_4$ (331.7 mg, 2.40 mmol, 2 eq.) are placed in a sealed tube. Anhydrous dioxane (2.0 mL) is added after a protection of nitrogen. The reaction mixture is reacted overnight at 110° C. The reaction mixture is extracted with ethyl acetate after the reaction is monitored to be complete, dried with anhydrous sodium sulfate, concentrated, and separated by column chromatography to obtain compound 23-1 (212.4 mg, yield 56%).

Step Two: Synthesis of Compound 23-2

Compound 23-1 (120.0 mg, 0.44 mmol) and intermediate III-2 (131.7 mg, 0.48 mmol, 1.1 eq.) are dissolved in 1.0 mL of NMP. DIPEA (1.5 mL) is added. The reaction mixture is stirred overnight at 95° C. The reaction mixture is diluted with ethyl acetate after the reaction is monitored to be complete, washed with saturated brine water for 5 times. The organic phase is concentrated, separated by column chromatography to obtain compound 23-2 (93.5 mg, yield 41%).

Step Three: Synthesis of Compound 23-3

Compound 23-2 (80.0 mg, 0.16 mmol), Compound 11-5 (58.1 mg, 0.18 mmol, 1.1 eq.) $Pd_2(dba)_3$ (2.9 mg, 2 mol %), Xantphos (5.6 mg, 6 mol %) and DIPEA (41.4 mg, 0.32 mmol, 2 eq.) are placed in a sealed tube. Anhydrous dioxane (1.0 mL) is added after the protection of nitrogen. The reaction mixture is reacted overnight at 95° C.. The reaction mixture is extracted with ethyl acetate after the reaction is monitored to be complete, dried with anhydrous sodium sulfate, concentrated, and separated by column chromatography to obtain compound 23-3 (67.3 mg, yield 53%).

Step Four: Synthesis of Compound 23

Compound 23-3 (60.0 mg, 0.075 mmol) is dissolved in EA (1.0 mL) and EA·HCl (1.0 mL) is added. The reaction mixture is reacted overnight at the room temperature. The reaction mixture is adjusted on a pH value to be alkaline by adding sodium carbonate solution after the reaction is monitored to be complete, extracted with EA, dried and concentrated to obtain compound 23 (42.6 mg, yield 82%). $^1H$ NMR (300 MHz, Chloroform-d) δ 8.37 (d, J=3.8 Hz, 1H), 8.15 (d, J=1.2 Hz, 1H), 8.11-8.07 (m, 2H), 8.05 (d, J=2.2 Hz, 1H), 7.76 (d, J=11.6 Hz, 1H), 7.38 (dd, J=8.6, 2.2 Hz, 1H), 7.32 (d, J=8.6 Hz, 1H), 7.28 (s, 1H), 4.75 (p, J=7.0 Hz, 1H), 4.23-4.14 (m, 1H), 3.94-3.76 (m, 3H), 3.68 (d, J=8.8 Hz, 1H), 3.47-3.24 (m, 2H), 2.99 (d, J=4.5 Hz, 1H), 2.70 (s, 3H), 1.92-1.80 (m, 1H), 1.76-1.67 (m, 9H), 1.23 (d, J=6.4 Hz, 3H).

Example 24

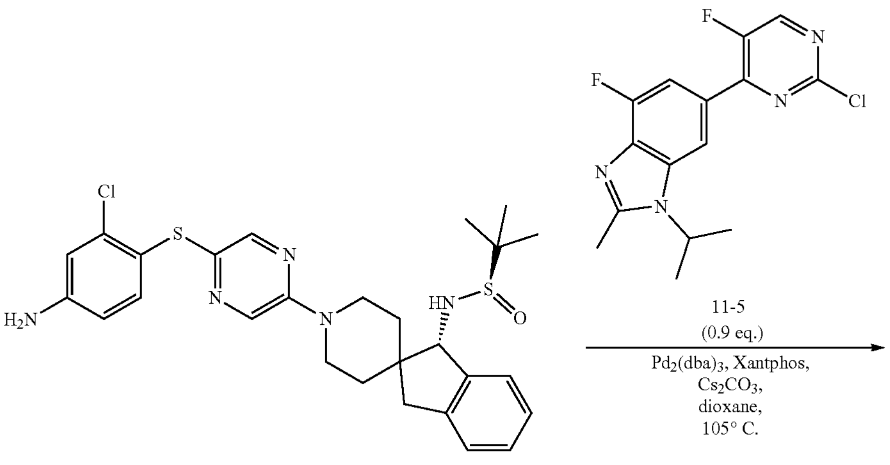

9-3

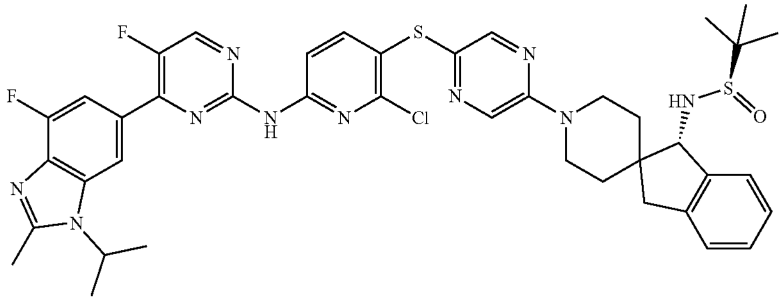

24-1

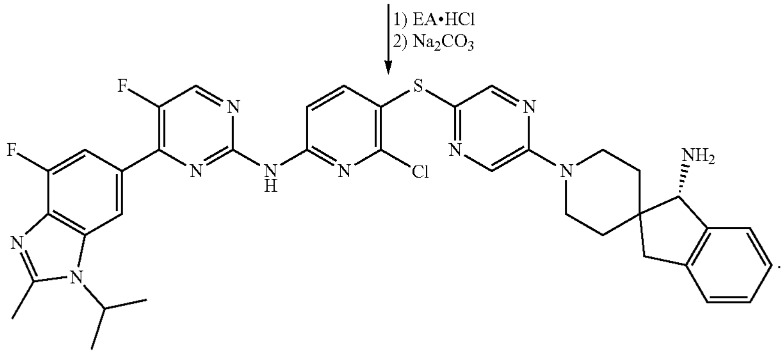

24

Step One: Synthesis of Compound 24-1

Compound 9-3 (106.0 mg, 0.2 mmol), Compound 11-5 (58.0 mg, 0.18 mmol, 0.9 eq.) $Pd_2(dba)_3$ (2.9 mg, 2 mol %), Xantphos (5.6 mg, 6 mol %) and cesium carbonate (41.4 mg, 0.32 mmol, 2 eq.) are placed in a sealed tube. Anhydrous dioxane (1.0 mL) is added under the protection of nitrogen. The reaction mixture is reacted overnight at 105° C. The reaction mixture is extracted with ethyl acetate after the reaction is monitored to be complete, dried with anhydrous sodium sulfate, concentrated, and separated by column chromatography to obtain compound 24-1 (88.6 mg, yield 61%).

Step Two: Synthesis of Compound 24

Compound 24-1 (80.0 mg, 0.1 mmol) is dissolved in EA (1.0 mL) and EA·HCl (1.0 mL) is added. The reaction mixture is reacted overnight at the room temperature. The reaction mixture is adjusted on a pH value to be alkaline by adding sodium carbonate solution after the reaction is monitored to be complete, extracted with EA, dried and concentrated to obtain compound 24 (38.0 mg, yield 54%). $^1H$ NMR (300 MHz, Chloroform-d) δ 8.48 (d, J=3.7 Hz, 1H), 8.34 (d, J=8.6 Hz, 1H), 8.31 (s, 1H), 8.18 (d, J=1.2 Hz, 1H), 8.16 (d, J=1.2 Hz, 1H), 8.12 (d, J=1.1 Hz, 1H), 7.75 (d, J=11.9 Hz, 1H), 7.67 (d, J=8.6 Hz, 1H), 7.37-7.29 (m, 1H), 7.26-7.16 (m, 3H), 4.73 (p, J=6.9 Hz, 1H), 4.25-4.11 (m, 2H), 3.99 (s, 1H), 3.31-3.15 (m, 2H), 3.09 (d, J=15.6 Hz, 1H), 2.73 (d, J=15.6 Hz, 1H), 2.70 (s, 3H), 1.93-1.75 (m, 2H), 1.70 (d, J=7.0 Hz, 6H), 1.38 (d, J=11.5 Hz, 2H).

Example 25

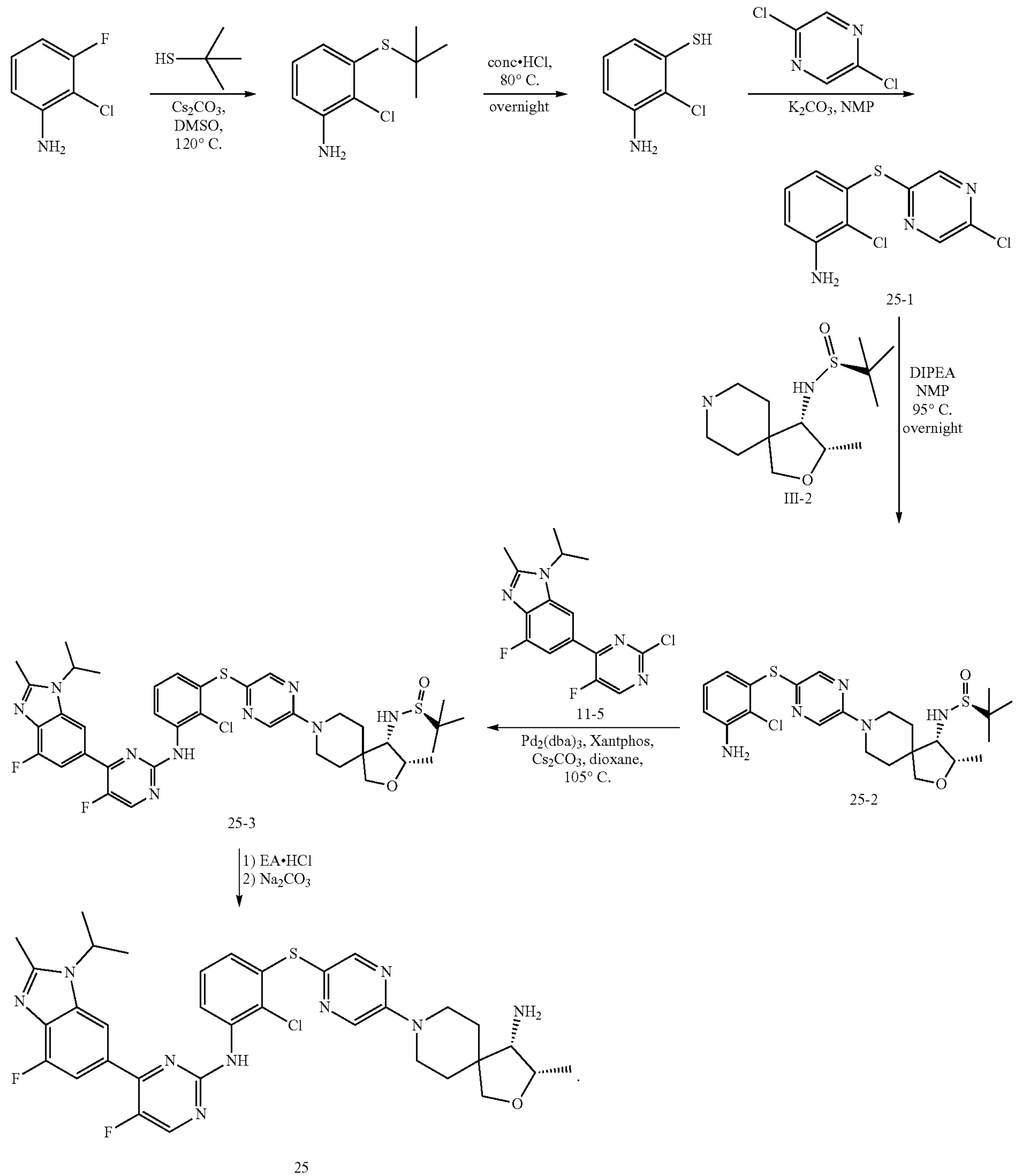

25-1, III-2, 11-5, 25-2, 25-3, 25

Step One: Synthesis of 3-(Tert-Butylthio)-2-Chloroaniline

Compound 3-fluoro-2-chloroaniline (1.00 g, 6.87 mmol), t-butylmercaptan (1.86 g, 20.61 mmol, 3.0 eq.), cesium carbonate (3.36 g, 10.31 mmol, 1.5 eq.) and DMSO (15.0 mL) are placed in a single-necked bottle, reacted overnight at 120° C. under a protection of nitrogen. The reaction mixture is extracted with ethyl acetate after the reaction is monitored to be complete, dried with anhydrous sodium sulfate, concentrated and separated by column chromatography to obtain a crude product (1.67 g) of the compound 3-(tert-butylthio)-2-chloroaniline.

Step Two: Synthesis of 2-Chloro-3-Mercaptoaniline

Compound 3-(tert-butylthio)-2-chloroaniline (1.67 g, 7.74 mmol) is dissolved in 15.0 mL of concentrated hydrochloric acid. The reaction mixture is reacted overnight at 80° C. The reaction mixture is adjusted on a pH value to be alkaline through adding sodium carbonate after the reaction is monitored to be complete, extracted with ethyl acetate, dried with anhydrous sodium sulfate, concentrated, and separated by column chromatography to obtain compound 2-chloro-3-mercaptoaniline (577.5 mg, yield 47% in two steps).

Step Three: Synthesis of Compound 25-1

Compound 2-chloro-3-mercaptoaniline (577.5 mg, 3.62 mmol), Compound 2,5-dichloropyrazine (593.0 mg, 3.98 mmol, 1.1 eq.) are dissolved in 4.0 ml of NMP. Potassium carbonate (1.00 g, 7.24 mmol, 2 eq.) is added. The reaction mixture is stirred overnight at the room temperature. The reaction mixture is diluted with ethyl acetate after the reaction is monitored to be complete, washed with saturated brine water for 5 times. The organic phase is concentrated, separated by column chromatography to obtain Compound 25-1 (112.5 mg, yield 11%).

Step Four: Synthesis of Compound 25-2

Compound 25-1 (71.5.0 mg, 0.26 mmol) and intermediate III-2 (85.1 mg, 0.31 mmol, 1.2 eq.) are dissolved in 1.0 mL of NMP. DIPEA (2.5 mL) is added. The reaction mixture is stirred overnight at 95° C. The reaction mixture is diluted with ethyl acetate after the reaction is monitored to be complete, washed with saturated brine water for 5 times. The organic phase is concentrated, separated by column chromatography to obtain the compound 25-2 (71.7 mg, yield 54%).

Step Five: Synthesis of Compound 25-3

Compound 25-2 (71.7 mg, 0.14 mmol), Compound 11-5 (35.5 mg, 0.11 mmol, 0.8 eq.) $Pd_2(dba)_3$ (5.1 mg, 4 mol %), Xantphos (9.8 mg, 12 mol %) and cesium carbonate (91.3 mg, 0.28 mmol, 2 eq.) are placed in a sealed tube. Anhydrous dioxane (1.0 mL) is added after the protection of nitrogen. The reaction mixture is reacted overnight at 105° C. The reaction mixture is extracted with ethyl acetate after the reaction is monitored to be complete, dried with anhydrous sodium sulfate, concentrated, and separated by column chromatography to obtain Compound 25-3 (50.0 mg, yield 46%).

Step Six: Synthesis of Compound 25

Compound 25-3 (45.0 mg, 0.058 mmol) are dissolved in EA (1.0 mL) and EA·HCl (1.0 mL) is added. The reaction mixture is reacted overnight at the room temperature. The reaction mixture is adjusted on a pH value to be alkaline through adding sodium carbonate solution after the reaction is monitored to be complete, extracted with EA, dried and concentrated to obtain compound 25 (24.0 mg, yield 60%). $^1H$ NMR (300 MHz, Chloroform-d) δ 8.48 (dd, J=8.4, 1.4 Hz, 1H), 8.39 (d, J=3.8 Hz, 1H), 8.27-8.14 (m, 3H), 7.85-7.74 (m, 2H), 7.17 (t, J=8.1 Hz, 1H), 6.73 (dd, J=7.9, 1.4 Hz, 1H), 4.73 (p, J=6.9 Hz, 1H), 4.26-4.14 (m, 1H), 4.00-3.85 (m, 2H), 3.82 (d, J=8.8 Hz, 1H), 3.70 (d, J=8.8 Hz, 1H), 3.53-3.28 (m, 2H), 3.00 (d, J=4.5 Hz, 1H), 2.69 (s, 3H), 1.95-1.83 (m, 1H), 1.79-1.66 (m, 9H), 1.24 (d, J=6.4 Hz, 3H).

Example 26

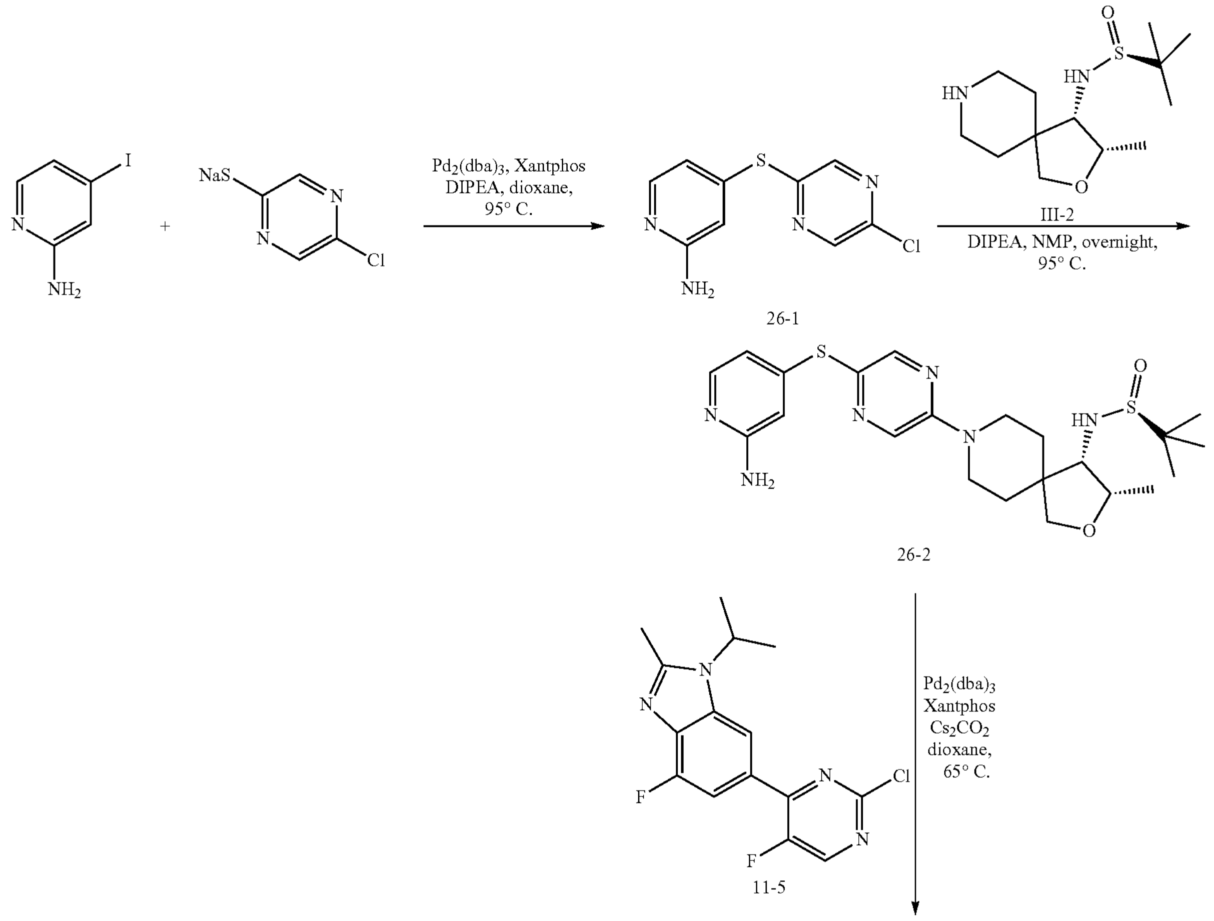

26-1

26-2

11-5

-continued

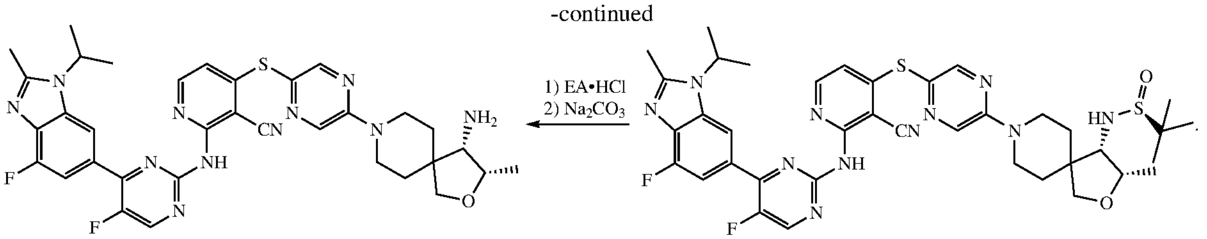

26 26-3

Step one: Synthesis of Compound 26-1

Compound 2-amino-4-iodopyridine (250.0 mg, 1.14 mmol), 5-chloro-2-pyrazine sulfonate sodium (249.5 mg, 1.48 mmol, 1.3 eq.) $Pd_2(dba)_3$ (21.1 mg, 2 mol %), Xantphos (19.7 mg, 3 mol %) and DIPEA (294.1 mg, 2.28 mmol, 2 eq.) are placed in a sealed tube. Anhydrous dioxane (3.0 mL) is added after the protection of nitrogen. The reaction mixture is reacted overnight at 95° C. The reaction mixture is extracted with ethyl acetate after the reaction is monitored to be complete, dried with anhydrous sodium sulfate, concentrated, and separated by column chromatography to obtain compound 26-1 (178.0 mg, yield 65%).

Step Two: Synthesis of Compound 26-2

Compound 26-1 (120.0 mg, 0.50 mmol), intermediate III-2 (164.6 mg, 0.60 mmol, 1.2 eq.) are dissolved in 1.0 mL of NMP. DIPEA (2.5 mL) is added. The reaction mixture is stirred overnight at 95° C. The reaction mixture is diluted with ethyl acetate after the reaction is monitored to be complete, washed with saturated brine water for 5 times. The organic phase is concentrated, separated by column chromatography to obtain Compound 26-2 (142.2 mg, yield 60%).

Step Three: Synthesis of Compound 26-3

Compound 26-2 (130.0 mg, 0.27 mmol), Compound 11-5 (74.2 mg, 0.23 mmol, 0.85 eq.), $Pd_2(dba)_3$ (10.1 mg, 4 mol %), Xantphos (18.5 mg, 12 mol %) and cesium carbonate (176.0 mg, 0.54 mmol, 2 eq.) are placed in a sealed tube. Anhydrous dioxane (1.0 mL) is added after the protection of nitrogen. The reaction mixture is reacted overnight at 105° C. The reaction mixture is extracted with ethyl acetate after the reaction is monitored to be complete, dried with anhydrous sodium sulfate, concentrated, and separated by column chromatography to obtain Compound 26-3 (110.0 mg, yield 53%).

Step Four: Synthesis of Compound 26

Compound 26-3 (90.0 mg, 0.12 mmol) is dissolved in EA (1.0 mL) and EA·HCl (1.0 mL) is added. The reaction mixture is reacted overnight at the room temperature. The reaction mixture is adjusted on a pH value to be alkaline through adding sodium carbonate solution after the reaction is monitored to be complete, extracted with EA, dried and concentrated to obtain compound 26 (65.0 mg, yield 82%). $^1H$ NMR (300 MHz, Chloroform-d) δ 8.37 (d, J=3.7 Hz, 1H), 8.35 (dd, J=1.7, 0.7 Hz, 1H), 8.26 (d, J=1.4 Hz, 1H), 8.21-8.04 (m, 3H), 8.01 (d, J=1.4 Hz, 1H), 7.73 (d, J=11.8 Hz, 1H), 6.62 (dd, J=5.4, 1.7 Hz, 1H), 4.77 (p, J=6.9 Hz, 1H), 4.20 (dd, J=6.5, 4.6 Hz, 1H), 3.97-3.78 (m, 3H), 3.69 (d, J=8.8 Hz, 1H), 3.50-3.27 (m, 2H), 3.01 (d, J=4.6 Hz, 1H), 2.70 (s, 3H), 1.94-1.82 (m, 1H), 1.78-1.64 (m, 9H), 1.25 (d, J=6.4 Hz, 3H).

SHP2 Enzyme Activity Test In Vitro

SHP2 enzyme activity of the compounds in the above examples are tested as follows.

4.1 Compound Formulation

The compound is dissolved in 100% DMSO to prepare into a 30 mM storage solution, which is stored in −20° C. refrigerator in the dark.

4.2 SHP2 reaction Process (1) 1×ReactionBuffer is prepared.

(2) The preparation of concentration gradient of the compound: the tested compound is tested at an initial concentration of 30 M with a 3-fold dilution and 10 concentrations in a single well, diluted into a 100% DMSO solution at a 100-fold final concentration in a 384 source plate, diluted by 3-fold through Precision with 10 concentrations, 250 nL of compound with a 100-fold final concentration is transferred to the target plate of 384 plate by using a dispenser Echo 550, with an addition of 250 nL DMSO to the positive control and an addition of 250 nL 1 mm SHP099 to the negative control.

(3) An activation peptide solution with a 5-fold final concentration is prepared by using 1×ReactionBuffer, and 5 μL of the activation peptide solution is added to the reaction plates, respectively, and centrifuged at 1000 rpm for 1 minute.

(4) An enzyme solution with a 2.5-fold final concentration is prepared by using 1×ReactionBuffer, and 10 μL of the enzyme solution is added to the reaction plates, respectively, centrifuged at 1000 rpm for 1 minute and incubated at the room temperature for 60 minutes.

(5) A substrate solution with a 2.5-fold final concentration is prepared by using 1×ReactionBuffer, 10 μL of the substrate solution is added to the reaction plates, respectively, centrifuged at 1000 rpm for 1 minute and incubated at the room temperature for 20 minutes.

(6) Ex355/Em460 fluorescence values are read by EnSight 4.3 Data analysis

The calculation formula is as follows:

$$\%\ \text{Inhibition} = \frac{\text{Mean}\,(PC) - RFU}{\text{Mean}\,(PC) - \text{Mean}\,(NC)} \times 100.$$

RFU denotes a fluorescence value for the sample; Mean (NC) denotes an average fluorescence value for the control wells including 10 μM SHP099; mean (PC) denotes an average fluorescence value for positive control wells.

Fitting Dose-Response Curve

The log value for concentration is taken as X-axis and the percent inhibition is taken as Y-axis, and the log (inhibitor) vs. response variable slope of the analysis software GraphPad Prism 5 is used to fit the dose-response curve to obtain the IC50 values for each compound on enzyme activity.

The calculation formula is Y=bottom+(Top−Bottom)/(1+10^LogIC50-X)*HillSlope))

CDK4 Enzyme Activity Test In Vitro 5.1 Compound Formulation

The compound is dissolved in 100% DMSO to prepare into a 30 mM storage solution, which is stored in −20° C. refrigerator in the dark.

5.2 Kinase Reaction Procedure (1) 1×Kinase buffer is prepared.

(2) The preparation of concentration gradient of the compound: tested compound is tested at an initial concentration of 30000 nM according to a customer's request, diluted into a 100% DMSO solution at a 100-fold final concentration in a 384 source plate, diluted by 3-fold with 10 concentrations, 250 nL of compound with a 100-fold final concentration is transferred to the target plate of 384-well-plate by using a dispenser Echo 550.

(3) A Kinase solution with a 2.5-fold final concentration is prepared by using a 1×Kinase buffer.

(4) 10 μL of kinase solution with a 2.5-fold final concentration is added to the compound wells and the positive control wells, respectively; 10 μL of 1×Kinase buffer is added to the negative control wells.

(5) The kinase solution is centrifugated at 1000 rpm for 30 seconds, and incubated at the room temperature for 10 minutes after the reaction plate is shaken and mixed uniformly.

(6) A mixed solution of ATP and Kinase substrate 8 is prepared at a 25/15-fold final concentration by using a 1×Kinase buffer.

(7) The reaction is initiated by adding 15 μL of the mixed solution of ATP and substrate at a 5/3-fold final concentration.

(8) The 384-well plate is centrifuged at 1000 rpm for 30 seconds, and incubated at the room temperature for 180 minutes after shaking and mixing uniformly.

(9) The kinase reaction is terminated by adding 30 μL of termination detection solution, centrifuged at 1000 rpm for 30 seconds with shaking and mixing uniformly.

(10) The conversion is read by using Caliper EZ Reader II.

5.3 Data Analysis

Calculation Formula is as follows:

$$\%\ \text{Inhibition} = \frac{\text{Conversion}\ \%\_\text{max} - \text{Conversion}\ \%\_\text{sample}}{\text{Conversion}\ \%\_\text{max} - \text{Conversion}\ \%\_\text{min}} \times 100.$$

Conversion %_sample denotes a conversion reading of the sample; Conversion % min denotes an average value for negative control wells, represents a conversion reading without enzyme wells; Convesion %_max denotes an average value for positive control wells, represents a conversion reading without compound inhibition wells.

The specific results are shown in the table:

| Number of the compound | SHP2 $IC_{50}$ (nM) | CDK4 $IC_{50}$ (nM) |
|---|---|---|
| 1 | >1000 | >1000 |
| 2 | >1000 | 9 |
| 3 | 57 | >1000 |
| 4 | 30 | 435 |
| 5 | 4 | >1000 |
| 6 | 736 | >1000 |
| 7 | >1000 | >1000 |
| 8 | >1000 | 905 |
| 9 | 36 | 538 |
| 10 | 10 | 96 |

-continued

| Number of the compound | SHP2 $IC_{50}$ (nM) | CDK4 $IC_{50}$ (nM) |
|---|---|---|
| 11 | >1000 | 31 |
| 12 | >1000 | 141 |
| 13 | 216 | 11 |
| 14 | 5 | 19 |
| 15 | >1000 | 145 |
| 16 | >1000 | 51 |
| 17 | >1000 | >1000 |
| 19 | 9 | 3 |
| 20 | 598 | 123 |
| 21 | >1000 | 9 |
| 23 | 61 | 7 |
| 24 | >1000 | >1000 |
| 25 | 15 | 8 |
| 26 | 48 | 17 |
| SHP099 | 78 | — |
| Abemaciclib | — | 1.6 |

In Vitro Antiproliferative Activity of Compound

1. Experimental Procedure (1) The PBS solution is autoclaved and stored in a refrigerator at 4° C.

(2) Trypsin and pancreatin digestion solution are weighed, fully dissolved in ultrapure water, filtered with microporous filter to obtain liquid for storing in the refrigerator at −20° C.

(3) Culture medium powder and $NaHCO_3$ are weighed respectively with an addition of ultrapure water for a full dissolution, filtered with microporous membrane with an addition of 10% of diabody to obtain a culture solution, the culture solution is stored at 4° C. in refrigerator with an addition of 10% of fetal bovine serum before use.

(4) MDA-MB-231, MDA-MB-468 or EMT6 cells are taken out of a liquid nitrogen tank, immediately placed in a constant temperature water bath at 37° C. and melted by shaking, then the cells are poured into a culture flask. The culture solution (containing 10% of fetal bovine serum) is added for dilution. The diluted culture medium is transferred into a centrifuge tube, centrifuged at 1000 r/min for 5 minutes. The supernatant is discarded and fresh culture medium is added for blowing and mixing uniformly. The mixture is transferred into a culture bottle, and cultured in a culture box with a concentration of 5% $CO_2$ at 37° C. When the cells are adhered to the wall and almost fully paved at the bottle bottom, the passage begins. A little amount of fresh culture medium (containing 10% of fetal calf serum) is added to terminate the digestion. The liquid in the culture bottle is poured out, and the culture bottle is washed twice with PBS. The fresh culture medium is added to blow and mix uniformly, and divided evenly into two culture bottles for continuing the culture.

(5) Cells in the logarithmic phase are taken, and the old culture medium are poured out. The trypsin solution is added for digestion for 3 minutes, and the fresh culture medium containing 10% of fetal bovine serum is added for terminating digestion. The solution is transferred into a centrifuge tube, centrifuged at 1000 r/min for 5 minutes, and the supernatant is discarded. The cells are counted by adding a medium to prepare into a cell suspension. After counting, cells are seeded in 96-well plates at a cell concentration of 5000-10000 cells per well. The 96-well plate with the spread cells is placed in a 5% $CO_2$ incubator at 37° C. for a continuous culture for 24 hours. The drugs are diluted in gradient to 90μ mol/L, 30μ mol/L, 10μ mol/L, 3.3 g mol/L, 1.1 g mol/L, 0.37μ mol/L with medium and then added to 96-well plates at 100 μL per well, with three multiplex wells per concentration. The control group is added with medium containing solvent with the corresponding concentration, the zeroing hole is added with blank medium with the same volume, and the blank medium is placed in a culture box with 5% $CO_2$ and 37° C. for 3 days of incubation with a replacement of the medium every two days. 20 μL of MTT (5 mg/mL) is added to each well. After mixing uniformly, the mixture is incubated in a 5% $CO_2$ incubator at 37° C. for 4 hours in the absence of light. With a removement of the liquid in the 96-well plate and an addition of 150 μl of DMSO to each well, the mixture is placed on a micro-shaker and shaken to completely dissolve the crystals at the bottom. Subsequently, the 96-well plate is placed in an microplate reader for detection and the absorbance is measured at 490 nm.

Curve is drawn and inhibition rate of drug to cell and $IC_{50}$ are calculated.

Inhibition ratio=[(average OD value for control group-average OD value for experimental group)/(average OD value for control group-average OD value for blank control group)]× 100%.

3. Experimental Results

The inhibitory activities of the compounds on MDA-MB-231, MDA-MB-468 and EMT6 cell lines are as follows:

| | $IC_{50}$ value (μM) | | |
|---|---|---|---|
| Compd. | MDA-MB-231 | MDA-MB-468 | EMT6 |
| 10 | 4.4 | 5.9 | 1.1 |
| 14 | 6.4 | 1.8 | 0.6 |
| 19 | 9.6 | 3.7 | 0.7 |
| 23 | 3.2 | 10.5 | 1.7 |
| 25 | 4.6 | 9.1 | 0.6 |
| 26 | 5.1 | 9.6 | 1.1 |
| TNO155 | >20 | >20 | 7.0 |
| Abemaciclib | >20 | >20 | 4.2 |
| TNO155 + Abemacic lib | 13.0 | 3.4 | 2.5 |

Conclusion of experiment: the compounds of the various embodiments in the present disclosure have better antiproliferative effects on MDA-MB-231, MDA-MB-468, and EMT6 cells than SHP2 and CDK4/6 inhibitors, either alone or in combination.

Cell Cycle Experiments of Compound

Cell lines of MDA-MB-231 and MDA-MB-468 are seeded in six well plates and treated with DMSO, TNO155, Abemaciclib, TNO155+Abemaciclib, or compound 12 at different concentrations for 48 hours. Cells are washed once with PBS and 1 mL of trypsin without EDTA (0.25%) is added. When cells change round and part of the cells are suspended, the digestion is terminated by adding PBS, subsequently, the cells are harvested and fixed in 70% ethanol (500 μL) at 4° C. for 24 hours. Cells are collected by washing with PBS and centrifuged at 1500 rpm for 5 minutes, then stained with PI/RNase in the dark at the room temperature for 30 minutes-60 minutes. After incubation, the cells are analyzed by flow cytometry. All experiments are performed 3 times.

Figure 2:
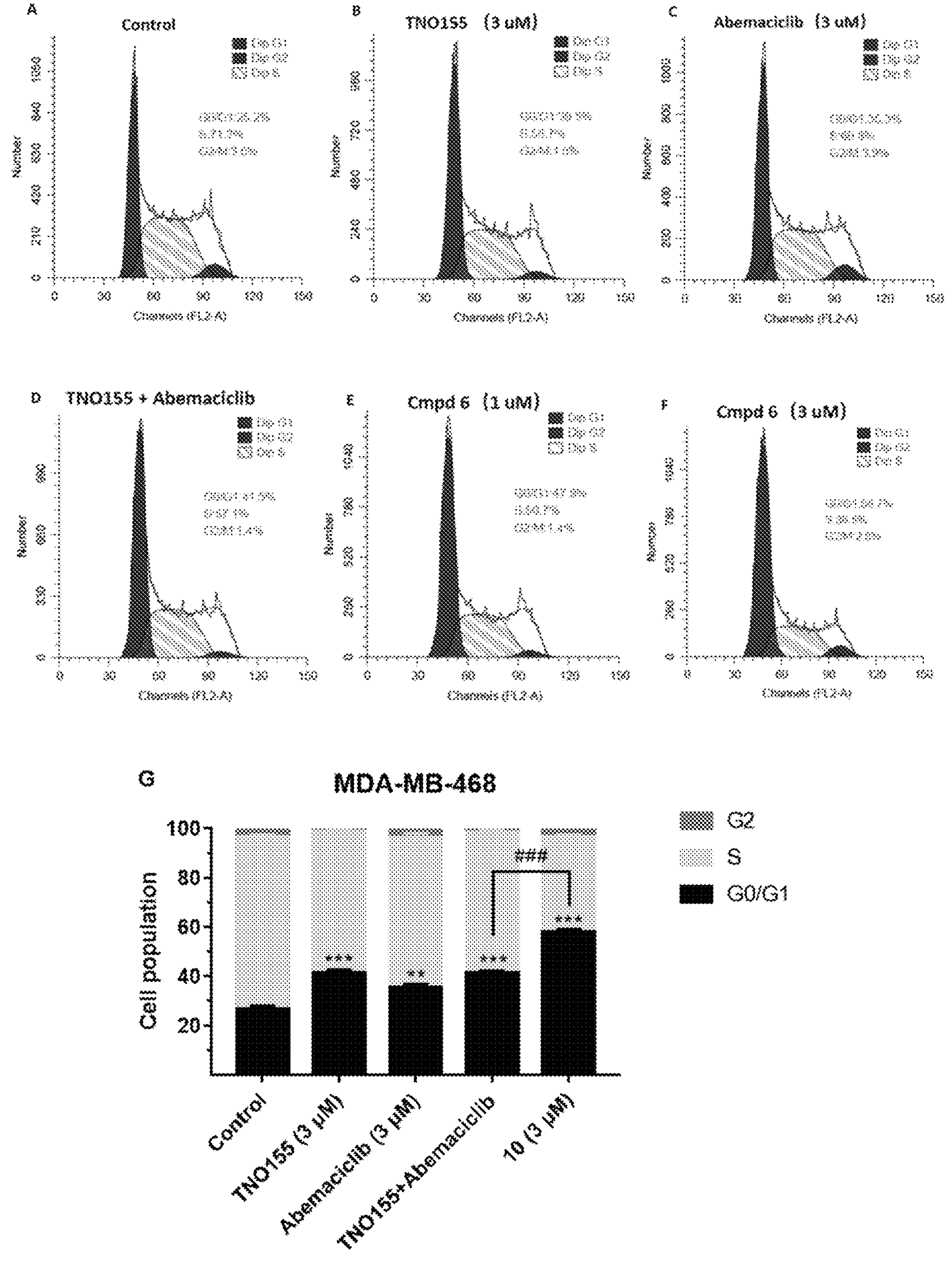
FIG. 2 illustrates an influence of Compound 14 on a cell cycle of MDA-MB-468; where A is control, B is TNO155, C is Abemaciclib, D is TN0155+Abemaciclib, E is Cmpd6 (1μ M), and F is Cmpd6 (6μ M).

Conclusion of experiment: as illustrated in FIG. 1 and FIG. 2, the compounds of the various embodiments in the present disclosure have better G0/G1 cycle blocking effects on MDA-MB-231 and MDA-MB-468 cells than SHP2 and CDK4/6 inhibitors, either alone or in combination.

What is claimed is:

1. A compound as shown in General Formula III, and pharmaceutically acceptable salts, enantiomers, diastereomers, tautomers, solvates, polymorphs, or prodrugs thereof

III

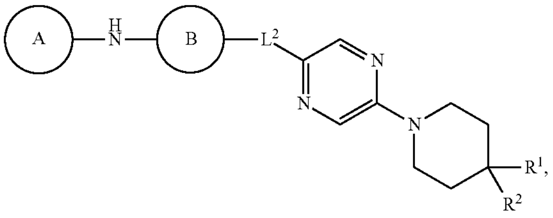

wherein, ring A is selected from

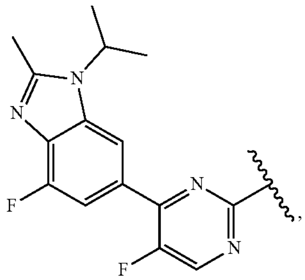
,

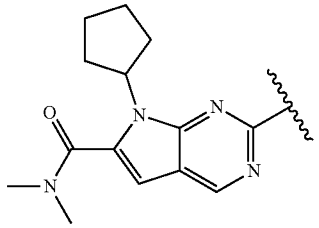
or

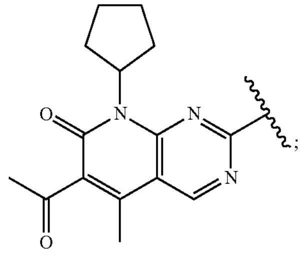
;

ring B is selected from aromatic ring, heteroaromatic ring, carbocyclic ring, heterocyclic ring; wherein the aromatic ring, the heteroaromatic ring, the carbocyclic ring, the heterocyclic ring optionally contain heteroatoms selected from N, O and $S(O)_m$; where m is selected from 0, 1 and 2; where the aromatic ring, the heteroaromatic ring, the carbocyclic ring, the heterocyclic ring are optionally substituted with one or a plurality of substituents;

$L^2$ is a chemical bond, $NR^a$, a carbon chain with $C_1$-$C_2$, O, $S(O)_m$, where m is selected from 0, 1 and 2;

$R^1$, $R^2$ are hydrogen, deuterium atom, halogen, amino, hydroxy, cyano, nitro, carboxyl, sulfonic acid group and $C_1$-$C_6$ alkyl, $C_3$-$C_6$ cycloalkyl, $C_6$-$C_{10}$ aryl, $C_6$-$C_{10}$ heteroaryl, respectively; wherein the amino, the hydroxy, the aryl, the heteroaryl, the cycloalkyl are optionally substituted with one or a plurality of substituents;

alternatively, a 3 membered to 12 membered mono-heterocyclic ring or polycyclic heterocyclic ring is formed by $R^1$ and $R^2$ together with the carbon atoms attached to both $R^1$ and $R^2$, wherein the mono-heterocyclic ring or the polycyclic heterocyclic ring optionally contains heteroatoms selected from N, O and $S(O)_m$; wherein m is selected from 0, 1 and 2; where the mono-heterocyclic ring or the polycyclic heterocyclic ring is unsubstituted or substituted with one or a plurality of substituents;

alternatively,

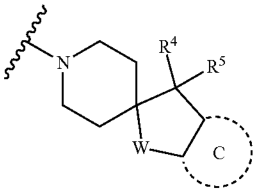

is formed by $R^1$ and $R^2$ together with the carbon atoms attached to both $R^1$ and $R^2$, wherein W is absent or selected from $CR^6R^7$, O, $NR^b$, $S(O)_m$, where m is selected from 0, 1 and 2;

ring C is absent or selected from $C_3$-$C_7$ membered monocyclic ring, or $C_5$-$C_{12}$ membered polycyclic ring;

$R^a$, $R^b$ are independently selected from hydrogen, deuterium atoms, $C_1$-$C_6$ alkyl, $C_3$-$C_6$ cycloalkyl, $C_6$-$C_{10}$ aryl, $C_6$-$C_{10}$ heteroaryl;

$R^4$, $R^5$, $R^6$, $R^7$ are independently selected from hydrogen, deuterium atom, halogen, amino, hydroxy, cyano, nitro, carboxyl, sulfonic acid group, $C_1$-$C_6$ alkyl, $C_3$-$C_6$ cycloalkyl, $C_6$-$C_{10}$ aryl, $C_6$-$C_{10}$ heteroaryl; where the amino, the hydroxy, the aryl, the heteroaryl, the cycloalkyl are optionally substituted with one or a plurality of substituents;

alternatively, CO, C═NH, $C_3$-$C_{12}$ membered heterocyclic ring or $C_3$-$C_8$ cycloalkyl is formed by $R^4$ and $R^5$ together with the carbon atoms attached to both $R^4$ and $R^5$.

2. The compound according to claim 1, wherein the compound is any one of following structural formulas:

| Number | Structure of the compound |
|---|---|
| 2 | 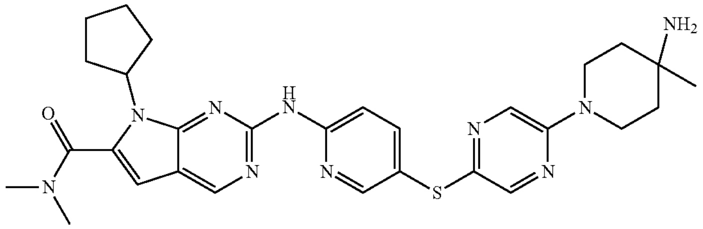 |
| 3 | 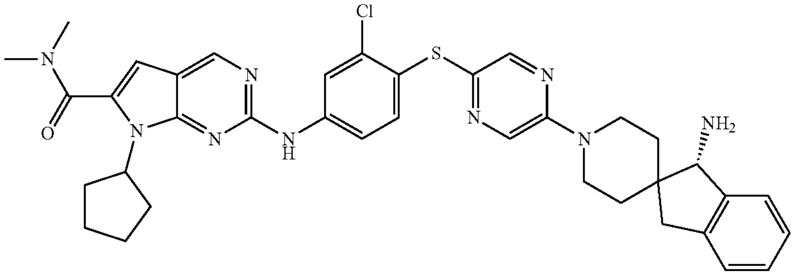 |
| 4 | 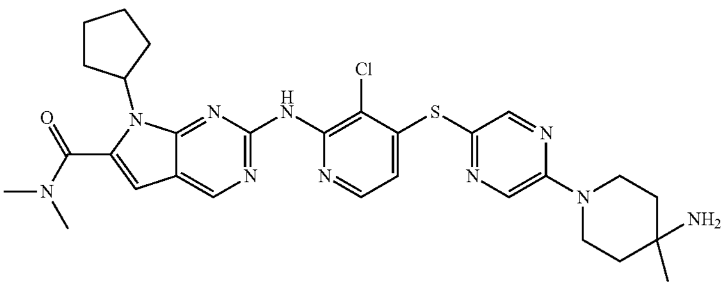 [SMILES: CN(C)C(=O)c1cc2cnc(Nc3nccc(Sc4cnc(N5CCC(C)(N)CC5)cn4)c3Cl)nc2n1C1CCCC1] |

-continued
| Number | Structure of the compound |
|---|---|
| 5 | 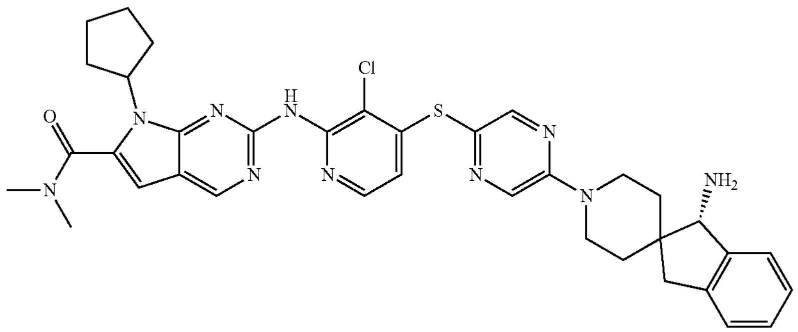 [SMILES: CN(C)C(=O)c1cc2cnc(Nc3nccc(Sc4cnc(N5CCC6(CC5)Cc5ccccc5[C@H]6N)cn4)c3Cl)nc2n1C1CCCC1] |
| 6 | 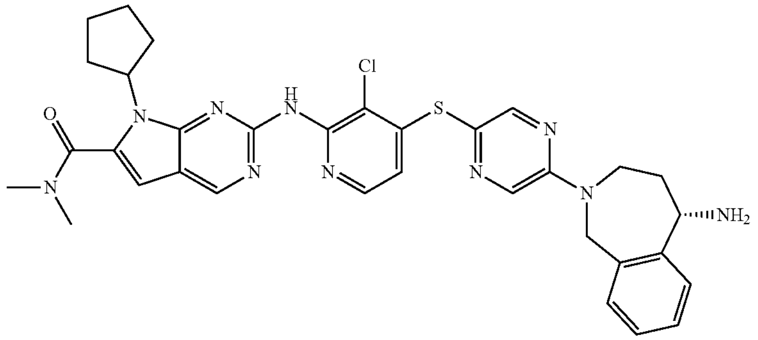 [SMILES: CN(C)C(=O)c1cc2cnc(Nc3nccc(Sc4cnc(N5CC[C@H](N)c6ccccc6C5)cn4)c3Cl)nc2n1C1CCCC1] |
| 8 | 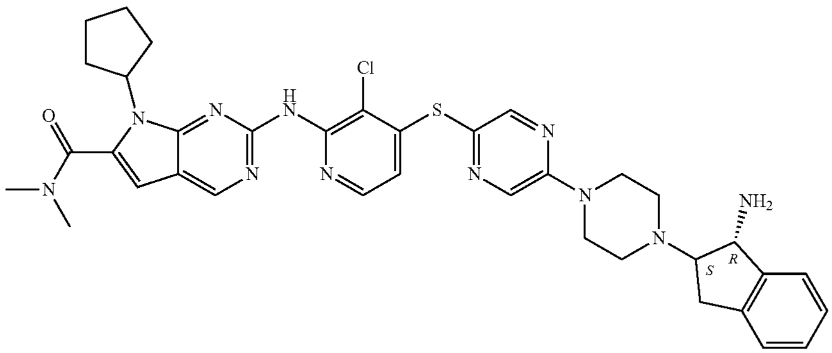 |
| 9 | 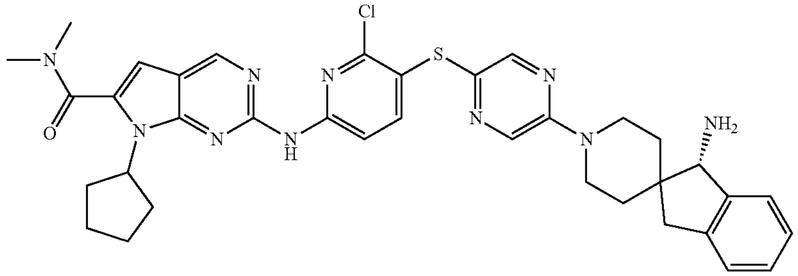 [SMILES: CN(C)C(=O)c1cc2cnc(Nc3ccc(Sc4cnc(N5CCC6(CC5)Cc5ccccc5[C@H]6N)cn4)c(Cl)n3)nc2n1C1CCCC1] |

-continued
| Number | Structure of the compound |
|---|---|
| 10 | 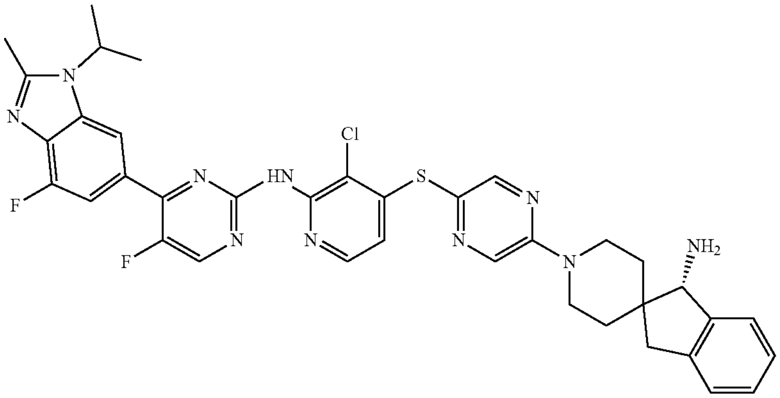 [SMILES: Cc1nc2c(F)cc(-c3nc(Nc4nccc(Sc5cnc(N6CCC7(CC6)Cc6ccccc6[C@H]7N)cn5)c4Cl)ncc3F)cc2n1C(C)C] |
| 11 | 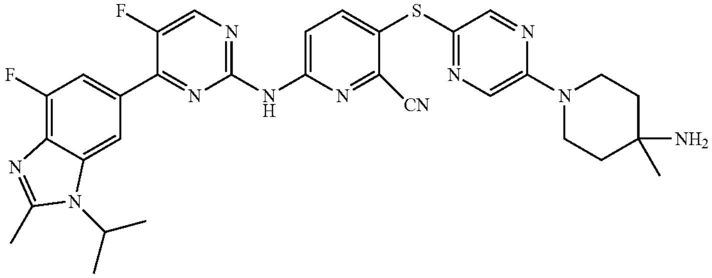 [SMILES: Cc1nc2c(F)cc(-c3nc(Nc4ccc(Sc5cnc(N6CCC(C)(N)CC6)cn5)c(C#N)n4)ncc3F)cc2n1C(C)C] |
| 12 | 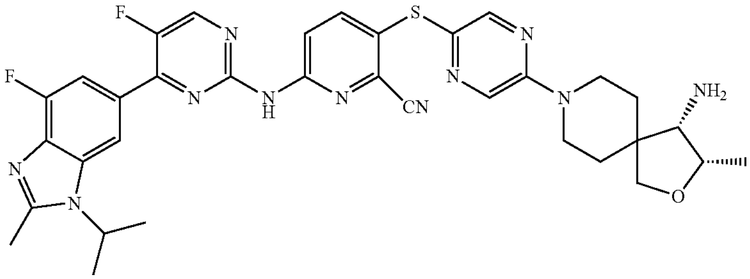 [SMILES: Cc1nc2c(F)cc(-c3nc(Nc4ccc(Sc5cnc(N6CCC7(CC6)CO[C@@H](C)[C@H]7N)cn5)c(C#N)n4)ncc3F)cc2n1C(C)C] |
| 13 | 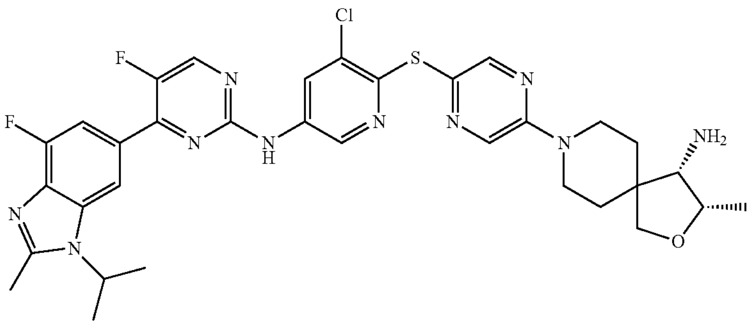 |

-continued
| Number | Structure of the compound |
|---|---|
| 14 | 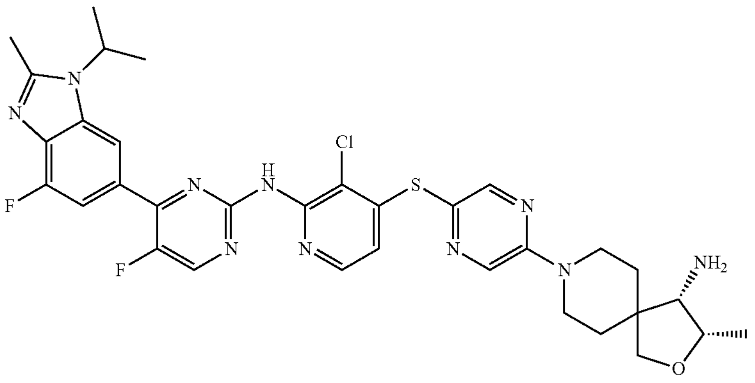 [SMILES: Cc1nc2c(F)cc(-c3nc(Nc4nccc(Sc5cnc(N6CCC7(CC6)CO[C@@H](C)[C@H]7N)cn5)c4Cl)ncc3F)cc2n1C(C)C] |
| 15 | 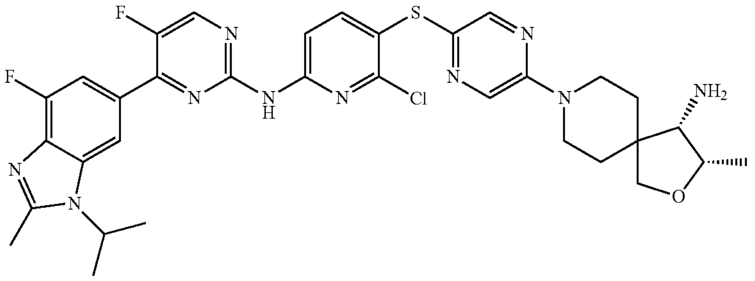 [SMILES: Cc1nc2c(F)cc(-c3nc(Nc4ccc(Sc5cnc(N6CCC7(CC6)CO[C@@H](C)[C@H]7N)cn5)c(Cl)n4)ncc3F)cc2n1C(C)C] |
| 16 | 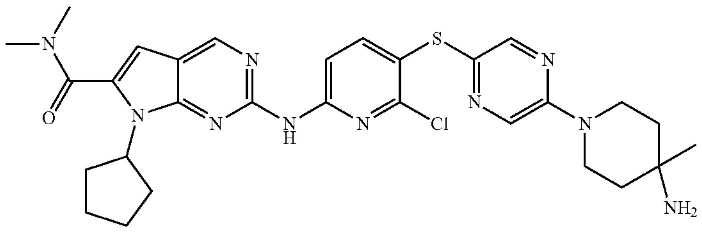 |
| 17 | 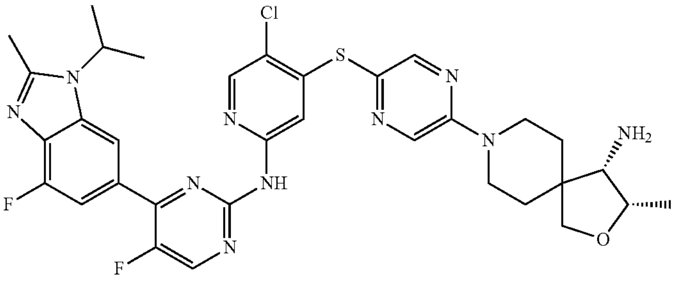 [SMILES: Cc1nc2c(F)cc(-c3nc(Nc4cc(Sc5cnc(N6CCC7(CC6)CO[C@@H](C)[C@H]7N)cn5)c(Cl)cn4)ncc3F)cc2n1C(C)C] |
| 18 | 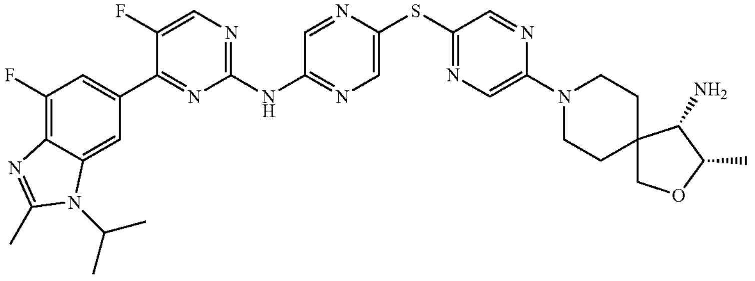 [SMILES: Cc1nc2c(F)cc(-c3nc(Nc4cnc(Sc5cnc(N6CCC7(CC6)CO[C@@H](C)[C@H]7N)cn5)cn4)ncc3F)cc2n1C(C)C] |

-continued
| Number | Structure of the compound |
|---|---|
| 19 | 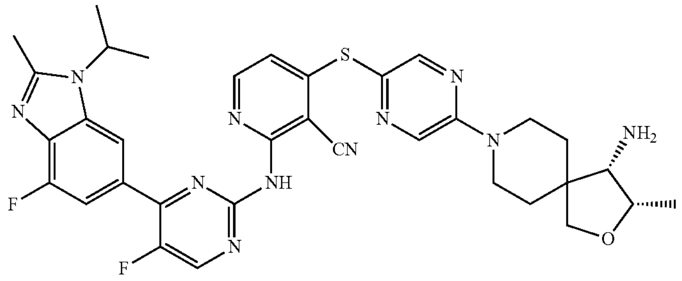 [SMILES: Cc1nc2c(F)cc(-c3nc(Nc4nccc(Sc5cnc(N6CCC7(CC6)CO[C@@H](C)[C@H]7N)cn5)c4C#N)ncc3F)cc2n1C(C)C] |
| 20 | 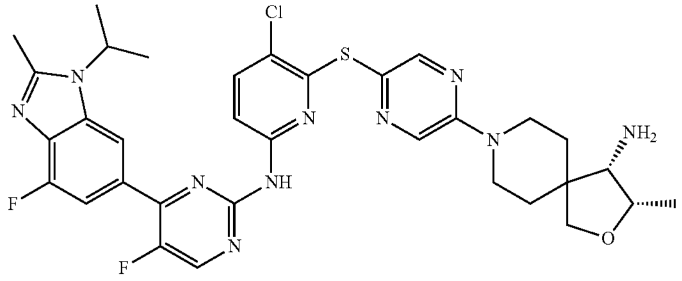 |
| 21 | 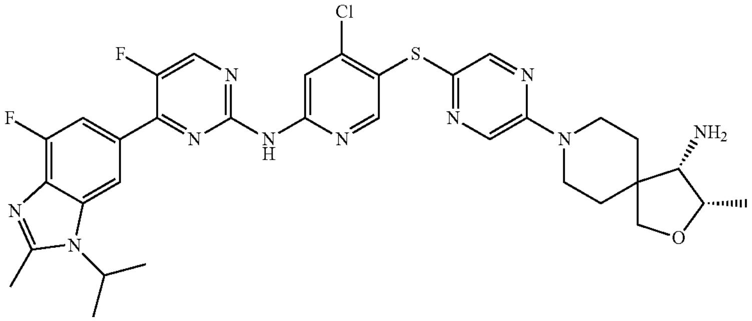 |
| 22 | 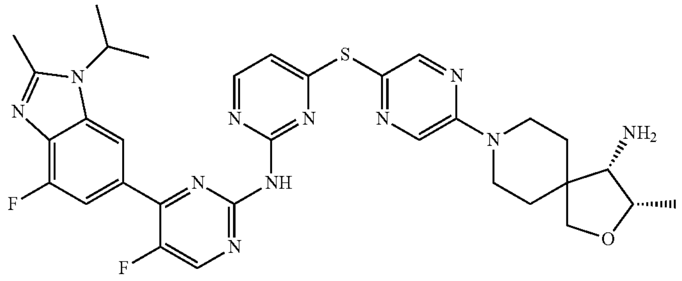 |
| 23 | 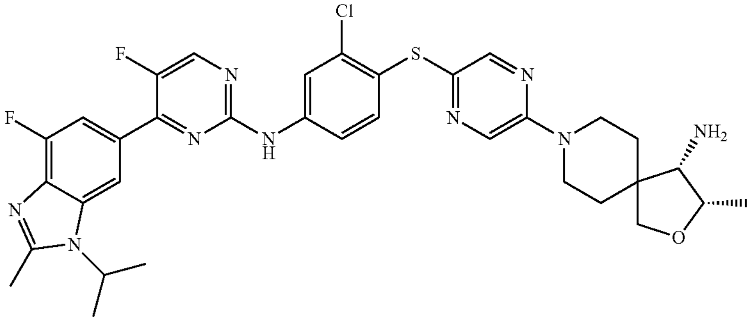 [SMILES: Cc1nc2c(F)cc(-c3nc(Nc4ccc(Sc5cnc(N6CCC7(CC6)CO[C@@H](C)[C@H]7N)cn5)c(Cl)c4)ncc3F)cc2n1C(C)C] |

-continued

| Number | Structure of the compound |
|---|---|
| 24 | 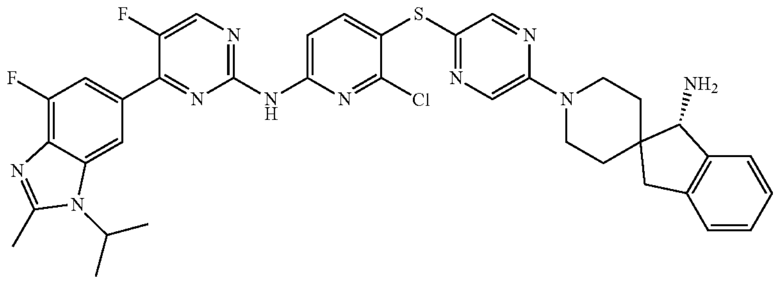 [SMILES: Cc1nc2c(F)cc(-c3nc(Nc4ccc(Sc5cnc(N6CCC7(CC6)Cc6ccccc6[C@H]7N)cn5)c(Cl)n4)ncc3F)cc2n1C(C)C] |
| 25 | 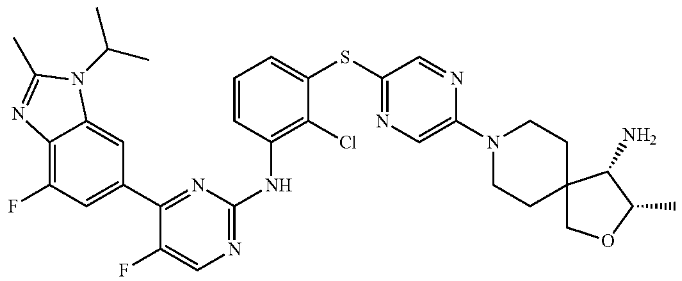 [SMILES: Cc1nc2c(F)cc(-c3nc(Nc4cccc(Sc5cnc(N6CCC7(CC6)CO[C@@H](C)[C@H]7N)cn5)c4Cl)ncc3F)cc2n1C(C)C] |
| 26 | 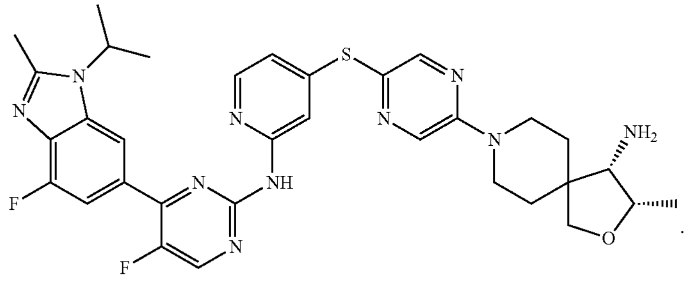 [SMILES: Cc1nc2c(F)cc(-c3nc(Nc4cc(Sc5cnc(N6CCC7(CC6)CO[C@@H](C)[C@H]7N)cn5)ccn4)ncc3F)cc2n1C(C)C] |

3. A pharmaceutical composition containing the compound of claim 1 and a pharmaceutically acceptable excipient.

4. The pharmaceutical composition according to claim 3, wherein the pharmaceutical composition is prepared into a tablet, a capsule, an injection, or a lyophilized powder.

5. A pharmaceutical composition containing the compound of claim 2 and a pharmaceutically acceptable excipient.

6. The pharmaceutical composition according to claim 5, wherein the pharmaceutical composition is prepared into a tablet, a capsule, an injection, or a lyophilized powder.

* * * * *